United States Patent
Markel et al.

(10) Patent No.: US 9,771,431 B2
(45) Date of Patent: *Sep. 26, 2017

(54) ANTIBODIES TO CARCINOEMBRYONIC ANTIGEN-RELATED CELL ADHESION MOLECULE (CEACAM)

(71) Applicants: TEL HASHOMER MEDICAL RESEARCH INFRASTRUCTURE AND SERVICES LTD., Ramat Gan (IL); CCAM BIOTHERAPEUTICS LTD., Kiryat-Shmona (IL); RAMOT AT TEL-AVIV UNIVERSITY LTD., Tel Aviv (IL)

(72) Inventors: Gal Markel, Tel Aviv (IL); Tehila Ben Moshe, Misgav (IL); Yair Sapir, Burgata (IL); Ilana Mandel, Kiryat Yam (IL); Jacob Schachter, Givatayim (IL); Rona Ortenberg, Tel Aviv (IL)

(73) Assignee: CCAM BIOTHERAPEUTICS LTD., Hod Hasharon (IL)

( * ) Notice: Subject to any disclaimer, the term of this patent is extended or adjusted under 35 U.S.C. 154(b) by 119 days.

This patent is subject to a terminal disclaimer.

(21) Appl. No.: 14/350,970

(22) PCT Filed: Oct. 10, 2012

(86) PCT No.: PCT/IL2012/050402
§ 371 (c)(1),
(2) Date: Apr. 10, 2014

(87) PCT Pub. No.: WO2013/054331
PCT Pub. Date: Apr. 18, 2013

(65) Prior Publication Data
US 2014/0271618 A1    Sep. 18, 2014

(30) Foreign Application Priority Data

Oct. 11, 2011    (WO) .................. PCT/IL2011/000808

(51) Int. Cl.
| | | |
|---|---|---|
| C07K 16/42 | (2006.01) |
| C07K 16/30 | (2006.01) |
| A61K 35/17 | (2015.01) |
| A61K 39/395 | (2006.01) |
| A61K 45/06 | (2006.01) |
| G01N 33/68 | (2006.01) |
| A61K 39/00 | (2006.01) |

(52) U.S. Cl.
CPC ............ *C07K 16/42* (2013.01); *A61K 35/17* (2013.01); *A61K 39/39566* (2013.01); *A61K 45/06* (2013.01); *C07K 16/3007* (2013.01); *G01N 33/686* (2013.01); *A61K 2039/505* (2013.01); *C07K 2317/24* (2013.01); *C07K 2317/73* (2013.01); *C07K 2317/76* (2013.01); *C07K 2317/92* (2013.01)

(58) Field of Classification Search
None
See application file for complete search history.

(56) References Cited

U.S. PATENT DOCUMENTS

| | | |
|---|---|---|
| 3,791,932 A | 2/1974 | Schuurs et al. |
| 3,839,153 A | 10/1974 | Schuurs et al. |
| 3,850,578 A | 11/1974 | McConnell |
| 3,850,752 A | 11/1974 | Schuurs et al. |
| 3,853,987 A | 12/1974 | Dreyer |
| 3,867,517 A | 2/1975 | Ling |
| 3,879,262 A | 4/1975 | Schuurs et al. |
| 3,901,654 A | 8/1975 | Gross |
| 3,935,074 A | 1/1976 | Rubenstein et al. |
| 3,984,533 A | 10/1976 | Uzgiris |
| 3,996,345 A | 12/1976 | Ullman et al. |
| 4,034,074 A | 7/1977 | Miles |
| 4,036,945 A | 7/1977 | Haber |
| 4,098,876 A | 7/1978 | Piasio et al. |
| 4,331,647 A | 5/1982 | Goldenberg |
| 4,348,376 A | 9/1982 | Goldenberg |
| 4,666,828 A | 5/1987 | Gusella |
| 4,683,202 A | 7/1987 | Mullis |
| 4,801,531 A | 1/1989 | Frossard |
| 4,816,567 A | 3/1989 | Cabilly et al. |
| 4,879,219 A | 11/1989 | Wands et al. |
| 4,946,778 A | 8/1990 | Ladner et al. |

(Continued)

FOREIGN PATENT DOCUMENTS

| | | |
|---|---|---|
| EP | 0404097 A2 | 12/1990 |
| EP | 1133311 B1 | 10/2006 |

(Continued)

OTHER PUBLICATIONS

Simeone et al. (Pancreas, 34(4): 436-443, 2007).*

(Continued)

*Primary Examiner* — Brad Duffy
*Assistant Examiner* — Nelson B Moseley, II
(74) *Attorney, Agent, or Firm* — Rothwell, Figg, Ernst & Manbeck, P.C.

(57) ABSTRACT

The present invention provides antibodies, as well as molecules having at least the antigen-binding portion of an antibody, recognizing a specific epitope of the protein CEACAM1 and optionally binds also other subtypes of the CEACAM protein family. Disclosed antibodies and antibody fragments are characterized by specific CDR sequences. Methods of production and use in therapy and diagnosis of such antibodies and antibody fragments are also provided.

19 Claims, 22 Drawing Sheets

(56) References Cited

U.S. PATENT DOCUMENTS

| | | | |
|---|---|---|---|
| 5,011,771 | A | 4/1991 | Bellet et al. |
| 5,091,513 | A | 2/1992 | Huston et al. |
| 5,096,815 | A | 3/1992 | Ladner et al. |
| 5,192,659 | A | 3/1993 | Simons |
| 5,225,539 | A | 7/1993 | Winter |
| 5,272,057 | A | 12/1993 | Smulson et al. |
| 5,281,521 | A | 1/1994 | Trojanowski et al. |
| 5,530,101 | A | 6/1996 | Queen et al. |
| 5,545,806 | A | 8/1996 | Lonberg et al. |
| 5,545,807 | A | 8/1996 | Surani et al. |
| 5,569,825 | A | 10/1996 | Lonberg et al. |
| 5,585,089 | A | 12/1996 | Queen et al. |
| 5,625,126 | A | 4/1997 | Lonberg et al. |
| 5,633,425 | A | 5/1997 | Lonberg et al. |
| 5,641,870 | A | 6/1997 | Rinderknecht et al. |
| 5,661,016 | A | 8/1997 | Lonberg et al. |
| 5,693,761 | A | 12/1997 | Queen et al. |
| 5,693,762 | A | 12/1997 | Queen et al. |
| 5,750,373 | A | 5/1998 | Garrard et al. |
| 5,910,573 | A | 6/1999 | Pluckthun et al. |
| 6,013,772 | A | 1/2000 | Barnett et al. |
| 7,579,392 | B2 | 8/2009 | Gan et al. |
| 7,820,410 | B2 | 10/2010 | Benes et al. |
| 8,062,636 | B2 | 11/2011 | Goldenberg et al. |
| 8,598,322 | B2 | 12/2013 | Markel et al. |
| 2002/0028203 | A1 | 3/2002 | Blumberg |
| 2003/0022292 | A1 | 1/2003 | Gray-Owen et al. |
| 2003/0190600 | A1 | 10/2003 | Holmes |
| 2004/0047858 | A1 | 3/2004 | Blumberg et al. |
| 2004/0214184 | A1 | 10/2004 | Skubitz et al. |
| 2005/0107324 | A1 | 5/2005 | Bennett et al. |
| 2005/0169922 | A1 | 8/2005 | Blumberg |
| 2006/0039913 | A1* | 2/2006 | Das ............ C07K 16/24  424/146.1 |
| 2006/0058257 | A1 | 3/2006 | Wagener |
| 2007/0071758 | A1 | 3/2007 | Markel |
| 2007/0110668 | A1 | 5/2007 | Markel |
| 2008/0102071 | A1 | 5/2008 | Blumberg |
| 2008/0108140 | A1 | 5/2008 | Markel |
| 2009/0136528 | A1 | 5/2009 | Singh et al. |
| 2009/0226444 | A1 | 9/2009 | Rau et al. |
| 2011/0104148 | A1 | 5/2011 | Moessner |
| 2014/0120554 | A1* | 5/2014 | Markel ............ C07K 16/2803  435/7.23 |

FOREIGN PATENT DOCUMENTS

| | | |
|---|---|---|
| EP | 1276770 B1 | 10/2007 |
| EP | 1558284 B1 | 9/2013 |
| WO | 86/01533 A1 | 3/1986 |
| WO | 90/07861 A1 | 7/1990 |
| WO | 92/22653 A1 | 12/1992 |
| WO | 93/11161 A1 | 6/1993 |
| WO | 93/15210 A1 | 8/1993 |
| WO | 96/13583 A2 | 5/1996 |
| WO | 96/37621 A2 | 11/1996 |
| WO | 99/52552 A1 | 10/1999 |
| WO | 01/13937 A1 | 3/2001 |
| WO | 02/12535 A1 | 2/2002 |
| WO | 02/068601 A2 | 9/2002 |
| WO | 03/087319 A2 | 10/2003 |
| WO | 03/093315 A2 | 11/2003 |
| WO | 2004032857 A2 | 4/2004 |
| WO | 2007/063424 A2 | 6/2007 |
| WO | 2008/029271 A2 | 3/2008 |
| WO | 2009/141679 A2 | 11/2009 |
| WO | 2010/125571 A1 | 11/2010 |
| WO | 2011010309 A1 | 1/2011 |
| WO | 2014/059251 A1 | 4/2014 |

OTHER PUBLICATIONS

Mariuzza et al. (Annu. Rev. Biophys. Biophys. Chem. 1987; 16: 139-159).*

McCarthy et al. (J. Immunol. Methods, 251(1-2): 137-149, 2001).*

Azuz-Lieberman et al., (2005) The involvement of NK cells in ankylosing spondylitis. Int Immunol 17(7): 837-45.

Cruse JM and Lewis RE (2003) "Illustrated Dictionary of Immunology", 2nd Ed., CRC Press, p. 42.

Gong et al., (2011) Diagnostic value of serum CEACAM1 in patients with pancreatic cancer. J South Med Univ 31: 164-166. English abstract.

Khatib et al., (2011) Carcinoembryonic antigen cell adhesion molecule-1 (CEACAM1) in posterior uveal melanoma: correlation with clinical and histological survival markers. Invest Ophthalmol Vis Sci 52(13): 9368-9372.

Kromenaker and Srienc (1994) Stability of producer hybridoma cell lines after cell sorting: A case study. Biotechnology 10(3): 299-307.

Markel et al., (2010) Systemic dysregulation of CEACAM1 in melanoma patients. Cancer Immunol Immunother 59(2): 215-230.

Roitt I.M., Brostoff J. & Male D. (1998) Immunology. 5th edition, 1998 Mosby International Ltd., London. pp. 129-131.

Albarran-Somoza et al., (2006) CEACAM1 in cervical cancer and precursor lesions: association with human papillomavirus infection. J Histochem Cytochem 54(12): 1393-9.

Balmaña et al., (2009) BRCA in breast cancer: ESMO clinical recommendations. Ann Oncol 20 (Suppl 4): 19-20.

Besser et al., (2009) Minimally cultured or selected autologous tumor-infiltrating lymphocytes after a lympho-depleting chemotherapy regimen in metastatic melanoma patients. J Immunother 32(4): 415-423.

Besser et al., (2010) Clinical responses in a phase II study using adoptive transfer of short-term cultured tumor infiltration lymphocytes in metastatic melanoma patients. Clin Cancer Res 16(9): 2646-2655.

Bird et al., (1988) Single-chain antigen-binding proteins. Science 242(4877): 423-6.

Boerner et al., (1991) Production of antigen-specific human monoclonal antibodies from in vitro-primed human splenocytes. J Immunol 147(1): 86-95.

Brand et al., (2006) Prospect for anti-HER2 receptor therapy in breast cancer. Anticancer Res 26(1B): 463-470.

Brennan et al., (1985) Preparation of bispecific antibodies by chemical recombination of monoclonal immunoglobulin G1 fragments. Science 229(4708): 81-3.

Brüggemann et al., (1993) Designer mice: the production of human antibody repertoires in transgenic animals. Year Immunol 7: 33-40.

Carter et al., (1992) High level *Escherichia coli* expression and production of a bivalent humanized antibody fragment. Biotechnology (N Y) 10(2):163-7.

Carter et al., (1992) Humanization of an anti-p185HER2 antibody for human cancer therapy. Proc Natl Acad Sci U S A 89(10): 4285-9.

Chothia and Lesk (1987) Canonical structures for the hypervariable regions of immunoglobulins. J Mol Biol 196(4): 901-17.

Clackson et al., (1991) Making antibody fragments using phage display libraries. Nature 352(6336): 624-8.

Clark (1997) IgG effector mechanisms. Chem Immunol 65: 88-110.

Douillard et al., (2000) Irinotecan combined with fluorouracil compared with fluorouracil alone as first-line treatment for metastatic colorectal cancer: a multicentre randomised trial. Lancet 355(9209): 1041-7.

Duchosal et al., (1992) Immunization of hu-PBL-SCID mice and the rescue of human monoclonal Fab fragments through combinatorial libraries. Nature 355(6357): 258-62.

Duffy (2001) Carcinoembryonic antigen as a marker for colorectal cancer: is it clinically useful? Clin Chem 47(4): 624-30.

Fishwild et al., (1996) High-avidity human IgG kappa monoclonal antibodies from a novel strain of minilocus transgenic mice. Nat Biotechnol 14(7): 845-51.

Gray-Owen and Blumberg (2006) CEACAM1: contact-dependent control of immunity. Nat Rev Immunol 6(6): 433-46.

Holliger et al., (1993) "Diabodies": small bivalent and bispecific antibody fragments. Proc Natl Acad Sci U S A 90(14): 6444-8.

Hoogenboom and Winter (1992) By-passing immunisation. Human antibodies from synthetic repertoires of germline VH gene segments rearranged in vitro. J Mol Biol 227(2): 381-8.

(56) References Cited

OTHER PUBLICATIONS

Hussain et al., (1995) Selective increases in antibody isotypes and immunoglobulin G subclass responses to secreted antigens in tuberculosis patients and healthy household contacts of the patients. Clin Diagn Lab Immunol 2(6): 726-32.
Huston et al., (1988) Protein engineering of antibody binding sites: recovery of specific activity in an anti-digoxin single-chain Fv analogue produced in *Escherichia coli*. Proc Natl Acad Sci U S A 85(16): 5879-83.
Inbar et al., (1972) Localization of antibody-combining sites within the variable portions of heavy and light chains. Proc Natl Acad Sci USA 69(9): 2659-6262.
Jakobovits et al., (1993) Analysis of homozygous mutant chimeric mice: deletion of the immunoglobulin heavy-chain joining region blocks B-cell development and antibody production. Proc Natl Acad Sci U S A 90(6): 2551-5.
Jakobovits et al., (1993) Germ-line transmission and expression of a human-derived yeast artificial chromosome. Nature 362(6417): 255-8.
Jones et al., (1986) Replacing the complementarity-determining regions in a human antibody with those from a mouse. Nature 321(6069): 522-5.
Kammerer et al., (2004) The tumour suppressor gene CEACAM1 is completely but reversibly downregulated in renal cell carcinoma. J Pathol 204(3): 258-267.
Kataja et al., (2009) Primary breast cancer: ESMO clinical recommendations for diagnosis, treatment and follow-up. Ann Oncol 20(Suppl 4): iv10-4.
Kim et al., (2005) Antibody engineering for the development of therapeutic antibodies. Mol Cells 20(1): 17-29.
Köhler (1980) Immunoglobulin chain loss in hybridoma lines. Proc Natl Acad Sci U S A 77(4): 2197-2199.
Köhler and Milstein (1975) Continuous cultures of fused cells secreting antibody of predefined specificity. Nature 256 (5517): 495-7.
Kozbor and Roder (1983) The production of monoclonal antibodies from human lymphocytes. Immunology Today 4(3): 72-79.
Laack et al., (2002) Expression of CEACAM1 in adenocarcinoma of the lung: a factor of independent prognostic significance. J Clin Oncol 20(21): 4279-84.
Larrick and Fry (1991) PCR amplification of antibody genes. Methods 2(2): 106-110.
Lefranc et al., (1999) IMGT, the international ImMunoGeneTics database. Nucleic Acids Res 27(1): 209-12.
Liersch et al., (2005) Phase II trial of carcinoembryonic antigen radioimmunotherapy with 131I-labetuzumab after salvage resection of colorectal metastases in the liver: five-year safety and efficacy results. J Clin Oncol 23(27): 6763-70.
Lonberg and Huszar (1995) Human antibodies from transgenic mice. Int Rev Immunol 13(1): 65-93.
Lonberg et al., (1994) Antigen-specific human antibodies from mice comprising four distinct genetic modifications. Nature 368(6474): 856-9.
Markel et al., (2002) CD66a interactions between human melanoma and NK cells: a novel class I MHC-independent inhibitory mechanism of cytotoxicity. J Immunol 168(6): 2803-10.
Markel et al., (2002) Pivotal role of CEACAM1 protein in the inhibition of activated decidual lymphocyte functions. J Clin Invest 110(7): 943-53.
Markel et al., (2004) Biological function of the soluble CEACAM1 protein and implications in TAP2-deficient patients. Eur J Immunol 34(8): 2138-2148.
Markel et al., (2004) The critical role of residues 43R and 44Q of carcinoembryonic antigen cell adhesion molecules-1 in the protection from killing by human NK cells. J Immunol 173(6): 3732-9.
Markel et al., (2004) The mechanisms controlling NK cell autoreactivity in TAP2-deficient patients. Blood 103(5): 1770-1778.
Markel et al., (2006) Inhibition of human tumor-infiltrating lymphocyte effector functions by the homophilic carcinoembryonic cell adhesion molecule 1 interactions. J Immunol 177(9): 6062-71.
Markel et al., (2009) Dynamic expression of protective CEACAM1 on melanoma cells during specific immune attack. Immunology 126(2): 186-200.
Marks et al., (1991) By-passing immunization. Human antibodies from V-gene libraries displayed on phage. J Mol Biol 222(3): 581-97.
Marks et al., (1992) By-passing immunization: building high affinity human antibodies by chain shuffling. Biotechnology (N Y) 10(7): 779-83.
McCafferty et al., (1990) Phage antibodies: filamentous phage displaying antibody variable domains. Nature 348 (6301): 552-4.
Morales et al., (1999) Regulation of human intestinal intraepithelial lymphocyte cytolytic function by biliary glycoprotein (CD66a). J Immunol 163(3): 1363-70.
Culic et al., (1992) Molecular cloning and expression of a new rat liver cell-CAM105 isoform. Biochem J 285: 47-53.
Hansen et al., (1993) Characterization of second-generation monoclonal antibodies against carcinoembryonic antigen. Cancer 71(11): 3478-3485.
Jin et al., (2008) The research progress of carcino-embryonic antigen related cellular adhesion molecule 1. China Oncology 18(4) 310-314 Translated abstract.
Oikawa et al., (1992) Homotypic and heterotypic Ca++-independent cell adhesion activities of biliary glycoprotein, a member of carcinoembryonic antigen family, expressed on Cho cell surface. Biochemical and Biophysical Research Communications 186(2): 881-887.
Primus et al., (1983) Immunological heterogeneity of carcinoembryonic antigen: antigenic determinants on carcinoembryonic antigen distinguished by monoclonal antibodies. Cancer Research 43: 686-692.
Cianfriglia et al., "CEACAM1 is a Privileged Cell Surface Antigen to Design Novel ScFv Mediated-Immunotherapies of Melanoma, Lung Cancer and Other Types of Tumors", The Open Pharmacology Journal, 2012, 6, 1-11.
Makire et al., "Generation, Immunologic Characterization and Antitumor Effects of Human Monoclonal Antibodies for Carcinoembryonic Antigen", Int. J. Cancer, 108, 564-570 (2004).
Schildbach et al., (1993) Modulation of antibody affinity by a non-contact residue, Protein Science, 2, 206-214.
Bartolazzi et al., (2008) Galectin-3-expression analysis in the surgical selection of follicular thyroid nodules with indeterminate fine-needle aspiration cytology: a prospective multicentre study. The lancet oncology, 9(6), 543-549.
Morimoto and Inouye (1992) Single-step purification of F(ab')2 fragments of mouse monoclonal antibodies (immunoglobulins G1) by hydrophobic interaction high performance liquid chromatography using TSKgel Phenyl-5PW. J Biochem Biophys Methods 24(1-2): 107-17.
Morrison (1994) Immunology. Success in specification. Nature 368(6474): 812-3.
Morrison et al., (1984) Chimeric human antibody molecules: mouse antigen-binding domains with human constant region domains. Proc Natl Acad Sci U S A 81(21): 6851-5.
Müller et al., (1998) A dimeric bispecific miniantibody combines two specificities with avidity. FEBS Lett 432(1-2): 45-9.
Nelson et al., (2009) Screening for breast cancer: an update for the U.S. Preventive Services Task Force. Ann Intern Med 151(10): 727-737.
Neuberger (1996) Generating high-avidity human Mabs in mice. Nat Biotechnol 14(7): 826.
Ozturk and Palsson (1990) Loss of antibody productivity during long-term cultivation of a hybridoma cell line in low serum and serum-free media. Hybridoma 9(2): 167-175.
Pack et al., (1993) Improved bivalent miniantibodies, with identical avidity as whole antibodies, produced by high cell density fermentation of *Escherichia coli*. BioTechnology (N Y) 11(11): 1271-1277.
Pavoni et al., (2006) Selection, affinity maturation, and characterization of a human scFv antibody against CEA protein. BMC Cancer 6: 41.
Porter (1959) The hydrolysis of rabbit y-globulin and antibodies with crystalline papain. Biochem J 73: 119-126.

(56) References Cited

OTHER PUBLICATIONS

Presta (1992) Antibody engineering. Current Opinion in Structural Biology 2(4): 593-596.
Presta et al., (1993) Humanization of an antibody directed against IgE. J Immunol 151(5): 2623-32.
Presta et al., (1997) Humanization of an anti-vascular endothelial growth factor monoclonal antibody for the therapy of solid tumors and other disorders. Cancer Res 57(20): 4593-9.
Riechmann et al., (1988) Reshaping human antibodies for therapy. Nature 332(6162): 323-7.
Roder, John C. et al., (1985) Recent advances in the ebv-hybridoma technique. In: Monoclonal antibodies and cancer therapy. Journal of Cellular Biochemistry Supplement: UCLA Symposia on Molecular & Cellular Biology 29(9A): 33-74 abstract #0106.
Roitt I.M., Brostoff J. & Male D. (1998) Immunology. 5th edition, 1998 Mosby International Ltd., London. p. 80.
Rudikoff et al., (1982) Single amino acid substitution altering antigen-binding specificity. Proc Natl Acad Sci U S A 79 (6): 1979-1983.
Saltz et al., (1999) Weekly irinotecan (CPT-11), leucovorin (LV), and fluorouracil (FU) is superior to daily x5 LV/FU in patients (pts) with previously untreated metastatic colorectal cancer. Proc Am Soc Clin Oncol 18: 233a.
Sheets et al., (1998) Efficient construction of a large nonimmune phage antibody library: the production of high-affinity human single-chain antibodies to protein antigens. Proc Natl Acad Sci U S A 95(11): 6157-62.
Sienel et al., (2003) Elevated expression of carcinoembryonic antigen-related cell adhesion molecule 1 promotes progression of non-small cell lung cancer. Clin Cancer Res 9(6): 2260-6.
Sims et al., (1993) A humanized CD18 antibody can block function without cell destruction. J Immunol 151(4): 2296-308.
Slootstra et al., (1996) Structural aspects of antibody-antigen interaction revealed through small random peptide libraries. Mol Divers 1(2): 87-96.
Stern et al., (2005) Carcinoembryonic antigen (CEA) inhibits NK killing via interaction with CEA-related cell adhesion molecule 1. J Immunol 174(11): 6692-701.
Thies et al., (2002) CEACAM1 expression in cutaneous malignant melanoma predicts the development of metastatic disease. J Clin Oncol 20(10): 2530-2536.
Thompson et al., (1991) Carcinoembryonic antigen gene family: molecular biology and clinical perspectives. J Clin Lab Anal 5(5): 344-66.
Timmerman et al., (2007) Functional reconstruction and synthetic mimicry of a conformational epitope using CLIPS technology. J Mol Recognit 20(5): 283-99.
Vaughan et al., (1996) Human antibodies with sub-nanomolar affinities isolated from a large non-immunized phage display library. Nat Biotechnol 14(3): 309-14.
Verhoeyen et al., (1988) Reshaping human antibodies: grafting an antilysozyme activity. Science 239(4847): 1534-6.
Ward et al., (1989) Binding activities of a repertoire of single immunoglobulin variable domains secreted from *Escherichia coli*. Nature 341(6242): 544-6.
Watt et al., (2001) Homophilic adhesion of human CEACAM1 involves N-terminal domain interactions: structural analysis of the binding site. Blood 98(5): 1469-79.
Whitlow and Filpula (1991) Single-chain Fv proteins and their fusion proteins. Methods 2(2): 97-105.
Wu and Kabat (1970) An analysis of the sequences of the variable regions of Bence Jones proteins and myeloma light chains and their implications for antibody complementarity. J Exp Med 132(2): 211-50.
Ychou et al., (2008) Adjuvant radioimmunotherapy trial with iodine-131-labeled anti-carcinoembryonic antigen monoclonal antibody F6 F(ab')2 after resection of liver metastases from colorectal cancer. Clin Cancer Res 14(11): 3487-93.
Zapata et al., (1995) Engineering linear F(ab')2 fragments for efficient production in *Escherichia coli* and enhanced antiproliferative activity. Protein Eng 8(10): 1057-62.
Zheng et al., (2011) A novel anti-CEACAM5 monoclonal antibody, CC4, suppresses colorectal tumor growth and enhances NK cells-mediated tumor immunity. PLoS One 6(6): e21146.

* cited by examiner

SEQUENCE LISTING

<160> NUMBER OF SEQ ID NOS: 35

<210> SEQ ID NO 1
<211> LENGTH: 5
<212> TYPE: PRT

-continued

```
<213> ORGANISM: Mus musculus
<220> FEATURE:
<221> NAME/KEY: MISC_FEATURE
<222> LOCATION: (1)..(1)
<223> OTHER INFORMATION: X is Absent or Thr
<220> FEATURE:
<221> NAME/KEY: MISC_FEATURE
<222> LOCATION: (5)..(5)
<223> OTHER INFORMATION: X is Absent or Ile

<400> SEQUENCE: 1

Xaa Asn Asn Leu Xaa
1               5

<210> SEQ ID NO 2
<211> LENGTH: 8
<212> TYPE: PRT
<213> ORGANISM: Mus musculus

<400> SEQUENCE: 2

Ile Asn Pro Gly Ser Gly Asp Thr
1               5

<210> SEQ ID NO 3
<211> LENGTH: 11
<212> TYPE: PRT
<213> ORGANISM: Mus musculus

<400> SEQUENCE: 3

Gly Asp Tyr Tyr Gly Gly Phe Ala Val Asp Tyr
1               5                   10

<210> SEQ ID NO 4
<211> LENGTH: 6
<212> TYPE: PRT
<213> ORGANISM: Mus musculus

<400> SEQUENCE: 4

Gln Asp Ile Gly Asn Tyr
1               5

<210> SEQ ID NO 5
<211> LENGTH: 4
<212> TYPE: PRT
<213> ORGANISM: Mus musculus

<400> SEQUENCE: 5

Tyr Thr Ser Arg
1

<210> SEQ ID NO 6
<211> LENGTH: 7
<212> TYPE: PRT
<213> ORGANISM: Mus musculus

<400> SEQUENCE: 6

Gln Gln Gly Lys Ser Leu Pro
1               5

<210> SEQ ID NO 7
<211> LENGTH: 5
<212> TYPE: PRT
<213> ORGANISM: Mus musculus

<400> SEQUENCE: 7

Asn Asn Leu Ile Glu
```

```
<210> SEQ ID NO 8
<211> LENGTH: 17
<212> TYPE: PRT
<213> ORGANISM: Mus musculus

<400> SEQUENCE: 8

Val Ile Asn Pro Gly Ser Gly Asp Thr Asn Tyr Asn Glu Lys Phe Lys
1               5                   10                  15
Gly

<210> SEQ ID NO 9
<211> LENGTH: 11
<212> TYPE: PRT
<213> ORGANISM: Mus musculus

<400> SEQUENCE: 9

Gly Asp Tyr Tyr Gly Gly Phe Ala Val Asp Tyr
1               5                   10

<210> SEQ ID NO 10
<211> LENGTH: 11
<212> TYPE: PRT
<213> ORGANISM: Mus musculus

<400> SEQUENCE: 10

Arg Thr Ser Gln Asp Ile Gly Asn Tyr Leu Asn
1               5                   10

<210> SEQ ID NO 11
<211> LENGTH: 7
<212> TYPE: PRT
<213> ORGANISM: Mus musculus

<400> SEQUENCE: 11

Tyr Thr Ser Arg Leu His Ser
1               5

<210> SEQ ID NO 12
<211> LENGTH: 7
<212> TYPE: PRT
<213> ORGANISM: Mus musculus

<400> SEQUENCE: 12

Gln Gln Gly Lys Ser Leu Pro
1               5

<210> SEQ ID NO 13
<211> LENGTH: 8
<212> TYPE: PRT
<213> ORGANISM: Mus musculus

<400> SEQUENCE: 13

Gly Tyr Ala Phe Thr Asn Asn Leu
1               5

<210> SEQ ID NO 14
<211> LENGTH: 8
<212> TYPE: PRT
<213> ORGANISM: Mus musculus

<400> SEQUENCE: 14

Ile Asn Pro Gly Ser Gly Asp Thr
```

```
1               5

<210> SEQ ID NO 15
<211> LENGTH: 13
<212> TYPE: PRT
<213> ORGANISM: Mus musculus

<400> SEQUENCE: 15

Ala Arg Gly Asp Tyr Tyr Gly Gly Phe Ala Val Asp Tyr
1               5                   10

<210> SEQ ID NO 16
<211> LENGTH: 6
<212> TYPE: PRT
<213> ORGANISM: Mus musculus

<400> SEQUENCE: 16

Gln Asp Ile Gly Asn Tyr
1               5

<210> SEQ ID NO 17
<211> LENGTH: 4
<212> TYPE: PRT
<213> ORGANISM: Mus musculus

<400> SEQUENCE: 17

Tyr Thr Ser Arg
1

<210> SEQ ID NO 18
<211> LENGTH: 9
<212> TYPE: PRT
<213> ORGANISM: Mus musculus

<400> SEQUENCE: 18

Gln Gln Gly Lys Ser Leu Pro Arg Thr
1               5

<210> SEQ ID NO 19
<211> LENGTH: 10
<212> TYPE: PRT
<213> ORGANISM: Mus musculus

<400> SEQUENCE: 19

Gly Tyr Ala Phe Thr Asn Asn Leu Ile Glu
1               5                   10

<210> SEQ ID NO 20
<211> LENGTH: 17
<212> TYPE: PRT
<213> ORGANISM: Mus musculus

<400> SEQUENCE: 20

Val Ile Asn Pro Gly Ser Gly Asp Thr Asn Tyr Asn Glu Lys Phe Lys
1               5                   10                  15

Gly

<210> SEQ ID NO 21
<211> LENGTH: 13
<212> TYPE: PRT
<213> ORGANISM: Mus musculus

<400> SEQUENCE: 21

Ala Arg Gly Asp Tyr Tyr Gly Gly Phe Ala Val Asp Tyr
```

-continued

<210> SEQ ID NO 22
<211> LENGTH: 11
<212> TYPE: PRT
<213> ORGANISM: Mus musculus

<400> SEQUENCE: 22

Arg Thr Ser Gln Asp Ile Gly Asn Tyr Leu Asn
1               5                   10

<210> SEQ ID NO 23
<211> LENGTH: 7
<212> TYPE: PRT
<213> ORGANISM: Mus musculus

<400> SEQUENCE: 23

Tyr Thr Ser Arg Leu His Ser
1               5

<210> SEQ ID NO 24
<211> LENGTH: 9
<212> TYPE: PRT
<213> ORGANISM: Mus musculus

<400> SEQUENCE: 24

Gln Gln Gly Lys Ser Leu Pro Arg Thr
1               5

<210> SEQ ID NO 25
<211> LENGTH: 467
<212> TYPE: DNA
<213> ORGANISM: artificial sequence
<220> FEATURE:
<223> OTHER INFORMATION: Recombinant DNA

<400> SEQUENCE: 25
atgggatgga ccttggtctt tctctttctc ctgtcagtaa ctgcaggtgt tcactcccag      60
gtccagctgc agcagtctgg agctgagctg gtaaggcctg ggacttcagt gaaggtgtcc     120
tgcaaggctt ctggatacgc cttcactaat aacttgatag agtgggtaaa acagaggcct     180
ggacagggcc ttgagtggat tggagtgatt aatcctggaa gtggtgatac taactacaat     240
gagaagttca aggcaaggc aacactgact gcagacaaat cctccaacac tgcctacatg      300
cagctcagca gcctgacatc tgatgactct gcggtctatt tctgtgcaag aggggattac     360
tacggtggct ttgctgtgga ctactggggt caaggaacct cagtcaccgt ctcctcagcc     420
aaaacgacac cccatccgt ttatcccttg gcccctggaa gcttggg                    467

<210> SEQ ID NO 26
<211> LENGTH: 120
<212> TYPE: PRT
<213> ORGANISM: artificial sequence
<220> FEATURE:
<223> OTHER INFORMATION: Recombinant polypeptide

<400> SEQUENCE: 26

Gln Val Gln Leu Gln Gln Ser Gly Ala Glu Leu Val Arg Pro Gly Thr
1               5                   10                  15

Ser Val Lys Val Ser Cys Lys Ala Ser Gly Tyr Ala Phe Thr Asn Asn
                20                  25                  30

Leu Ile Glu Trp Val Lys Gln Arg Pro Gly Gln Gly Leu Glu Trp Ile
        35                  40                  45

```
Gly Val Ile Asn Pro Gly Ser Gly Asp Thr Asn Tyr Asn Glu Lys Phe
        50                  55                  60

Lys Gly Lys Ala Thr Leu Thr Ala Asp Lys Ser Ser Asn Thr Ala Tyr
 65                  70                  75                  80

Met Gln Leu Ser Ser Leu Thr Ser Asp Asp Ser Ala Val Tyr Phe Cys
                85                  90                  95

Ala Arg Gly Asp Tyr Tyr Gly Gly Phe Ala Val Asp Tyr Trp Gly Gln
            100                 105                 110

Gly Thr Ser Val Thr Val Ser Ser
            115                 120
```

<210> SEQ ID NO 27
<211> LENGTH: 488
<212> TYPE: DNA
<213> ORGANISM: artificial sequence
<220> FEATURE:
<223> OTHER INFORMATION: Recombinant DNA

<400> SEQUENCE: 27

```
atggtgtcct cagctcagtt ccttggtctc ctgttgctct gttttcaagg aaccagatgt      60
gatatccaga tgacacagac tacatcctcc ctgtctgcct ctctgggaga cagagtcacc     120
atcagttgca ggacaagtca ggacattggc aattatttaa actggtatca gcagaaacca     180
gatggaactg ttaaactcct gatctactac acatcaagat acactcagg agtcccatca      240
aggttcagtg gcagtgggtc tggaacagat tattctctca ccattagcaa cctggagcaa     300
gaagatattg ccacttactt ttgccaacag ggtaaaagcc ttcctcggac gttcggtgga     360
ggcaccaagt tggaaatcaa acgggctgat gctgcaccaa ctgtatccat cttcccacca     420
tccagtgagc agttaacatc tggaggtgcc tcagtcgtgt gcttcttgaa caacttctac     480
cccagaga                                                              488
```

<210> SEQ ID NO 28
<211> LENGTH: 107
<212> TYPE: PRT
<213> ORGANISM: artificial sequence
<220> FEATURE:
<223> OTHER INFORMATION: Recombinant polypeptide

<400> SEQUENCE: 28

```
Asp Ile Gln Met Thr Gln Thr Thr Ser Ser Leu Ser Ala Ser Leu Gly
 1               5                  10                  15

Asp Arg Val Thr Ile Ser Cys Arg Thr Ser Gln Asp Ile Gly Asn Tyr
            20                  25                  30

Leu Asn Trp Tyr Gln Gln Lys Pro Asp Gly Thr Val Lys Leu Leu Ile
        35                  40                  45

Tyr Tyr Thr Ser Arg Leu His Ser Gly Val Pro Ser Arg Phe Ser Gly
 50                  55                  60

Ser Gly Ser Gly Thr Asp Tyr Ser Leu Thr Ile Ser Asn Leu Glu Gln
 65                  70                  75                  80

Glu Asp Ile Ala Thr Tyr Phe Cys Gln Gln Gly Lys Ser Leu Pro Arg
                85                  90                  95

Thr Phe Gly Gly Gly Thr Lys Leu Glu Ile Lys
            100                 105
```

<210> SEQ ID NO 29
<211> LENGTH: 10
<212> TYPE: PRT

<213> ORGANISM: artificial sequence
<220> FEATURE:
<223> OTHER INFORMATION: Recombinant peptide

<400> SEQUENCE: 29

```
Asp Ile Gln Met Thr Gln Thr Thr Ser Ser
1               5                   10
```

<210> SEQ ID NO 30
<211> LENGTH: 450
<212> TYPE: PRT
<213> ORGANISM: artificial sequence
<220> FEATURE:
<223> OTHER INFORMATION: Recombinant polypeptide

<400> SEQUENCE: 30

```
Gln Val Gln Leu Gln Gln Ser Gly Ala Glu Leu Val Arg Pro Gly Thr
1               5                   10                  15

Ser Val Lys Val Ser Cys Lys Ala Ser Gly Tyr Ala Phe Thr Asn Asn
                20                  25                  30

Leu Ile Glu Trp Val Lys Gln Arg Pro Gly Gln Gly Leu Glu Trp Ile
            35                  40                  45

Gly Val Ile Asn Pro Gly Ser Gly Asp Thr Asn Tyr Asn Glu Lys Phe
50                  55                  60

Lys Gly Lys Ala Thr Leu Thr Ala Asp Lys Ser Ser Asn Thr Ala Tyr
65                  70                  75                  80

Met Gln Leu Ser Ser Leu Thr Ser Asp Asp Ser Ala Val Tyr Phe Cys
                85                  90                  95

Ala Arg Gly Asp Tyr Tyr Gly Gly Phe Ala Val Asp Tyr Trp Gly Gln
            100                 105                 110

Gly Thr Ser Val Thr Val Ser Ser Ala Ser Thr Lys Gly Pro Ser Val
        115                 120                 125

Phe Pro Leu Ala Pro Ser Ser Lys Ser Thr Ser Gly Gly Thr Ala Ala
130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Ser Leu Gly Thr Gln Thr Tyr Ile Cys Asn Val Asn His Lys
        195                 200                 205

Pro Ser Asn Thr Lys Val Asp Lys Lys Val Glu Pro Lys Ser Cys Asp
210                 215                 220

Lys Thr His Thr Cys Pro Pro Cys Pro Ala Pro Glu Leu Leu Gly Gly
225                 230                 235                 240

Pro Ser Val Phe Leu Phe Pro Pro Lys Pro Lys Asp Thr Leu Met Ile
                245                 250                 255

Ser Arg Thr Pro Glu Val Thr Cys Val Val Val Asp Val Ser His Glu
            260                 265                 270

Asp Pro Glu Val Lys Phe Asn Trp Tyr Val Asp Gly Val Glu Val His
        275                 280                 285

Asn Ala Lys Thr Lys Pro Arg Glu Glu Gln Tyr Asn Ser Thr Tyr Arg
290                 295                 300

Val Val Ser Val Leu Thr Val Leu His Gln Asp Trp Leu Asn Gly Lys
305                 310                 315                 320
```

Glu Tyr Lys Cys Lys Val Ser Asn Lys Ala Leu Pro Ala Pro Ile Glu
                        325                 330                 335

Lys Thr Ile Ser Lys Ala Lys Gly Gln Pro Arg Glu Pro Gln Val Tyr
            340                 345                 350

Thr Leu Pro Pro Ser Arg Asp Glu Leu Thr Lys Asn Gln Val Ser Leu
        355                 360                 365

Thr Cys Leu Val Lys Gly Phe Tyr Pro Ser Asp Ile Ala Val Glu Trp
370                 375                 380

Glu Ser Asn Gly Gln Pro Glu Asn Asn Tyr Lys Thr Thr Pro Pro Val
385                 390                 395                 400

Leu Asp Ser Asp Gly Ser Phe Phe Leu Tyr Ser Lys Leu Thr Val Asp
                405                 410                 415

Lys Ser Arg Trp Gln Gln Gly Asn Val Phe Ser Cys Ser Val Met His
            420                 425                 430

Glu Ala Leu His Asn His Tyr Thr Gln Lys Ser Leu Ser Leu Ser Pro
        435                 440                 445

Gly Lys
    450

<210> SEQ ID NO 31
<211> LENGTH: 214
<212> TYPE: PRT
<213> ORGANISM: artificial sequence
<220> FEATURE:
<223> OTHER INFORMATION: Recombinant polypeptide

<400> SEQUENCE: 31

Asp Ile Gln Met Thr Gln Thr Thr Ser Ser Leu Ser Ala Ser Leu Gly
1               5                   10                  15

Asp Arg Val Thr Ile Ser Cys Arg Thr Ser Gln Asp Ile Gly Asn Tyr
            20                  25                  30

Leu Asn Trp Tyr Gln Gln Lys Pro Asp Gly Thr Val Lys Leu Leu Ile
        35                  40                  45

Tyr Tyr Thr Ser Arg Leu His Ser Gly Val Pro Ser Arg Phe Ser Gly
    50                  55                  60

Ser Gly Ser Gly Thr Asp Tyr Ser Leu Thr Ile Ser Asn Leu Glu Gln
65                  70                  75                  80

Glu Asp Ile Ala Thr Tyr Phe Cys Gln Gln Gly Lys Ser Leu Pro Arg
                85                  90                  95

Thr Phe Gly Gly Gly Thr Lys Leu Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210

```
<210> SEQ ID NO 32
<211> LENGTH: 13
<212> TYPE: PRT
<213> ORGANISM: Homo sapiens

<400> SEQUENCE: 32

Val Leu Leu Leu Val His Asn Leu Pro Gln Gln Leu Phe
1               5                   10

<210> SEQ ID NO 33
<211> LENGTH: 12
<212> TYPE: PRT
<213> ORGANISM: Homo sapiens

<400> SEQUENCE: 33

Tyr Pro Asn Ala Ser Leu Leu Ile Gln Asn Val Thr
1               5                   10

<210> SEQ ID NO 34
<211> LENGTH: 7
<212> TYPE: PRT
<213> ORGANISM: Homo sapiens

<400> SEQUENCE: 34

Pro Asn Ala Ser Leu Leu Ile
1               5

<210> SEQ ID NO 35
<211> LENGTH: 108
<212> TYPE: PRT
<213> ORGANISM: Homo sapiens

<400> SEQUENCE: 35

Gln Leu Thr Thr Glu Ser Met Pro Phe Asn Val Ala Glu Gly Lys Glu
1               5                   10                  15

Val Leu Leu Leu Val His Asn Leu Pro Gln Gln Leu Phe Gly Tyr Ser
            20                  25                  30

Trp Tyr Lys Gly Glu Arg Val Asp Gly Asn Arg Gln Ile Val Gly Tyr
        35                  40                  45

Ala Ile Gly Thr Gln Gln Ala Thr Pro Gly Pro Ala Asn Ser Gly Arg
    50                  55                  60

Glu Thr Ile Tyr Pro Asn Ala Ser Leu Leu Ile Gln Asn Val Thr Gln
65                  70                  75                  80

Asn Asp Thr Gly Phe Tyr Thr Leu Gln Val Ile Lys Ser Asp Leu Val
                85                  90                  95

Asn Glu Glu Ala Thr Gly Gln Phe His Val Tyr Pro
            100                 105
```

ANTIBODIES TO CARCINOEMBRYONIC ANTIGEN-RELATED CELL ADHESION MOLECULE (CEACAM)

CROSS REFERENCE TO RELATED APPLICATION(S)

This application is a 35 U.S.C. §371 National Phase Entry Application from PCT/IL2012/050402 filed Oct. 10, 2012, and also claims foreign priority to PCT Application No. PCT/IL2011/000808 filed Oct. 11, 2011, the disclosures of which are incorporated herein by reference.

FIELD OF THE INVENTION

The present invention relates to therapeutic and diagnostic antibodies, useful in diseases involving Carcinoembryonic Antigen-Related Cell Adhesion Molecule (CEACAM), expression, activation or function. In particular, the present invention provides antibodies having specific complementarity determining regions (CDRs) and improved properties over other antibodies which recognize CEACAM1.

BACKGROUND OF THE INVENTION

The transmembrane protein Carcinoembryonic antigen-related cell adhesion molecule 1 (CEACAM1, also known as biliary glycoprotein (BGP), CD66a and C-CAM1), is a member of the carcinoembryonic antigen family (CEA) that also belongs to the immunoglobulin superfamily. CEACAM1 interacts with other known CEACAM proteins, including CD66a (CEACAM1), CD66e (CEACAM6) and CD66e (CEACAM5, CEA) proteins. It is expressed on a wide spectrum of cells, ranging from epithelial cells to those of hemopoietic origin (e.g. immune cells).

Many different functions have been attributed to the CEACAM1 protein. It was shown that the CEACAM1 protein is over expressed in some carcinomas of colon, prostate, as well as other types of cancer. Additional data support the central involvement of CEACAM1 in angiogenesis and metastasis. CEACAM1 also plays a role in the modulation of innate and adaptive immune responses. For example, CEACAM1 was shown to be an inhibitory receptor for activated T cells contained within the human intestinal epithelium (WO99/52552 and Morales et al. J. Immunol. 1999, 163, 1363-1370). Additional reports have indicated that CEACAM1 engagement either by T Cell Receptor cross-linking with Monoclonal antibodies (mAbs) or by *Neisseria gonorrhoeae* Opa proteins inhibits T cell activation and proliferation.

Melanoma is a malignancy of pigment-producing cells (melanocytes), responsible for 75% of skin cancer-related mortality worldwide, mainly due to extensive metastasis. Metastatic melanoma (MM) responds feebly to most anti-cancer regimens, and mean overall survival mean for patients with MM is 8.5 months. There is evidence that overexpression of CEACAM1 can be correlated with poor prognosis and is detected in the majority of metastatic melanoma cases. CEACAM1 is rarely expressed by normal melanocytes, but frequently found on melanoma cells. CEACAM1 expression on primary cutaneous melanoma lesions strongly predicts the development of metastatic disease with poor prognosis. Moreover, increased CEACAM1 expression was observed on NK cells derived from some patients with metastatic melanoma compared with healthy donors.

Evidence indicates that CEACAM1 may have an important role in virus infections. For example, Markel at el. (J. Clinical Investigation 2002, 110, 943-953) demonstrated that lymphocytes isolated from the deciduae of CMV-infected patients express the CEACAM1 protein in increased levels. The increased CEACAM1 expression on the decidual lymphocytes might diminish the local immune response and serve as another mechanism developed by the virus to avoid recognition and clearance primarily by activated decidual lymphocytes. Albarran-Somoza et al. (Journal of Histochemistry & Cytochemistry 2006, 54, 1393), who studied the protein expression pattern of CEACAM1 in cervical cancer and precursor lesions in the context of human papillomavirus (HPV) infection, showed that CEACAM1 immunostaining is significantly increased in high-grade squamous intraepithelial lesions (SIL) in comparison with low-grade SIL and normal cervical tissues. The authors suggested that CEACAM1 upregulation may be related to integration of HPV DNA in high-grade SIL and that CEACAM1 may be an important biological marker in SIL and cervical cancer progression. Altogether this evidence indicates that CEACAM1 plays an important role in various viral infections. In addition, CEACAM1 over expression may serve as marker of various viral infections.

WO2007/063424 and U.S. Patent Application No. 20070110668 disclose methods for regulating the immune system, and in particular methods for the regulation of a specific immune response, including the regulation of lymphocyte activity. These methods comprise both the negative and positive modulation of CEACAM1 protein function.

U.S. Patent Application No. 20070071758 teaches methods and compositions for enhancing the efficacy of tumor-infiltrating lymphocyte (TIL) therapy in the treatment of cancer by negatively modulating the activity of the CEACAM1 protein, such as for example, by using an immunoglobulin specific for CEACAM1.

U.S. Patent Application No. 20080108140 discloses methods of modulating specific immune responses to create a protective immunity in the treatment of autoimmune diseases and diseases requiring the transplantation of tissue. In particular, it relates to the suppression of immune responses in a targeted fashion, by increasing the functional concentration of the CEACAM1 protein in the target tissue.

U.S. Patent Application No. 20040047858 discloses specific antibodies which are capable of modulating T cell activity via CEACAM1 and uses thereof in treating immune response related diseases (e.g. graft versus host disease, autoimmune diseases, cancers etc.).

U.S. Patent Application Nos. 20020028203, 20050169922 and 20080102071 disclose compositions which bind T cell inhibitory receptor molecules and modulate (i.e. enhance or suppress) T cell activity (e.g. cytotoxicity and proliferation), such as biliary glycoprotein binding agents, and methods of using such compositions such as for treatment of diseases (e.g. an autoimmune disease, immunodeficiency, cancer etc.).

WO 2010/125571 to the present inventor discloses a murine monoclonal antibody produced by a specific hybridoma cell. The mAb is highly selective to CEACAM1 and does not cross-react with other members of the CEACAM family.

None of the known antibodies which recognize CEACAM1 have the spectrum of binding specificity of the monoclonal antibodies of the present invention. Thus, there is an unmet need to provide antibodies recognizing specific subsets of CEACAM proteins which can be used diagnostically and therapeutically in diseases involving CEACAM expression or activation.

SUMMARY OF THE INVENTION

The present invention discloses monoclonal antibodies which recognize a specific set of CEACAM subtypes. Advantageously, the antibodies of the invention show binding to CEACAM1 and at least one additional subtype selected from CEACAM5 and CEACAM3. The antibodies of the invention are characterized by having unique CDR sequence and framework combinations and by binding to newly identified epitopes within the CEACAM1 molecule. The unique specificity of the monoclonal antibodies of the present invention, broaden their therapeutic utility for treatment and diagnosis of additional types of malignancies and viral infections. The present invention also provides methods for identifying and isolating such antibodies, methods for their production, and therapeutic and diagnostic uses thereof.

The monoclonal antibodies according to the present invention have specific combinations of CDRs and possess unique properties and improved specificity and potency over known anti CEACAM1 antibodies.

According to one aspect, the present invention provides a monoclonal antibody which recognizes CEACAM1, or an antibody fragment thereof comprising at least an antigen-binding portion thereof, having heavy-chain CDRs comprising sequences set forth in SEQ ID NOs: 1, 2 and 3, and light-chain CDRs comprising sequences set forth in SEQ ID NOs: 4, 5 and 6, and analogs and derivatives thereof.

According to some embodiments a monoclonal antibody or antibody fragment which recognizes CEACAM1 is provided having a heavy-chain CDR1 comprising a sequence set forth in SEQ ID NO: 1, a heavy-chain CDR2 comprising a sequence set forth in SEQ ID NO: 2 a heavy-chain CDR3 comprising a sequence set forth in SEQ ID NO: 3, a light-chain CDR1 comprising a sequence set forth in SEQ ID NO: 4, a light-chain CDR2 comprising a sequence set forth in SEQ ID NO: 5 and a light-chain CDR3 comprising a sequence set forth in SEQ ID NO:6, and analogs and derivatives thereof.

According to some embodiments a monoclonal antibody which recognizes CEACAM1 or a fragment thereof comprising at least an antigen binding portion is provided, comprising heavy chain CDRs having the sequences set forth in SEQ ID NOs: 7, 8 and 9.

According to some embodiments a monoclonal antibody which recognizes CEACAM1 or a fragment thereof comprising at least an antigen binding portion is provided, comprising heavy chain CDRs having the sequences set forth in SEQ ID NOs: 13, 14 and 15.

According to some embodiments a monoclonal antibody which recognizes CEACAM1 or a fragment thereof comprising at least an antigen binding portion is provided, comprising light chain CDRs having the sequences set forth in SEQ ID NOs: 10, 11 and 12.

According to some embodiments a monoclonal antibody which recognizes CEACAM1 or a fragment thereof comprising at least an antigen binding portion is provided, wherein the light chain CDRs having the sequences set forth in SEQ ID NOs: 16, 17 and 18.

According to other embodiments a monoclonal antibody is provided having CDR sequences set forth in SEQ ID NOs: 13, 14, 15, 16, 17, and 18.

According to yet other embodiments, a monoclonal antibody is provided having CDR sequences set forth in SEQ ID NOs: 7, 8, 9, 10, 11, and 12.

Analogs and derivatives of the monoclonal antibody or fragment thereof, having at least 90% sequence identity with the antigen-binding portion of the reference sequence are also within the scope of the present invention.

According to some embodiments, analogs and derivatives of the monoclonal antibody or fragment thereof having at least 95% sequence identity with the antigen-binding portion of the reference sequence are provided. According to a specific embodiment the antibody comprises a heavy chain variable domain sequence having a sequence set forth in SEQ ID NO: 26: QVQLQQSGAELVRPGTSVKVSCKAS-GYAFTNNLIEWVKQRPGQGLEWIGVINPGSG DTNYNEKFKGKATLTADKSSNTAYMQLSS-LTSDDSAVYFCARGDYYGGFAVDYW GQGTSVTVSS, or an analog or derivative thereof having at least 97% sequence identity with the heavy chain sequence.

According to yet another embodiment the antibody comprises a light chain variable domain sequence having a sequence set forth in SEQ ID NO: 28: DIQMTQTTSSLSASLGDRVTISCRTSQDIGNYLNWY-QQKPDGTVKLLIYYTSRLHSG VPSRFSGSGSGTDYS-LTISNLEQEDIATYFCQQGKSLPRTFGGGTKLEIK, or an analog or derivative thereof having at least 97% sequence identity with the light chain sequence.

According to a specific embodiment the antibody or fragment thereof comprises a heavy chain variable domain having a sequence set forth in SEQ ID NO: 26 and a light chain variable domain having a sequence set forth in SEQ ID NO: 28, or an analog or derivative thereof having at least 97% sequence identity with the antibody or fragment sequence.

The present invention encompasses monoclonal antibodies isolated from hybridoma cells or other biological systems, as well as monoclonal antibodies produced recombinantly or synthetically. A monoclonal antibody according to the present invention may contain a constant region from any mammalian species, including but not limited to mouse, rat and human. A monoclonal antibody according to the present invention includes a chimeric antibody, a humanized antibody, a fully human antibody, a xenogeneic antibody, and an antibody fragment comprising at least the antigen-binding portion of an antibody. According to a specific embodiment the antibody fragment is selected from the group consisting of: Fab, Fab', F(ab')$_2$, Fd, Fd', Fv, dAb, isolated CDR region, single chain antibody, "diabodies", and "linear antibodies".

According to some particular embodiments the present invention provides a monoclonal antibody, or an antibody fragment comprising:
i. a framework sequence selected from the group consisting of: mouse IgG2a, mouse IgG2b, mouse IgG3, human IgG1, human IgG2, human IgG3; and
ii. a set of six CDRs having sequences set forth in SEQ ID NOs: 13, 14, 15, 16, 17, and 18; or a set of six CDRs having sequences set forth in SEQ ID NOs: 7, 8, 9, 10, 11, and 12; and analogs and derivatives thereof having at least 97% sequence identity with said CDR sequences, wherein the monoclonal antibody or fragment binds with an affinity of at least about $5 \times 10^{-7}$M to at least two CEACAM subtypes.

According to some embodiments, the monoclonal antibody or fragment thereof binds with an affinity of at least about $5 \times 10^{-7}$M to at least two CEACAM subtypes.

According to other embodiments, the monoclonal antibody or fragment thereof binds with an affinity of at least about $10^{-8}$M to CEACAM1.

According to some specific embodiments, the monoclonal antibody is a chimeric monoclonal antibody.

According to some embodiments, the chimeric antibody comprises human-derived constant regions.

According to some embodiments the human constant regions of the chimeric antibody are selected from the group consisting of: human IgG1, human IgG2, and human IgG3

According to a particular embodiment, a chimeric or humanized monoclonal antibody which recognizes CEACAM1 is provided comprising the six CDRs having sequences set forth in SEQ ID NOs: 13, 14, 15, 16, 17, and 18; or the six CDRs having sequences set forth in SEQ ID NOs: 7, 8, 9, 10, 11, and 12; and analogs and derivatives thereof having at least 95% sequence identity with said CDR sequences, and a constant region subclass selected from human IgG1, human IgG2 and human IgG3, wherein the monoclonal antibody binds with an affinity of at least about $5\times10^{-7}$M to at least two CEACAM subtypes.

According to a specific embodiment the chimeric or humanized monoclonal antibody or fragment thereof, comprises a constant region subclass of human IgG1 subtype.

According to another particular embodiment a chimeric monoclonal antibody or a fragment thereof comprising at least the antigen-binding portion, is provided comprising a heavy chain sequence set forth in SEQ ID NO: 30.

According to yet another particular embodiment a chimeric monoclonal antibody or a fragment thereof comprising at least the antigen-binding portion, is provided comprising a light chain sequence set forth in SEQ ID NO: 31.

According to yet another particular embodiment a chimeric monoclonal antibody or a fragment thereof comprising at least the antigen-binding portion, is provided having a heavy chain sequence set forth in SEQ ID NO: 30, and light chain sequence set forth in SEQ ID NO: 31.

According to a particular embodiment, a monoclonal antibody which recognizes CEACAM1 is provided produced from DNA sequences of the heavy and light chains contained in a plasmid deposited on Sep. 28, 2011 under ATCC Accession Number PTA-12130 in the American Type Culture Collection (ATCC®) located at 10801 University Blvd, Manassas, Va. 20110.

Monoclonal antibodies of the present invention exhibit according to some embodiments specific binding to more than one CEACAM subtype. According to some embodiments, the monoclonal antibody binds at least two different CEACAM subtypes. According to some specific embodiments the monoclonal antibody binds to CEACAM1 and at least one of CEACAM3 and CEACAM5. According to a particular embodiment the monoclonal antibody binds to CEACAM1 and CEACAM5. According to another particular embodiment the monoclonal antibody binds to CEACAM1 and CEACAM3. According to yet other embodiments, a monoclonal antibody according to the present invention binds to CEACAM subtypes 1, 3 and 5.

According to particular embodiments, a monoclonal antibody according to the present invention does not bind to CEACAM4 and CEACAM6.

According to yet another aspect the present invention provides a monoclonal antibody which recognizes CEACAM1, or a fragment thereof comprising at least the antigen-binding portion, which is capable of binding the same epitope on the CEACAM1 molecule to which a monoclonal antibody to CEACAM1 having a heavy chain sequence set forth in SEQ ID NO: 26 or SEQ ID NO: 30 and a light chain sequence set forth as SEQ ID NO: 28 or SEQ ID NO: 31, binds.

According to some embodiments, the monoclonal antibody is reactive with a epitope within residues 17-29 and 68-79 of human CEACAM1 having the sequences VLLL-VHNLPQQLF (SEQ ID NO:32) and YPNASLLIQNVT (SEQ ID NO:33) respectively.

According to some embodiments, the epitope on the CEACAM1 molecule to which the monoclonal antibody binds is an epitope comprising amino acid residues within the sequences VLLLVHNLPQQLF (SEQ ID NO: 32) and YPNASLLIQNVT (SEQ ID NO: 33).

According to other embodiments, the monoclonal antibody according to the invention binds an epitope comprising at least four amino acids of the sequence VLLLVHN-LPQQLF (SEQ ID NO: 32).

According to yet other embodiments, the monoclonal antibody according to the invention binds an epitope within sequences VLLLVHNLPQQLF (SEQ ID NO: 32) and PNASLLI (SEQ ID NO: 34).

According to some embodiments, the monoclonal antibody or fragment thereof binds to the same epitope of which an antibody having the six CDR sequences set forth in SEQ ID NOs: 7, 8, 9, 10, 11 and 12 binds.

According to yet other embodiments, the monoclonal antibody or fragment thereof binds to the same epitope of which an antibody having the CDR sequences set forth in SEQ ID NOs: 13, 14, 15, 16, 17 and 18 binds.

According to a particular embodiment, the monoclonal antibody or fragment thereof binds to the same epitope which is bound by an antibody produced from DNA sequences deposited on Sep. 28, 2011 under ATCC Accession Number PTA-12130.

The present invention provides, according to yet another aspect, an isolated peptide sequence of 6-20 amino acids comprising at least three amino acids from the sequence VLLLVHNLPQQLF (SEQ ID NO: 32) and at least three amino acids from the sequence YPNASLLIQNVT (SEQ ID NO: 33). Analogs and derivatives of said peptide, having at least 85%, 90%, 95% or 98% homology with the parent sequence are also within the scope of the present invention.

According to some embodiments, the isolated peptide comprises at least six amino acids from the sequence VLLL-VHNLPQQLF (SEQ ID NO: 32).

According to yet other embodiments, the isolated peptide comprises the amino acids of the sequences VLLLVHN-LPQQLF (SEQ ID NO: 32) and PNASLLI (SEQ ID NO: 34).

Use of the isolated peptides for production of monoclonal or polyclonal antibodies is also within the scope of the present invention as well as their use in diagnosis or treatment.

Within the scope of the present invention are also nucleic acid molecules encoding an antibody or antibody fragment according to the invention, having affinity and specificity for CEACAM1.

According to this aspect, an isolated polynucleotide sequence encoding an antibody which recognizes CEACAM1 or an antibody fragment thereof is disclosed.

According to some embodiments, the isolated polynucleotide sequence comprises a DNA sequence set forth in SEQ ID NO: 25 or analog thereof having at least 90% sequence identity with said DNA sequence. According to other embodiments, the isolated polynucleotide sequence comprises a DNA sequence set forth in SEQ ID NO: 27 or analog thereof having at least 90% sequence identity with said DNA sequence.

Plasmids comprising at least one polynucleotide sequence encoding a monoclonal antibody or fragment thereof according to the invention are also disclosed, as well as host cells comprising these plasmids.

According to a particular embodiment, a plasmid comprising polynucleotide sequences set forth in SEQ ID NOs: 25 and 27, deposited on Sep. 28, 2011 under ATCC Accession Number PTA-12130, is disclosed.

In another aspect the present invention is related to a pharmaceutical composition useful for preventing, attenuating or treating a disease or disorder associated with CEACAM1, CEACAM3 or CEACAM5 expression, activation or function. A pharmaceutical composition according to the invention comprises a therapeutically effective amount of a monoclonal antibody which recognizes CEACAM1, CEACAM3 or CEACAM5 or an antibody fragment thereof comprising at least an antigen-binding portion; and a pharmaceutically acceptable carrier.

According to some embodiments, the pharmaceutical composition comprises a monoclonal antibody capable of binding to CEACAM1 with a binding affinity of at least $10^{-8}$ kD.

According to additional embodiments, the pharmaceutical composition comprises a monoclonal antibody capable of binding with an affinity of at least about $10^{-8}$ kD to CEACAM1 and with affinity of at least about $5 \times 10^{-7}$M to at least one of CEACAM3 and CEACAM5.

According to a particular embodiment, the pharmaceutical composition comprises a monoclonal antibody capable of binding with an affinity of at least about $5 \times 10^{-7}$ kD to CEACAM1, CEACAM3 and CEACAM5.

According to certain embodiments the disease or disorder associated with CEACAM1, CEACAM3 and/or CEACAM5 expression, activation or function is a cell proliferative disease or disorder. According to some embodiments the cell proliferative disease or disorder is cancer.

According to some embodiments, the cancer associated with over-expression of CEACAM5 is selected from the group consisting of: gastrointestinal, colorectal (CRC) pancreatic non-small cell lung cancer (NSCL), breast, thyroid, stomach, ovarian and uterine.

According to a specific embodiment the cancers associated with over expression of CEACAM1 are melanoma, pancreatic cancer, all types of lung cancers and myeloma.

The pharmaceutical composition according to the present invention may be administered as a stand alone treatment or in addition to a treatment with any other therapeutic agent. According to a specific embodiment, antibodies according to the present invention are administered to a subject in need thereof as part of a treatment regimen in conjunction with at least one anti-cancer agent. The pharmaceutical composition according to the present invention may be administered together with the other agent or separately.

In another aspect the present invention provides diagnostic compositions useful for detecting at least one CEACAM subtype selected from the group consisting if: CEACAM1, CEACAM3 and CEACAM5, in a subject. A diagnostic composition according to the invention comprises a therapeutically effective amount of a monoclonal antibody having affinity of at least about $5 \times 10^{-7}$ M to CEACAM1, CEACAM3 or CEACAM5 or an antibody fragment thereof comprising at least an antigen-binding portion; and an optional carrier or excipient.

In yet another aspect the present invention is related to a method of preventing, attenuating or treating a disease or disorder associated with expression, activation or function of CEACAM, comprising administering to a subject in need thereof a pharmaceutical composition comprising a therapeutically effective amount of an antibody to CEACAM; and a pharmaceutically acceptable carrier.

According to some embodiments the disease or disorder is a cell proliferative disease or disorder. According to certain embodiments the cell proliferative disease or disorder is cancer. According to a specific embodiment the monoclonal antibody, or fragment thereof, has an affinity of at least about $10^{-8}$M to CEACAM1 and the cancer is melanoma.

According to other embodiments, the monoclonal antibody, or fragment thereof, has an affinity of at least about $5 \times 10^{-7}$M to CEACAM5 and the cancer is selected from the group consisting of: gastrointestinal, colorectal (CRC) pancreatic, non-small cell lung cancer (NSCL), breast, thyroid, stomach, ovarian, myeloma and uterine.

According to an additional embodiment, the disease or disorder associated with over expression of CEACAM1 is a viral infection.

According to some embodiments, the viral infection is caused by a virus selected from the group consisting of: DNA viruses, such as but not limited to cytomegalovirus (CMV), adenovirus, hepatitis virus and human papillomavirus (HPV); and RNA viruses such as but not limited to influenza virus and human immuno-deficiency virus (HIV).

According to an aspect of the present invention there is provided a method of immunomodulation, the method comprising contacting a CEACAM-expressing lymphocyte with the antibody or antibody fragment.

According to an aspect of the present invention there is provided a method of inhibiting migration of a CEACAM expressing tumor cell, the method comprising contacting the CEACAM expressing tumor cell with the antibody or antibody fragment, thereby inhibiting migration of a CEACAM expressing tumor cell.

According to some embodiments, the tumor cell comprises a melanoma tumor cell.

According to an aspect of the present invention there is provided a method of treating cancer, the method comprising administering to a subject in need thereof a therapeutically effective amount of the antibody or antibody fragment, thereby treating the cancer in the subject.

According to an aspect of the present invention there is provided a method of inhibiting CEACAM homotypic or heterotypic protein-protein interaction, the method comprising contacting a CEACAM1-expressing lymphocyte with the antibody or antibody fragment, thereby inhibiting CEACAM1 homotypic or heterotypic protein-protein interaction.

According to some embodiments, the isolated antibody or antibody fragment is attached to a cytotoxic moiety.

According to some embodiments, the cytotoxic moiety comprises a cytotoxin, a chemokine, a chemotherapeutic composition, a pro-apoptotic, an interferon, a radioactive moiety, or combinations thereof.

According to some embodiments, the antibody or antibody fragment is attached to an identifiable moiety.

According to some embodiments, cells of the cancer are characterized by over expression of CEACAM1 as compared to unaffected cells.

According to some embodiments, the method of treating cancer further comprises administering to the subject lymphocytes.

According to some embodiments, the lymphocytes comprise T cells or NK cells. According to some embodiments, the lymphocytes express CEACAM1. According to other embodiments, the CEACAM1-expressing lymphocyte is a Tumor Infiltrating Lymphocyte (TIL). According to other embodiments, the CEACAM1-expressing lymphocyte is a cytotoxic T cell.

The antibody of the present invention can be used to block CEACAM on either or both immune effector cells (CEACAM expressing lymphocytes e.g., tumor infiltrating cells, T cells or NK cells) and target cells (e.g., CEACAM expressing pathological cells such as cancer cells). Examples of cancer cells which are candidates for this therapy include, but are not limited to, melanoma, lung, thyroid, breast, colon, prostate, hepatic, bladder, renal, cervical, pancreatic, leukemia, lymphoma, myeloid, ovarian, uterus, sarcoma, biliary, or endometrial cells.

According to a further aspect of the invention there is provided a method of rendering a CEACAM expressing tumor cell susceptible to immunomodulation. The method comprising contacting the CEACAM expressing tumor cell (e.g., melanoma, lung, thyroid, breast, colon, prostate, hepatic, bladder, renal, cervical, pancreatic, leukemia, lymphoma, myeloid, ovarian, uterus, sarcoma, biliary or endometrial cell) with the antibody or antibody fragment described above, thereby rendering the CEACAM expressing tumor cell susceptible to immunomodulation.

Additionally or alternatively, the present invention also envisages a method of immunomodulation (e.g., inhibiting CEACAM1 homotypic or heterotypic protein-protein interaction), by contacting a CEACAM1-expressing lymphocyte with the antibody or antibody fragment described herein.

The therapeutic or preventive methods of the present teachings can be effected ex-vivo (e.g., used in T cell based adoptive immunotherapy) or in-vivo.

Antibodies of some embodiments of the invention can have anti cancer activity which is independent from its immunomodulatory activity described above.

In another aspect, the present invention provides a method for increasing the duration or progression of response or survival of a subject having cancer, comprising administering to the subject effective amounts of a composition comprising an antibody which recognizes CEACAM and an anti-neoplastic composition, wherein said anti-neoplastic composition comprises at least one chemotherapeutic agent, whereby the co-administration of the antibody and the anti-neoplastic composition effectively increases the duration or progression of response or survival.

Furthermore, the present invention provides a method for treating a subject having cancer, comprising administering to the subject effective amounts of a composition comprising an antibody to CEACAM and an anti-neoplastic composition whereby co-administration of the antibody to CEACAM and the anti-neoplastic composition effectively increases the response incidence in the group of subjects.

Aside from therapeutic applications, antibodies of the present invention can also be used in diagnostic applications.

Thus, according to a further aspect there is provided a method for diagnosing a cancer in a subject in need thereof, the method comprising contacting a biological sample derived from the subject (in-vivo, in vitro or ex-vivo) with the antibody or antibody fragment described herein, wherein a complex formation beyond a predetermined threshold is indicative of the cancer in the subject. According to some embodiments, cells of the cancer are characterized by over expression of CEACAM as compared to unaffected cells.

According to a particular embodiment the diagnosed cancer is selected from the group consisting of: melanoma, pancreatic cancer, lung cancer and myeloma.

According to another particular embodiment the measured protein is CEACAM5 and the diagnosed cancer is selected from the group consisting of: gastrointestinal, colorectal (CRC) pancreatic non-small cell lung cancer (NSCL), breast, thyroid, stomach, ovarian and uterine.

As mentioned, the method of the invention is affected under conditions sufficient to form an immunocomplex; such conditions (e.g., appropriate concentrations, buffers, temperatures, reaction times) as well as methods to optimize such conditions are known to those skilled in the art, and examples are disclosed herein. As used herein the phrase "immunocomplex" refers to a complex which comprises the antibody of the invention and the CEACAM. Determining a presence or level of the immunocomplex of the invention may be direct or by detecting an identifiable (detectable) moiety which may be attached to the antibody.

The level of the immunocomplex in the tested cell (e.g., a cell of a subject in need thereof) is compared to a predetermined threshold. It will be appreciated that the antibody of the present invention can also be used to measure the amount of serum soluble CEACAM. Regardless, the threshold may be determined based on a known reference level and/or a level in a control cell or serum. The control cell can be obtained from a control, healthy subject (e.g., a subject not suffering from the cancer) or from the same subject prior to disease initiation or following treatment. According to some embodiments of the invention, the control subject is of the same species e.g. human, preferably matched with the same age, weight, sex etc. as the subject in need thereof.

To facilitate diagnosis, the above teachings can be combined with other methods of diagnosing cancer which are well known in the art include but are not limited to imaging, molecular tests and surgical biopsies.

According to another aspect of present invention a method for detecting or quantifying the presence of CEACAM in is provided. Thus, the present invention also provides methods for diagnosing conditions associated with CEACAM expression using antibodies which recognizes CEACAM. Diagnostic methods according to the invention may be performed according to specific embodiments, in-vitro or ex-vivo. The antibodies according to the present invention may be also used to configure screening methods. For example, an ELISA assay can be constructed for measuring secreted or cell associated levels of polypeptide using monoclonal and polyclonal antibodies by standard methods known in the art.

According to one embodiment a method is provided for detecting or quantifying the presence of CEACAM, comprising the steps of:
 i. incubating a biological sample with an antibody to CEACAM or an antibody fragment thereof comprising at least an antigen-binding portion;
 ii. detecting the bound CEACAM using a detectable probe;
 iii. comparing the amount of (ii) to a standard curve obtained from reference samples containing known amounts of CEACAM; and
 iv. calculating the amount of the CEACAM in the sample from the standard curve.

According to another embodiment a method for diagnosing a disease or disorder associated with CEACAM expression is provided comprising the steps of:

i. incubating a biological sample with an antibody to CEACAM or an antibody fragment thereof comprising at least an antigen-binding portion;
ii. detecting the bound CEACAM using a detectable probe;
iii. comparing the amount of (ii) to a standard curve obtained from reference samples containing known amounts of CEACAM;
iv. calculating the amount of the CEACAM in the biological sample from the standard curve; and
v. comparing the amount of (iv) to a normal CEACAM amount.

According to some embodiments the biological sample is a body fluid of a mammalian subject. According to particular embodiments, the mammalian subject is human.

The antibodies of the present invention may be also used in screening assays for assessing the CEACAM levels in patients and for prediction of the effectiveness of treatment. The screening assays with the antibodies of the present invention may allow determination of the levels of CEACAM and therefore prediction of treatment outcome and planning of an appropriate treatment regimen.

According to other embodiments, the level of at least one of CEACAM1, CEACAM3 and CEACAM5 is assessed. According to a particular embodiment the level of CEACAM1 is assessed.

According to some embodiments of the invention, the antibody or antibody fragment is attached to an identifiable moiety.

It will be appreciated that such attachment of antibodies, or fragments thereof, and identifiable moiety can be effected using chemical conjugation or by recombinant DNA technology according to methods well known in the art.

The identifiable moiety can be a member of a binding pair, which is identifiable via its interaction with an additional member of the binding pair and a label which is directly visualized. In one example, the member of the binding pair is an antigen which is identified by a corresponding labeled antibody. In one example, the label is a fluorescent protein or an enzyme producing a colorimetric reaction.

Another aspect of the present invention relates to the use of an antibody to CEACAM or an antibody fragment thereof, for diagnosis or treatment of a cell proliferative or angiogenesis-related disease or disorder or a viral infection.

According one embodiment the cell proliferative disease is melanoma.

According to other embodiments the cell proliferative disease or disorder is a cancer selected from the group consisting of: gastrointestinal, colorectal (CRC) pancreatic non-small cell lung cancer (NSCL), breast, thyroid, stomach, ovarian, uterine, and myeloma.

According to one embodiment, the present invention provides use of an antibody to CEACAM or an antibody fragment thereof comprising at least an antigen-binding portion, for preparation of a medicament for treatment of a disorder or disease associated with expression or activation of, including but not limited to cancer and viral infection.

The invention also relates to use of an antibody to CEACAM or an antibody fragment thereof, for the manufacture of a diagnostic composition for the diagnosis of a cell proliferative or angiogenesis-related disease or disorder or a viral infection.

Essentially all of the uses known or envisioned in the prior art for CEACAM1, CEACAM3 and CEACAM5 antibodies can be accomplished with the antibodies of the present invention which are shown to posses improved affinity toward these proteins and superior inhibitory and in indirect immunomodulatory effects on CEACAM1 bearing cells. These uses include diagnostic, prophylactic and therapeutic techniques.

Further embodiments and the full scope of applicability of the present invention will become apparent from the detailed description given hereinafter.

DETAILED DESCRIPTION OF THE INVENTION

Figure 1:
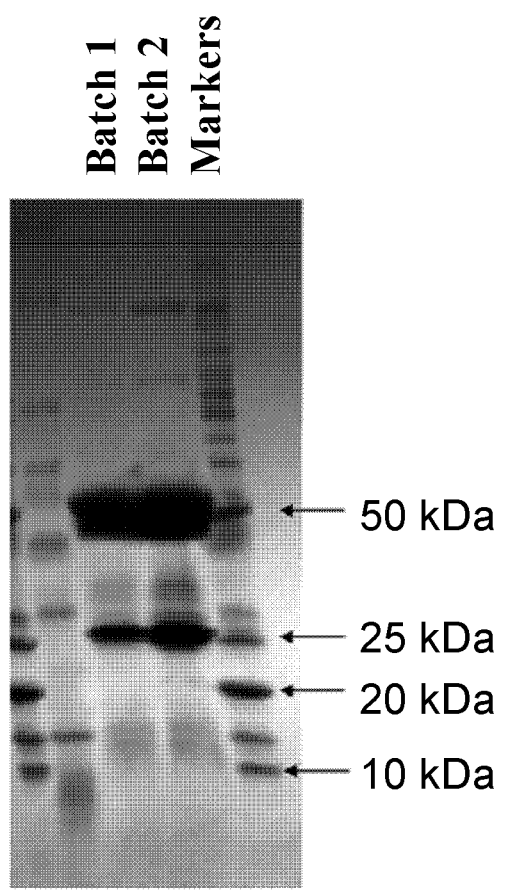
FIG. 1 is an SDS-PAGE image showing light and heavy chains of the chimeric antibody CM10.

The present invention provides antibodies which recognize CEACAM1 comprising specific sets of CDR sequences which possess improved and unique specificity, selectivity, affinity and/or activity.

Antibodies according to the present invention bind CEACAM1 with higher affinity than other anti-CEACAM1 antibodies, they blocks the function of CEACAM1, while not all anti CEACAM antibodies do, and more efficiently than polyclonal anti CEACAM antibodies. Furthermore, antibodies according to the present invention are effective against cancer cells, in particular melanoma cells: the antibodies render melanoma cells more susceptible to lymphocytes, inhibit melanoma growth rate in vivo, an effect which is enhanced when the antibody is combined with adoptive T cell transfer in vivo.

It is shown here for the first time that the in vivo anti-melanoma effect of anti-CEACAM1 antibodies according to the invention is a combined direct anti-tumor effect as well as immunomodulatory effect rendering the cells more susceptible to reactive lymphocytes.

An antibody according to the present invention, fragments and derivatives can be used as an effective tool for diagnosis, immunomodulation and cancer treatment.

The antibody inhibits CEACAM1 homophilic interactions, as determined by co-incubation of immune effector cells and target cells expressing CEACAM1 and assaying IL-2 secretion and by the in vitro killing assays.

The antibody of the present invention is shown to enhances CM10 enhances HLA restricted T cell killing and to enhance granzyme B (a serine protease involves in mediation apoptosis of the target cells) secretion from effector NK and T cells in the presence of specific target cells, thus enabling the observed enhanced killing of the target cells by the antibody. It is also inhibits the binding between CEACAM1 to CEACAM5 in a dose-dependent manner therefore can be used to treat malignancies that express high level of CEACAM5 and exploit the CEACAM1-CEACAM5 axis in order to suppress the immune cells.

In addition it is herein shown that, an antibody according to the invention is effective in inhibiting melanoma cells invasion. Furthermore, in vivo administration of an antibody according to the invention, either alone or in combination with reactive lymphocytes was shown effective in inhibiting growth of melanoma tumors. The combination of adoptive human T cell transfer with monoclonal antibody injections exhibited significant synergism and strongly inhibited xenograft growth compared to the isotype control group.

According to a further aspect of the invention there is provided an isolated antibody or antibody fragment having the same binding specificity and selectivity to an antibody defined herein comprising an antigen recognition domain having specific CDR segments described above. According to this aspect, isolated antibody or antibody fragment is capable of binding the same epitope determinant of the CEACAM1 protein as does the antibody described above by its specific CDR segments sequences.

The proposed sequence of an epitope to which a monoclonal antibody according to the invention binds is disclosed herein for the same time, together with proposed isolated peptides derived from this epitope which can be used for raising additional monoclonal antibodies.

Monoclonal antibodies (mAbs) can be designed to selectively target tumor cells and elicit a variety of responses once bound. These agents can destruct tumor cells in different ways such as blocking tumor cell proliferation or activating the immune system. Chimeric monoclonal antibodies according to the present invention were designed to specifically bind and neutralize various functions of the CEACAM1 protein and other CEACAM subtype proteins, and to induce the specific death of tumor cells. Without wishing to be bound to any theory, it is suggested that monoclonal antibodies according to the present invention act also via activation of the immune system against cancerous cells.

Both the clinical and biological evidence highlight CEACAM1 as a promising target for the development of targeted-immunotherapy. CEACAM1 is not found on normal melanocytes, but undergoes neo-expression and is widely expressed on the vast majority of metastatic melanoma specimens. It has been previously demonstrated mechanistically that CEACAM1 protects melanoma cells by inhibiting effector functions of NK cells and T cells.

It is herein demonstrated for the first time that CM10 is a chimeric monoclonal antibody which binds with high affinity to human CEACAM1. In-vitro, CM10 efficiently blocked CEACAM1-homophilic interactions in a dose dependent manner and improves CEACAM1 positive melanoma cells killing by T cells and NK cells. Moreover, CM10 significantly inhibited the in-vivo growth of melanoma xenografts when administered systemically along with melanoma-reactive human T lymphocytes (tumor-infiltrating lymphocytes, TILs). Without wishing to be bound to any theory, this is in line with the suggested mechanism of action; abrogation of immune-protective interactions of the tumor cells with the activated lymphocytes.

Several evidences reported that CEACAM1 is expressed by a wide variety of epithelial cells, including colon, prostate, breast, kidney etc. Extensive examination of CEACAM1 expression profile on normal and malignant tissues by IHC have been performed. The expression analysis showed a strong staining of melanoma cells, as compared to no staining of the vast majority of the tissues tested in a normal human tissue. Nevertheless, some selective staining was observed in restricted sites of several organs. When more quantitative method was used to quantify the number of CM10 mAb molecules bound to malignant and normal primary cells, very low CM10 molecules could be detected in normal cells, which may indicate that CM10 binds mostly to patient's tumor cells. Furthermore it is shown that CM10 has no effect on primary cells proliferation and is completely or almost completely, unable to induce CDC or ADCC indicating the potential safety of the monoclonal antibody in human subjects.

Since CM10 has an immunomodulation activity, possible immune-related side effects, are evaluated. Following PBMC activation, CEACAM1 is upregulated on the activated lymphocytes (Gray-Owen and Blumberg 2006, Nat Rev Immunol 6, 433-46). Ex-vivo human PBMC proliferation assay revealed that CM10 has no effect on naïve and activated PBMC proliferative response.

The main advantage of CEACAM1 blockade over abrogation of generalized inhibitory mechanisms is the expected selectivity to the vicinity of the tumor and therefore fewer adverse events compare to other general immune toxicity agents.

As demonstrated in the present invention, CM10 shows encouraging activity and safety profile and is a promising candidate for cancer immunotherapy and can be used as a strategy to selectively enhance the anti-tumor properties of the endogenous immune response in several malignancies, such as melanoma and non-small cell lung cancer.

Binding to additional CEACAM subtypes increases the therapeutic profile of the antibody, thus it can be used for diagnosis and treatment of other types of malignancies which do not extensively express CEACAM1 but express CEACAM5, for example.

CEACAM5 has been found to be over-expressed in a high percentage of many human tumors, including 90% of gastrointestinal, colorectal (CRC) and pancreatic cancers, 70% of non-small cell lung cancer cells and 50% of breast cancers. It is also over-expressed in thyroid, stomach, ovarian and uterine cancers (Thompson, Grunert et al. 1991, J Clin Lab Anal 5, 344-66). CEACAM5 even serves as a clinical marker for liver metastasis in CRC and post-surgical surveillance of colon cancer (Duffy 2001, Clin Chem 47, 624-30). The evidence that CM10 is capable to bind CEACA5 is very important and can expand the possible indications that can be treated by CM10 from 4-5 types of malignancies to above 10. The anti-CEACAM5 agents that have entered clinical trials include anti-CEACAM5 antibodies conjugated to toxic substances such as radioactive substances for both diagnostic purposes and for the treatment of various malignancies. It seems that even these toxic conjugated forms don't show safety problems, which can indicate that CEACAM5 is a safe target.

The human counterparts of murine IgG subclasses are based on similarities in biological and functional activities. Murine IgG2a and IgG2b and human IgG1 and IgG3 share the ability to fix complement and bind to protein antigens (Hussain et al., 1995, Clinical and Diagnostic Laboratory Immunology 726-732). Murine IgG1 and human IgG4 are considered to be similar because of their property of binding to mast cells. Human IgG4 is the only human IgG subclass which does not activate complement and the subclasses IgG1 and 3 are the most effective in activating complements. For mouse it is the subclasses IgG2a and IgG2b which are active with IgG1 and possibly IgG3 being inactive (Clark M R., Chem Immunol. 1997; 65:88-110).

Several known monoclonal antibodies which recognize CEACAM1 are of subtype mouse IgG1. As the human equivalent of mouse IgG1 is IgG4 it would be expected to create a chimeric antibody comprising the human IgG4 constant framework. Unexpectedly, according to some embodiments of the present invention chimeric monoclonal antibodies comprise a human IgG1 constant framework.

According to one aspect, the present invention provides a monoclonal antibody which recognizes CEACAM1, or an antibody fragment comprising at least an antigen-binding portion thereof, comprising at least one heavy-chain CDR comprising a sequence selected from the group consisting of: SEQ ID NO: 1, SEQ ID NO: 2 and SEQ ID NO: 3, and at least one light-chain CDR comprising a sequence selected from the group consisting of: SEQ ID NO: 4, SEQ ID NO: 5 and SEQ ID NO: 6, and analogs and derivatives thereof.

According to some embodiments, analogs and derivatives of the monoclonal antibody or fragment thereof, having at least 90% sequence identity with the sequence of the reference sequence are disclosed.

According to other embodiments analogs and derivatives of the monoclonal antibody or fragment thereof having at least 95% sequence identity with the reference sequence are disclosed.

According to yet other embodiments, analogs and derivatives of the monoclonal antibody or fragment thereof having at least 98% sequence identity with the CDR sequence of the reference antibody are disclosed.

According to one embodiment the antibody or antibody fragment comprises at least two heavy-chain CDRs comprising a sequence selected from the group consisting of: SEQ ID NO: 1, SEQ ID NO: 2 and SEQ ID NO: 3, and at least one light-chain CDRs comprising a sequence selected from the group consisting of: SEQ ID NO: 4, SEQ ID NO: 5 and SEQ ID NO: 6, and analogs and derivatives thereof having at least 97% sequence identity with the sequence of the monoclonal antibody or fragment thereof.

According to other embodiments the antibody or antibody fragment comprises at least one heavy-chain CDR comprising a sequence selected from the group consisting of: SEQ ID NO: 1, SEQ ID NO: 2 and SEQ ID NO: 3, and at least two light-chain CDRs comprising a sequence selected from the group consisting of: SEQ ID NO: 4, SEQ ID NO: 5 and SEQ ID NO: 6, and analogs and derivatives thereof having at least 97% sequence identity with the sequence of the monoclonal antibody or fragment thereof.

According to yet other embodiments the antibody or antibody fragment comprises at least two heavy-chain CDRs comprising a sequence selected from the group consisting of: SEQ ID NO: 1, SEQ ID NO: 2 and SEQ ID NO: 3, and at least two light-chain CDRs comprising a sequence selected from the group consisting of: SEQ ID NO: 4, SEQ ID NO: 5 and SEQ ID NO: 6, and analogs and derivatives thereof having at least 97% sequence identity with the sequence of the monoclonal antibody or fragment thereof.

According to some embodiments the antibody or antibody fragment comprises at least one heavy-chain CDR sequence of at least five amino acids derived from a sequence selected from the group consisting of: SEQ ID NO: 19, SEQ ID NO: 20 and SEQ ID NO: 21, and at least one light-chain CDR sequence of at least five amino acids derived from a sequence selected from the group consisting of: SEQ ID NO: 22, SEQ ID NO: 23 and SEQ ID NO: 24, and analogs and derivatives thereof having at least 97% sequence identity with the sequence of the monoclonal antibody or fragment thereof.

According to other embodiments, the antibody binding site of the antibody or fragment thereof consists of three heavy chain CDRs selected from the group consisting of SEQ ID NOs: 7, 8, 9, 13, 14 and 15 and three light chain CDRs selected from the group consisting of SEQ ID NOs: 10, 11, 12, 16, 17, 18, and analogs and derivatives thereof having at least 97% sequence identity with the antibody binding site.

According to yet other embodiments, the antibody binding site consists of the six CDRs of SEQ ID NOs: 13, 14, 15, 16, 17, and 18.

According to other embodiments, the antibody binding site consists of the six CDRs of SEQ ID NOs: 7, 8, 9, 10, 11, and 12.

The CDR sequences according to the invention were identified using two different algorithm methods: IMGT algorithm (Lefranc et al., 1999, Nucleic Acids Research, 27, 209-212); and KABAT algorithm (Wu T T and Kabat E. A., 1970, J. Exp. Med. 132, 211-250). The sequences revealed by both methods are disclosed.

According to some embodiments, the heavy chain CDR1 of the antibody according to the invention or a fragment thereof is selected from NNLIE (SEQ ID NO: 7) and GYAFTNNL (SEQ ID NO: 13).

According to some embodiments, the heavy chain CDR2 of the antibody according to the invention or a fragment thereof is selected from VINPGSGDTNYNEKFKG (SEQ ID NO: 8) and INPGSGDT (SEQ ID NO: 14).

According to some embodiments, the heavy chain CDR3 of the antibody according to the invention or a fragment thereof is selected from GDYYGGFAVDY (SEQ ID NO: 9) and ARGDYYGGFAVDY (SEQ ID NO: 15).

According to some embodiments, the light chain CDR1 of the antibody according to the invention or a fragment thereof is selected from RTSQDIGNYLN (SEQ ID NO: 10) and QDIGNY (SEQ ID NO: 16).

According to some embodiments, the light chain CDR2 of the antibody according to the invention or a fragment thereof is selected from YTSRLHS (SEQ ID NO: 11) and YTS (SEQ ID NO: 17).

According to some embodiments, the light chain CDR3 of the antibody according to the invention or a fragment thereof is selected from QQGKSLP (SEQ ID NO: 12) and QQGKSLPRT (SEQ ID NO: 18).

According to some embodiments a monoclonal antibody which recognizes CEACAM1 or a fragment thereof comprising at least an antigen binding portion is provided, wherein the heavy chain CDRs consist of the sequences of SEQ ID NOs: 7, 8 and 9.

According to some embodiments a monoclonal antibody which recognizes CEACAM1 or a fragment thereof comprising at least an antigen binding portion is provided, wherein the heavy chain CDRs consist of the sequences of SEQ ID NOs: 13, 14 and 15.

According to some embodiments a monoclonal antibody which recognizes CEACAM1 or a fragment thereof comprising at least an antigen binding portion is provided, wherein the light chain CDRs consist of the sequences of SEQ ID NOs: 10, 11 and 12.

According to some embodiments a monoclonal antibody which recognizes CEACAM1 or a fragment thereof comprising at least an antigen binding portion is provided, wherein the light chain CDRs consist of the sequences of SEQ ID NOs: 16, 17 and 18.

According to a specific embodiment the antibody comprises the heavy chain variable domain sequence:

According to a specific embodiment the antibody or fragment thereof comprises a heavy chain variable domain sequence consisting of the of SEQ ID NO: 26 and a light chain variable domain sequence consisting of SEQ ID NO: 28, or an analog or derivative thereof having at least 90% sequence identity with the antibody or fragment sequence.

According to some particular embodiments the present invention provides a monoclonal antibody, or an antibody fragment comprising a set of six CDRs selected from i. SEQ ID NOs: 13, 14, 15, 16, 17, and 18 and ii. SEQ ID NOs: 7, 8, 9, 10, 11, and 12; and analogs and derivatives thereof having at least 97% sequence identity with said CDR sequences, and a framework sequence selected from mouse IgG2a, mouse IgG2b, mouse IgG3, human IgG1, human IgG2, human IgG3, wherein the monoclonal antibody binds with an affinity of at least about $5 \times 10^{-7}$M to at least two CEACAM subtypes.

According to a particular embodiment, a chimeric monoclonal antibody which recognizes CEACAM1 is provided, comprising at least one CDR sequence selected from the group consisting of: SEQ ID NOs: 7, 8, 9, 10, 11, 12, 13, 14, 15, 16, 17, and 18; and analogs and derivatives thereof having at least 97% sequence identity with said CDR sequences, and a constant region sequence selected from human IgG1, human IgG2 and human IgG3, wherein the monoclonal antibody binds with an affinity of at least about $5 \times 10^{-7}$M to at least two CEACAM subtypes.

According to a particular embodiment, a chimeric or humanized monoclonal antibody which recognizes CEACAM1 is provided comprising a set of six CDRs selected from i. SEQ ID NOs: 13, 14, 15, 16, 17, and 18 and ii. SEQ ID NOs: 7, 8, 9, 10, 11, and 12; and analogs and derivatives thereof having at least 97% sequence identity with said CDR sequences, and a constant region subclass selected from human IgG1, human IgG2 and human IgG3, wherein the monoclonal antibody binds with an affinity of at least about $5 \times 10^{-7}$M to at least two CEACAM subtypes.

According to yet another particular embodiment a chimeric monoclonal antibody or a fragment thereof comprising at least the antigen-binding portion, is provided comprising a heavy chain sequence according to SEQ ID NO: 30.

According to yet another particular embodiment a chimeric monoclonal antibody or a fragment thereof comprising at least the antigen-binding portion, is provided comprising a light chain sequence according to SEQ ID NO: 31.

According to yet another particular embodiment a chimeric monoclonal antibody or a fragment thereof comprising at least the antigen-binding portion, is provided comprising a human IgG1 heavy chain sequence according to SEQ ID NO: 30, and a human IgG1 light chain sequence according to SEQ ID NO: 31.

Definitions

The term "CEACAM1" is used to refer to the protein product of the CEACAM1 gene e.g., NP_001020083.1, NP_001703.2. In humans, 11 different CEACAM1 splice variants have been detected so far. Individual CEACAM1 isoforms differ with respect to the number of extracellular immunoglobulin-like domains (for example, CEACAM1 with four extracellular immunoglobulin-like domains is known as CEACAM1-4), membrane anchorage and/or the length of their cytoplasmic tail (for example, CEACAM1-4 with a long cytoplasmic tail is known as CEACAM1-4L and CEACAM1-4 with a short cytoplasmic tail is known as CEACAM1-4S). The N-terminal domain of CEACAM1 starts immediately after the signal peptide and its structure is regarded as IgV-type. For example, in CEACAM1 annotation P13688, the N-terminal IgV-type domain is comprised of 108 amino acids, from amino acid 35 to 142. This domain was identified as responsible for the homophilic binding activity (Watt et al., 2001, Blood. 98, 1469-79). All variants, including these splice variants are included within the term "CEACAM1".

An "anti-CEACAM1 antibody", "an antibody which recognizes CEACAM1", "an antibody against CEACAM1", or "an antibody to CEACAM1" is an antibody that binds to the CEACAM1 protein with sufficient affinity and specificity. Typically, an antibody according to the present teachings is capable of binding CEACAM1 with a minimal affinity of about $10^{-8}$ or $10^{-9}$ M. Some of the monoclonal antibodies of the present invention are capable of binding CEACAM3, 5 and/or 8 with a minimal affinity of about $5 \times 10^{-7}$ M.

Preferably, the anti-CEACAM1 antibody of the invention can be used as a diagnostic or therapeutic agent in targeting and interfering with diseases or conditions wherein the CEACAM1 expression or activity is involved.

An "antigen" is a molecule or a portion of a molecule capable of eliciting antibody formation and being bound by an antibody. An antigen may have one or more than one epitope. The specific reaction referred to above is meant to indicate that the antigen will react, in a highly selective manner, with its corresponding antibody and not with the multitude of other antibodies which may be evoked by other antigens. An antigen according to the present invention is a CEACAM1 protein or a fragment thereof.

The term "antigenic determinant" or "epitope" according to the invention refers to the region of an antigen molecule that specifically reacts with particular antibody. Peptide sequences derived from an epitope can be used, alone or in conjunction with a carrier moiety, applying methods known in the art, to immunize animals and to produce additional polyclonal or monoclonal antibodies. Isolated peptides derived from an epitope may be used in diagnostic methods to detect antibodies and as therapeutic agents when inhibition of said antibodies is required.

Antibodies, or immunoglobulins, comprise two heavy chains linked together by disulfide bonds and two light chains, each light chain being linked to a respective heavy chain by disulfide bonds in a "Y" shaped configuration. Proteolytic digestion of an antibody yields Fv (Fragment variable) and Fc (fragment crystalline) domains. The antigen binding domains, Fab, include regions where the polypeptide sequence varies. The term F(ab')$_2$ represents two Fab' arms linked together by disulfide bonds. The central axis of the antibody is termed the Fc fragment. Each heavy chain has at one end a variable domain ($V_H$) followed by a number of constant domains ($C_H$). Each light chain has a variable domain ($V_L$) at one end and a constant domain ($C_L$) at its other end, the light chain variable domain being aligned with the variable domain of the heavy chain and the light chain constant domain being aligned with the first constant domain of the heavy chain (CH1). The variable domains of each pair of light and heavy chains form the antigen-binding site. The domains on the light and heavy chains have the same general structure and each domain comprises four framework regions, whose sequences are relatively conserved, joined by three hypervariable domains known as complementarity determining regions (CDR1-3). These domains contribute specificity and affinity of the antigen-binding site. The isotype of the heavy chain (gamma, alpha, delta, epsilon or mu) determines immunoglobulin class (IgG, IgA, IgD, IgE or IgM, respectively). The light chain is either of two isotypes (kappa, κ or lambda, λ) found in all antibody classes.

The term "antibody" is used in the broadest sense and includes monoclonal antibodies (including full length or intact monoclonal antibodies), polyclonal antibodies, multivalent antibodies, multispecific antibodies (e.g., bispecific antibodies), and antibody fragments so long as they exhibit the desired biological activity.

The antibody according to the present invention is a molecule comprising at least the antigen-binding portion of an antibody. Antibody or antibodies according to the invention include intact antibodies, such as polyclonal antibodies or monoclonal antibodies (mAbs), as well as proteolytic fragments thereof such as the Fab or F(ab')$_2$ fragments. Further included within the scope of the invention are chimeric antibodies; human and humanized antibodies; recombinant and engineered antibodies, and fragments thereof. Furthermore, the DNA encoding the variable region of the antibody can be inserted into the DNA encoding other antibodies to produce chimeric antibodies. Single chain antibodies also fall within the scope of the present invention.

"Antibody fragments" comprise only a portion of an intact antibody, generally including an antigen binding site of the intact antibody and thus retaining the ability to bind antigen. Examples of antibody fragments encompassed by the present definition include: (i) the Fab fragment, having VL, CL, VH and CH1 domains; (ii) the Fab' fragment, which is a Fab fragment having one or more cysteine residues at the C-terminus of the CH1 domain; (iii) the Fd fragment having VH and CH1 domains; (iv) the Fd' fragment having VH and CHI domains and one or more cysteine residues at the C-terminus of the CH1 domain; (v) the Fv fragment having the VL and VH domains of a single arm of an antibody; (vi) the dAb fragment (Ward et al., Nature 1989, 341, 544-546) which consists of a VH domain; (vii) isolated CDR regions; (viii) F(ab')$_2$ fragments, a bivalent fragment including two Fab' fragments linked by a disulphide bridge at the hinge region; (ix) single chain antibody molecules (e.g. single chain Fv; scFv) (Bird et al., Science 1988, 242, 423-426; and Huston et al., PNAS (USA) 1988, 85, 5879-5883); (x) "diabodies" with two antigen binding sites, comprising a heavy chain variable domain (VH) connected to a light chain variable domain (VL) in the same polypeptide chain (see, e.g., EP 404,097; WO 93/11161; and Hollinger et al., Proc. Natl. Acad. Sci. USA, 1993, 90, 6444-6448); (xi) "linear antibodies" comprising a pair of tandem Fd segments (VH-CH1-VH-CH1) which, together with complementary light chain polypeptides, form a pair of antigen binding regions (Zapata et al. Protein Eng., 1995, 8, 1057-1062; and U.S. Pat. No. 5,641,870).

Single chain antibodies can be single chain composite polypeptides having antigen binding capabilities and comprising amino acid sequences homologous or analogous to the variable regions of an immunoglobulin light and heavy chain i.e. linked $V_H$-$V_L$ or single chain Fv (scFv).

A "neutralizing antibody" as used herein refers to a molecule having an antigen-binding site to a specific receptor or ligand target capable of reducing or inhibiting (blocking) activity or signaling through a receptor, as determined by in vivo or in vitro assays, as per the specification.

The term "monoclonal antibody" as used herein refers to an antibody obtained from a population of substantially homogeneous antibodies, i.e., the individual antibodies comprising the population are identical except for possible naturally occurring mutations that may be present in minor amounts. Monoclonal antibodies are highly specific, being directed against a single antigen. Furthermore, in contrast to polyclonal antibody preparations that typically include different antibodies directed against different determinants (epitopes), each monoclonal antibody is directed against a single determinant on the antigen. The modifier "monoclonal" is not to be construed as requiring production of the antibody by any particular method. mAbs may be obtained by methods known to those skilled in the art. For example, the monoclonal antibodies to be used in accordance with the present invention may be made by the hybridoma method first described by Kohler et al., Nature 1975, 256, 495, or may be made by recombinant DNA methods (see, e.g., U.S. Pat. No. 4,816,567). The "monoclonal antibodies" may also be isolated from phage antibody libraries using the techniques described in Clackson et al., Nature 1991, 352, 624-628 or Marks et al., J. Mol. Biol., 1991, 222:581-597, for example.

The mAbs of the present invention may be of any immunoglobulin class including IgG, IgM, IgE, IgA. A hybridoma producing a mAb may be cultivated in vitro or in vivo. High titers of mAbs can be obtained in vivo production where cells from the individual hybridomas are injected intraperitoneally into pristine-primed Balb/c mice to produce ascites fluid containing high concentrations of the desired mAbs. mAbs of isotype IgM or IgG may be purified from such ascites fluids, or from culture supernatants, using column chromatography methods well known to those of skill in the art.

The monoclonal antibodies herein specifically include "chimeric" antibodies in which a portion of the heavy and/or light chain is identical with or homologous to corresponding sequences in antibodies derived from a particular species or belonging to a particular antibody class or subclass, while the remainder of the chain(s) is identical with or homologous to corresponding sequences in antibodies derived from another species or belonging to another antibody class or subclass, as well as fragments of such antibodies, so long as they exhibit the desired biological activity (U.S. Pat. No. 4,816,567; and Morrison et al., Proc. Natl. Acad. Sci. USA 81:6851-6855 (1984)). In addition, complementarity determining region (CDR) grafting may be performed to alter certain properties of the antibody molecule including affinity or specificity. A non-limiting example of CDR grafting is disclosed in U.S. Pat. No. 5,225,539.

Chimeric antibodies are molecules, the different portions of which are derived from different animal species, such as those having a variable region derived from a murine mAb and a human immunoglobulin constant region. Antibodies which have variable region framework residues substantially from human antibody (termed an acceptor antibody) and complementarity determining regions substantially from a mouse antibody (termed a donor antibody) are also referred to as humanized antibodies. Chimeric antibodies are primarily used to reduce immunogenicity in application and to increase yields in production, for example, where murine mAbs have higher yields from hybridomas but higher immunogenicity in humans, such that human/murine chimeric mAbs are used. Chimeric antibodies and methods for their production are known in the art (for example PCT patent applications WO 86/01533, WO 97/02671, WO 90/07861, WO 92/22653 and U.S. Pat. Nos. 5,693,762, 5,693,761, 5,585,089, 5,530,101 and 5,225,539).

"Humanized" forms of non-human (e.g., murine) antibodies are chimeric antibodies that contain minimal sequence derived from non-human immunoglobulin. For the most part, humanized antibodies are human immunoglobulins (recipient antibody) in which residues from a hypervariable region of the recipient are replaced by residues from a hypervariable region of a non-human species (donor antibody) such as mouse, rat, rabbit or nonhuman primate having the desired specificity, affinity, and capacity. In some instances, framework region (FR) residues of the human immunoglobulin are replaced by corresponding non-human residues. Furthermore, humanized antibodies may comprise residues that are not found in the recipient antibody or in the donor antibody. These modifications are made to further refine antibody performance. In general, the humanized antibody will comprise substantially all of at least one, and typically two, variable domains, in which all or substantially all of the hypervariable loops correspond to those of a non-human immunoglobulin and all or substantially all of the FRs are those of a human immunoglobulin sequence. The humanized antibody optionally will also comprise at least a portion of an immunoglobulin constant region (Fc), typically that of a human immunoglobulin. For further details, see Jones et al., Nature 1986, 321, 522-525; Riechmann et al., Nature 1988, 332, 323-329; and Presta, Curr. Op. Struct. Biol., 1992 2, 593-596.

A "human antibody" is one which possesses an amino acid sequence which corresponds to that of an antibody produced by a human and/or has been made using any of the techniques for making human antibodies as disclosed herein. This definition of a human antibody specifically excludes a humanized antibody comprising non-human antigen-binding residues. Human antibodies can be produced using various techniques known in the art. In one embodiment, the human antibody is selected from a phage library, where that phage library expresses human antibodies (Vaughan et al. Nature Biotechnology 1996 14, 309-314; Sheets et al. PNAS (USA), 1998, 95, 6157-6162); Hoogenboom and Winter, J. Mol. Biol., 1991, 227, 381; Marks et al., J. Mol. Biol., 1991, 222, 581). Human antibodies can also be made by introducing human immunoglobulin loci into transgenic animals, e.g., mice in which the endogenous immunoglobulin genes have been partially or completely inactivated. Upon challenge, human antibody production is observed, which closely resembles that seen in humans in all respects, including gene rearrangement, assembly, and antibody repertoire. This approach is described, for example, in U.S. Pat. Nos. 5,545,807; 5,545,806; 5,569,825; 5,625,126; 5,633,425; 5,661,016, and in the following scientific publications: Marks et al, Bio/Technology 10: 779-783 (1992); Lonberg et al., Nature 368: 856-859 (1994); Morrison, Nature 368:812-13 (1994); Fishwild et al., Nature Biotechnology 14: 845-51 (1996); Neuberger, Nature Biotechnology 14: 826 (1996); Lonberg and Huszar, Intern. Rev. Immunol. 13:65-93 (1995). Alternatively, the human antibody may be prepared via immortalization of human B lymphocytes producing an antibody directed against a target antigen (such B lymphocytes may be recovered from an individual or may have been immunized in vitro). See, e.g., Cole et al., Monoclonal Antibodies and Cancer Therapy, Alan R. Liss, p. 77 (1985); Boerner et al., J. Immunol., 147 (1):86-95 (1991); and U.S. Pat. No. 5,750,373.

By the term "single chain variable fragment (scFv)" is meant a fusion of the variable regions of the heavy and light chains of immunoglobulin, linked together with a short (usually serine, glycine) linker. Single chain antibodies can be single chain composite polypeptides having antigen binding capabilities and comprising amino acid sequences homologous or analogous to the variable regions of an immunoglobulin light and heavy chain (linked $V_H$-$V_L$ or single chain Fv (scFv)). Both $V_H$ and $V_L$ may copy natural monoclonal antibody sequences or one or both of the chains may comprise a CDR-FR construct of the type described in U.S. Pat. No. 5,091,513, the entire contents of which are incorporated herein by reference. The separate polypeptides analogous to the variable regions of the light and heavy chains are held together by a polypeptide linker. Methods of production of such single chain antibodies, particularly where the DNA encoding the polypeptide structures of the $V_H$ and $V_L$ chains are known, may be accomplished in accordance with the methods described, for example, in U.S. Pat. Nos. 4,946,778, 5,091,513 and 5,096,815, the entire contents of each of which are incorporated herein by reference.

A "molecule having the antigen-binding portion of an antibody" as used herein is intended to include not only intact immunoglobulin molecules of any isotype and generated by any animal cell line or microorganism, but also the antigen-binding reactive fraction thereof, including, but not limited to, the Fab fragment, the Fab' fragment, the F(ab')$_2$ fragment, the variable portion of the heavy and/or light chains thereof, Fab mini-antibodies (see WO 93/15210, U.S. patent application Ser. No. 08/256,790, WO 96/13583, U.S. patent application Ser. No. 08/817,788, WO 96/37621, U.S. patent application Ser. No. 08/999,554, the entire contents of which are incorporated herein by reference), dimeric bispecific mini-antibodies (see Muller et al., 1998) and chimeric or single-chain antibodies incorporating such reactive fraction, as well as any other type of molecule or cell in which such antibody reactive fraction has been physically inserted, such as a chimeric T-cell receptor or a T-cell having such a receptor, or molecules developed to deliver therapeutic moieties by means of a portion of the molecule containing such a reactive fraction. Such molecules may be provided by any known technique, including, but not limited to, enzymatic cleavage, peptide synthesis or recombinant techniques.

Antibodies according to the invention can be obtained by administering CEACAM1, or epitope-bearing fragments, analogs, or cells expressing, to an animal, preferably a nonhuman, using routine protocols. For preparation of monoclonal antibodies, any technique known in the art that provides antibodies produced by continuous cell line cultures can be used. Examples include various techniques, such as those in Kohler, G. and Milstein, C., Nature 256: 495-497 (1975); Kozbor et al., Immunology Today 4: 72 (1983); Cole et al., pg. 77-96 in MONOCLONAL ANTIBODIES AND CANCER THERAPY, Alan R. Liss, Inc. (1985).

Besides the conventional method of raising antibodies in vivo, antibodies can be generated in vitro using phage display technology. Such a production of recombinant antibodies is much faster compared to conventional antibody production and they can be generated against an enormous number of antigens. Furthermore, when using the conventional method, many antigens prove to be non-immunogenic or extremely toxic, and therefore cannot be used to generate antibodies in animals. Moreover, affinity maturation (i.e., increasing the affinity and specificity) of recombinant antibodies is very simple and relatively fast. Finally, large numbers of different antibodies against a specific antigen can be generated in one selection procedure. To generate recombinant monoclonal antibodies one can use various methods all based on display libraries to generate a large pool of antibodies with different antigen recognition sites. Such a library can be made in several ways: One can generate a synthetic repertoire by cloning synthetic CDR3 regions in a pool of heavy chain germline genes and thus generating a large antibody repertoire, from which recombinant antibody fragments with various specificities can be selected. One can use the lymphocyte pool of humans as starting material for the construction of an antibody library. It is possible to construct naive repertoires of human IgM antibodies and thus create a human library of large diversity. This method has been widely used successfully to select a large number of antibodies against different antigens. Protocols for bacteriophage library construction and selection of recombinant antibodies are provided in the well-known reference text Current Protocols in Immunology, Colligan et al (Eds.), John Wiley & Sons, Inc. (1992-2000), Chapter 17, Section 17.1.

Non-human antibodies may be humanized by any methods known in the art. In one method, the non-human complementarity determining regions (CDRs) are inserted into a human antibody or consensus antibody framework sequence. Further changes can then be introduced into the antibody framework to modulate affinity or immunogenicity.

For example, U.S. Pat. No. 5,585,089 of Queen et al. discloses a humanized immunoglobulin and methods of preparing same, wherein the humanized immunoglobulin comprises complementarity determining regions (CDRs) from a donor immunoglobulin and heavy and light chain variable region frameworks from human acceptor immunoglobulin heavy and light chains, wherein said humanized immunoglobulin comprises amino acids from the donor immunoglobulin framework outside the Kabat and Chothia CDRs, wherein the donor amino acids replace corresponding amino acids in the acceptor immunoglobulin heavy or light chain frameworks.

U.S. Pat. No. 5,225,539, of Winter, also discloses an altered antibody or antigen-binding fragment thereof and methods of preparing same, wherein a variable domain of the antibody or antigen-binding fragment has the framework regions of a first immunoglobulin heavy or light chain variable domain and the complementarity determining regions of a second immunoglobulin heavy or light chain variable domain, wherein said second immunoglobulin heavy or light chain variable domain is different from said first immunoglobulin heavy or light chain variable domain in antigen binding specificity, antigen binding affinity, species, class or subclass.

Anti-idiotype antibodies specifically immunoreactive with an antibody of the invention are also comprehended.

Techniques for the production of single chain antibodies (U.S. Pat. No. 4,946,778) can be adapted to produce single chain antibodies to polypeptides or polynucleotides of this invention. Also, transgenic mice, or other organisms such as other mammals, can be used to express humanized antibodies immunospecific to the polypeptides or polynucleotides of the invention.

Alternatively, phage display technology can be utilized to select antibody genes with binding activities towards a polypeptide of the invention either from repertoires of PCR amplified v-genes of lymphocytes from humans screened for possessing anti-CEACAM1 or from libraries (McCafferty, et al., 1990, Nature 348, 552-554; Marks, et al., 1992, Biotechnology 10, 779-783). The affinity of these antibodies can also be improved by, for example, chain shuffling (Clackson et al., 1991, Nature 352:628).

The above-described antibodies can be employed to isolate or to identify clones expressing the polypeptides to purify the polypeptides by, for example, affinity chromatography.

The invention also provides conservative amino acid variants of the antibody molecules according to the invention. Variants according to the invention also may be made that conserve the overall molecular structure of the encoded proteins. Given the properties of the individual amino acids comprising the disclosed protein products, some rational substitutions will be recognized by the skilled worker. Amino acid substitutions, i.e. "conservative substitutions," may be made, for instance, on the basis of similarity in polarity, charge, solubility, hydrophobicity, hydrophilicity, and/or the amphipathic nature of the residues involved.

A "disorder" is any condition that would benefit from treatment with the antibody. This includes chronic and acute disorders or diseases including those pathological conditions which predispose the mammal to the disorder in question. Non-limiting examples of disorders to be treated herein include benign and malignant tumors; leukemias and lymphoid malignancies; neuronal, glial, astrocytal, hypothalamic and other glandular, macrophagal, epithelial, stromal and blastocoelic disorders; and inflammatory, angiogenic, immunologic disorders or hyperpermeability states.

The term "therapeutically effective amount" refers to an amount of a drug effective to treat a disease or disorder in a mammal. In the case of cancer, the therapeutically effective amount of the drug may reduce the number of cancer cells; reduce the tumor size; inhibit (i.e., slow to some extent and preferably stop) cancer cell infiltration into peripheral organs; inhibit (i.e., slow to some extent and preferably stop) tumor metastasis; inhibit, to some extent, tumor growth; and/or relieve to some extent one or more of the symptoms associated with the disorder. To the extent the drug may prevent growth and/or kill existing cancer cells, it may be cytostatic and/or cytotoxic. For cancer therapy, efficacy in vivo can, for example, be measured by assessing the duration of survival, time to disease progression (TTP), the response rates (RR), duration of response, and/or quality of life.

"Treatment" refers to both therapeutic treatment and prophylactic or preventative measures. Those in need of treatment include those already with the disorder as well as those in which the disorder is to be prevented.

The terms "cancer" and "cancerous" refer to or describe the physiological condition in mammals that is typically characterized by unregulated cell growth. Examples of cancer include but are not limited to, carcinoma, lymphoma, blastoma, sarcoma, and leukemia. More particular examples of such cancers include melanoma, lung, thyroid, breast, colon, prostate, hepatic, bladder, renal, cervical, pancreatic, leukemia, lymphoma, myeloid, ovarian, uterus, sarcoma, biliary, or endometrial cancer.

According to some embodiments, the antibody of the present invention is attached to a cytotoxic or therapeutic moiety. The cytotoxic or therapeutic moiety can be, for example, a cytotoxic moiety, a toxic moiety, a cytokine moiety, a bi-specific antibody moiety, a cytotoxin, a chemokine, a chemotherapy, a pro-apoptotic, interferon, a radioactive moiety, or combinations thereof, examples of which are provided infra.

The term "anti-neoplastic composition" refers to a composition useful in treating cancer comprising at least one active therapeutic agent capable of inhibiting or preventing tumor growth or function, and/or causing destruction of tumor cells. Therapeutic agents suitable in an anti-neoplastic composition for treating cancer include, but not limited to, chemotherapeutic agents, radioactive isotopes, toxins, cytokines such as interferons, and antagonistic agents targeting cytokines, cytokine receptors or antigens associated with tumor cells. Preferably the therapeutic agent is a chemotherapeutic agent.

As used herein the term "diagnosing" refers to determining presence or absence of a pathology, classifying a pathology or a symptom, determining a severity of the pathology, monitoring pathology progression, forecasting an outcome of a pathology and/or prospects of recovery.

Pharmacology

The present invention also contemplates pharmaceutical formulations for human medical use, which comprise as the active agent at least one antibody which recognizes CEACAM1, for the manufacture of a therapeutic or diagnostic composition for the treatment, diagnosis or prophylaxis of the conditions variously described herein.

In such pharmaceutical and medicament formulations, the active agent is preferably utilized together with one or more pharmaceutically acceptable carrier(s) and optionally any other therapeutic ingredients. The carrier(s) must be pharmaceutically acceptable in the sense of being compatible with the other ingredients of the formulation and not unduly deleterious to the recipient thereof. The active agent is provided in an amount effective to achieve the desired pharmacological effect, as described above, and in a quantity appropriate to achieve the desired daily dose.

Typically, the molecules of the present invention comprising the antigen binding portion of an antibody or comprising another polypeptide including a peptidomimetic will be suspended in a sterile saline solution for therapeutic uses. The pharmaceutical compositions may alternatively be formulated to control release of active ingredient (molecule comprising the antigen binding portion of an antibody) or to prolong its presence in a patient's system. Numerous suitable drug delivery systems are known and include, e.g., implantable drug release systems, hydrogels, hydroxymethylcellulose, microcapsules, liposomes, microemulsions, microspheres, and the like. Controlled release preparations can be prepared through the use of polymers to complex or adsorb the molecule according to the present invention. For example, biocompatible polymers include matrices of poly(ethylene-co-vinyl acetate) and matrices of a polyanhydride copolymer of a stearic acid dimer and sebaric acid. The rate of release of the molecule according to the present invention, i.e., of an antibody or antibody fragment, from such a matrix depends upon the molecular weight of the molecule, the amount of the molecule within the matrix, and the size of dispersed particles.

The pharmaceutical composition of this invention may be administered by any suitable means, such as orally, topically, intranasally, subcutaneously, intramuscularly, intravenously, intra-arterially, intraarticulary, intralesionally or parenterally. Ordinarily, intravenous (i.v.), intraarticular, topical or parenteral administration will be preferred.

It will be apparent to those of ordinary skill in the art that the therapeutically effective amount of the molecule according to the present invention will depend, inter alia upon the administration schedule, the unit dose of molecule administered, whether the molecule is administered in combination with other therapeutic agents, the immune status and health of the patient, the therapeutic activity of the molecule administered and the judgment of the treating physician. As used herein, a "therapeutically effective amount" refers to the amount of a molecule required to alleviate one or more symptoms associated with a disorder being treated over a period of time.

Although an appropriate dosage of a molecule of the invention varies depending on the administration route, type of molecule (polypeptide, polynucleotide, organic molecule etc.) age, body weight, sex, or conditions of the patient, and should be determined by the physician in the end, in the case of oral administration, the daily dosage can generally be between about 0.01 mg to about 500 mg, preferably about 0.01 mg to about 50 mg, more preferably about 0.1 mg to about 10 mg, per kg body weight. In the case of parenteral administration, the daily dosage can generally be between about 0.001 mg to about 100 mg, preferably about 0.001 mg to about 10 mg, more preferably about 0.01 mg to about 1 mg, per kg body weight. The daily dosage can be administered, for example in regimens typical of 1-4 individual administration daily. Other preferred methods of administration include intraarticular administration of about 0.01 mg to about 100 mg per kg body weight. Various considerations in arriving at an effective amount are described, e.g., in Goodman and Gilman's: The Pharmacological Bases of Therapeutics, 8th ed., Pergamon Press, 1990; and Remington's Pharmaceutical Sciences, 17th ed., Mack Publishing Co., Easton, Pa., 1990.

Suitable dosing regimens of combination chemotherapies are known in the art and described in, for example, Saltz et al. Proc ASCO 1999, 18, 233a and Douillard et al., Lancet 2000, 355, 1041-7.

The molecules of the present invention as active ingredients are dissolved, dispersed or admixed in an excipient that is pharmaceutically acceptable and compatible with the active ingredient as is well known. Suitable excipients are, for example, water, saline, phosphate buffered saline (PBS), dextrose, glycerol, ethanol, or the like and combinations thereof. Other suitable carriers are well known to those skilled in the art. In addition, if desired, the composition can contain minor amounts of auxiliary substances such as wetting or emulsifying agents, pH buffering agents.

The pharmaceutical composition according to the present invention may be administered together with an anti-neoplastic composition. According to a specific embodiment the anti-neoplastic composition comprises at least one chemotherapeutic agent. The chemotherapy agent, which could be administered together with the antibody according to the present invention, or separately, may comprise any such agent known in the art exhibiting anticancer activity, including but not limited to: mitoxantrone, topoisomerase inhibitors, spindle poison vincas: vinblastine, vincristine, vinorelbine (taxol), paclitaxel, docetaxel; alkylating agents: mechlorethamine, chlorambucil, cyclophosphamide, melphalan, ifosfamide; methotrexate; 6-mercaptopurine; 5-fluorouracil, cytarabine, gemcitabin; podophyllotoxins: etoposide, irinotecan, topotecan, dacarbazin; antibiotics: doxorubicin (adriamycin), bleomycin, mitomycin; nitrosoureas: carmustine (BCNU), lomustine, epirubicin, idarubicin, daunorubicin; inorganic ions: cisplatin, carboplatin; interferon, asparaginase; hormones: tamoxifen, leuprolide, flutamide, and megestrol acetate.

According to a specific embodiment, the chemotherapeutic agent is selected from the group consisting of alkylating agents, antimetabolites, folic acid analogs, pyrimidine analogs, purine analogs and related inhibitors, vinca alkaloids, epipodophyllotoxins, antibiotics, L-asparaginase, topoisomerase inhibitor, interferons, platinum coordination complexes, anthracenedione substituted urea, methyl hydrazine derivatives, adrenocortical suppressant, adrenocorticosteroides, progestins, estrogens, antiestrogen, androgens, antiandrogen, and gonadotropin-releasing hormone analog. According to another embodiment, the chemotherapeutic agent is selected from the group consisting of 5-fluorouracil (5-FU), leucovorin (LV), irenotecan, oxaliplatin, capecitabine, paclitaxel and doxetaxel. Two or more chemotherapeutic agents can be used in a cocktail to be administered in combination with administration of the anti-CEACAM1 antibody.

The following examples are intended to illustrate how to make and use the compounds and methods of this invention and are in no way to be construed as a limitation. Although the invention will now be described in conjunction with specific embodiments thereof, it is evident that many modifications and variations will be apparent to those skilled in the art. Accordingly, it is intended to embrace all such modifications and variations that fall within the spirit and broad scope of the appended claims.

EXAMPLES

Means for preparing and characterizing antibodies are well known in the art. A description follows as to exemplify techniques for the production, characterization and use of anti-CEACAM1 antibodies in accordance with the present invention.

Generally, the nomenclature used herein and the laboratory procedures utilized in the present invention include molecular, biochemical, microbiological and recombinant DNA techniques. Such techniques are thoroughly explained in the literature. See, for example, "Molecular Cloning: A laboratory Manual" Sambrook et al., 1989; "Current Protocols in Molecular Biology" Volumes I-III Ausubel, R. M., ed. 1994; Ausubel et al., "Current Protocols in Molecular Biology", John Wiley and Sons, Baltimore, Md. 1989; Perbal, "A Practical Guide to Molecular Cloning", John Wiley & Sons, New York 1988; Watson et al., "Recombinant DNA", Scientific American Books, New York; Birren et al. (eds) "Genome Analysis: A Laboratory Manual Series", Vols. 1-4, Cold Spring Harbor Laboratory Press, New York 1998; methodologies as set forth in U.S. Pat. Nos. 4,666,828; 4,683,202; 4,801,531; 5,192,659 and 5,272,057; "Cell Biology: A Laboratory Handbook", Volumes I-III Cellis, J. E., ed. 1994; "Current Protocols in Immunology" Volumes I-III Coligan J. E., ed. 1994; Stites et al. (eds), "Basic and Clinical Immunology" (8th Edition), Appleton & Lange, Norwalk, Conn. 1994; Mishell and Shiigi (eds), "Selected Methods in Cellular Immunology", W. H. Freeman and Co., New York 1980; available immunoassays are extensively described in the patent and scientific literature, see, for example, U.S. Pat. Nos. 3,791,932; 3,839,153; 3,850,752; 3,850,578; 3,853,987; 3,867,517; 3,879,262; 3,901,654; 3,935,074; 3,984,533; 3,996,345; 4,034,074; 4,098,876; 4,879,219; 5,011,771 and 5,281,521; "Oligonucleotide Synthesis" Gait, M. J., ed. (1984); "Nucleic Acid Hybridization" Hames, B. D., and Higgins S. J., eds. 1985; "Transcription and Translation" Hames, B. D., and Higgins S. J., Eds. 1984; "Animal Cell Culture" Freshney, R. I., ed. 1986; "Immobilized Cells and Enzymes" IRL Press, (1986); "A Practical Guide to Molecular Cloning" Perbal, B., 1984 and "Methods in Enzymology" Vol. 1-317, Academic Press; "PCR Protocols: A Guide To Methods And Applications", Academic Press, San Diego, Calif. 1990; Marshak et al., "Strategies for Protein Purification and Characterization—A Laboratory Course Manual" CSHL Press 1996. The procedures therein are believed to be well known in the art.

Example 1

Generation and Characterization of Monoclonal Antibodies which Recognized CEACAM Monoclonal antibodies that effectively block the CEACAM1 homophilic interactions in vitro at nanomolar concentrations were generated by immunizing mice with recombinant human CEACAM1 protein. Hybridomas producing the CEACAM1-blocking antibodies were produced and re-cloned several times to yield a stable clone.

The DNA and amino acid sequence of one exemplary monoclonal antibody which recognizes CEACAM1 was determined by Fusion Antibodies Ltd. mRNA was extracted from the hybridoma cell pellets and total RNA was extracted from the pellets using RNA extraction protocol. RT-PCR-cDNA was created from the RNA by reverse-transcription with an oligo(dT) primer. PCR reactions using variable domain primers were used to amplify both the VH and VL regions of the monoclonal antibody DNA.

The VH and VL products were cloned into the Invitrogen sequencing vector pCR2.1 and transformed into TOP10 for positive transformants. Selected colonies were picked and analyzed through sequencing. The resulted DNA and amino acid sequences determined are:

```
Variable heavy chain (VH)
DNA sequence of the VH domain:
                                              (SEQ ID NO: 25)
ATGGGATGGACCTTGGTCTTTCTCTTTCTCCTGTCAGTAACTGCAGGTGTTCACTC

CCAGGTCCAGCTGCAGCAGTCTGGAGCTGAGCTGGTAAGGCCTGGGACTTCAGT

GAAGGTGTCCTGCAAGGCTTCTGGATACGCCTTCACTAATAACTTGATAGAGTGG

GTAAAACAGAGGCCTGGACAGGGCCTTGAGTGGATTGGAGTGATTAATCCTGGA
```

-continued

```
AGTGGTGATACTAACTACAATGAGAAGTTCAAGGGCAAGGCAACACTGACTGCA

GACAAATCCTCCAACACTGCCTACATGCAGCTCAGCAGCCTGACATCTGATGACT

CTGCGGTCTATTTCTGTGCAAGAGGGGATTACTACGGTGGCTTTGCTGTGGACTA

CTGGGGTCAAGGAACCTCAGTCACCGTCTCCTCAGCCAAAACGACACCCCCATCC

GTTTATCCCTTGGCCCCTGGAAGCTTGGG.
```

Amino acid sequence of the VH domain:
(SEQ ID NO: 26)
QVQLQQSGAELVRPGTSVKVSCKASGYAFTNNLIEWVKQRPGQGLEWIGVINPGSG

DTNYNEKFKGKATLTADKSSNTAYMQLSSLTSDDSAVYFCARGDYYGGFAVDYWG

QGTSVTVSS.

Variable light chain (VL)
DNA sequence of the VL domain:
(SEQ ID NO: 27)
```
ATGGTGTCCTCAGCTCAGTTCCTTGGTCTCCTGTTGCTCTGTTTTCAAGGAACCAG

ATGTGATATCCAGATGACACAGACTACATCCTCCCTGTCTGCCTCTCTGGGAGAC

AGAGTCACCATCAGTTGCAGGACAAGTCAGGACATTGGCAATTATTTAAACTGG

TATCAGCAGAAACCAGATGGAACTGTTAAACTCCTGATCTACTACACATCAAGAT

TACACTCAGGAGTCCCATCAAGGTTCAGTGGCAGTGGGTCTGGAACAGATTATTC

TCTCACCATTAGCAACCTGGAGCAAGAAGATATTGCCACTTACTTTTGCCAACAG

GGTAAAAGCCTTCCTCGGACGTTCGGTGGAGGCACCAAGTTGGAAATCAAACGG

GCTGATGCTGCACCAACTGTATCCATCTTCCCACCATCCAGTGAGCAGTTAACAT

CTGGAGGTGCCTCAGTCGTGTGCTTCTTGAACAACTTCTACCCCAGAGA.
```

Amino acid sequence of the VL domain:
(SEQ ID NO: 28)
DIQMTQTTSSLSASLGDRVTISCRTSQDIGNYLNWYQQKPDGTVKLLIYYTSRLHSGV

PSRFSGSGSGTDYSLTISNLEQEDIATYFCQQGKSLPRTFGGGTKLEIK.

N-terminal amino-acid sequencing and Mass-Spectra analysis were used to confirm the VL and VH identities.

Example 2

Verification of N-terminal Amino Acid Sequence

Amino acid sequence analysis of the light chain was performed by the Edman degradation method to verify the N-terminus sequence of the light chain of one of the monoclonal antibodies. The obtained N-terminal sequence was: DIQMTQTTSS (SEQ ID NO: 29), which is in accordance with the N-terminal expected sequence based on the DNA sequence.

Example 3

Complementary Determining Region (CDR) Sequences

The CDR segments were identified using two different algorithm methods:
1. IMGT algorithm (Lefranc et al., 1999, Nucleic Acids Research, 27, 209-212);
2. KABAT algorithm (Wu T T and Kabat E. A., 1970, J. Exp. Med. 132, 211-250).

Table 1 summarizes the determined CDR sequences using the two methods as well as the minimal consensus sequence and combined sequence of sequences identified using both methods.

TABLE 1

| | | VH1 | VH2 | VH3 | VL1 | VL2 | VL3 |
|---|---|---|---|---|---|---|---|
| | | | | CDR sequences | | | |
| IMGT | | GYAFTNNL (SEQ ID NO: 13) | INPGSGDT (SEQ ID NO: 14) | ARGDYYGG FAVDY (SEQ ID NO: 15) | QDIGNY (SEQ ID NO: 16) | YTSR (SEQ ID NO: 17) | QQGKSLPR T (SEQ ID NO: 18) |
| KABAT | | NNLIE (SEQ ID NO: 7) | VINPGSGDT NYNEKFKG (SEQ ID NO: 8) | GDYYGGFA VDY (SEQ ID NO: 9) | RTSQDIGNY LN (SEQ ID NO: 10) | YTSRLHS (SEQ ID NO: 11) | QQGKSLP (SEQ ID NO: 12) |

TABLE 1-continued

| | CDR sequences | | | | | |
|---|---|---|---|---|---|---|
| | VH1 | VH2 | VH3 | VL1 | VL2 | VL3 |
| Combined sequence | GYAFTNNLIE (SEQ ID NO: 19) | VINPGSGDTNYNEKFKG (SEQ ID NO: 20) | ARGDYYGGFAVDY (SEQ ID NO: 21) | RTSQDIGNYLN (SEQ ID NO: 22) | YTSRLHS (SEQ ID NO: 23) | QQGKSLPRT (SEQ ID NO: 24) |
| Consensus sequence | X₁NNLX₂* (SEQ ID NO: 1) | INPGSGDT (SEQ ID NO: 2) | GDYYGGFAVDY (SEQ ID NO: 3) | QDIGNY (SEQ ID NO: 4) | YTSR (SEQ ID NO: 5) | QQGKSLP (SEQ ID NO: 6) |

*wherein X₁ is absent or is Thr (T) and X₂ is absent or is Ile (I)

Example 4

Design and Production of a Chimeric Monoclonal Antibody

The DNA sequence of the variable heavy and light chains (SEQ ID NOs 25 and 27) were used to construct a chimeric antibody, comprising the human IgG1 isotype constant domains and constant light (CL) human IgKappa domain. Although the parent monoclonal antibody is mouse IgG1 and its human equivalent is IgG4, a human IgG1 framework was used to construct some of the chimeric antibodies of the present invention. The DNA sequences for the light chain and heavy chain were synthesized and cloned into the expression vector pFUSION-DHFR1 under separate promoters.

Transient Transfection of CHO Cells

Suspension CHO cells (Invitrogen, UK) were cultivated at 130 rpm, 8% $CO_2$, 37° C. in Pro CHO 5 serum free medium (Lonza, UK) in 250 and 500 ml vented Erlenmeyer flasks (Corning, Netherlands). On the day of transfection, cells were seeded at a density of 2.0×106 cells/ml, 2.5 g/ml of plasmid DNA (Geneart, Germany) was transfected into the cells using Polyethylenimine (Polysciences Inc, PA, US). Transfected cultures were incubated at 130 rpm, 8% $CO_2$, 37° C. for 9-10 days. Prior to harvest of the culture supernatants were spinned at 4,000 rpm for 40 minutes.

Media was harvested and purified in two separate batches. The media was filtered through a 0.8 μm gyrodisc filter and purified using a 1 ml Protein A column. The antibody was purified by FPLC. 320 ml sample was loaded at 0.2 mls/min overnight and increased to 0.5 mls/min after 17 hours. Column was washed/equilibrated with PBS at 0.5 mls/min before elution with pH 3.0 Gly/HCL elution buffer. A good peak was observed and fractions 1 to 5 were quantified by Bradford Assay. The Bradford assay showed protein present in fractions 1-4 which were pooled and dialyzed for buffer exchange overnight in 1 liter of PBS (4° C., 120 RPM). A concentration of 1.823 mg/ml was observed for the 4 ml sample, therefore a total yield of approximately 7.32 mg was purified. In the second batch, the results of the Bradford assay showed protein present in fractions 1-3 which were pooled and dialyzed. From the 320 ml conditioned medium a total yield of approximately 7.32 mg was purified (batch A). From a 910 ml culture a total yield of approximately 15.74 mg was purified (batch B). Total transient expression yielded about 23 mg of purified protein. After concentration determinations and SDS/PAGE analysis, 19.65 mg of the chimeric antibody were yielded. The purified antibody samples were analyzed by SDS-PAGE to assess purity. FIG. 1 depicts the SDS-PAGE gel image showing light and heavy chains of the chimeric antibody. MS analysis revealed that the molecular weight of CM10 heavy chain is 48.6 KDa and of light chain is 23.3 KDa.

The resulted antibody, denoted CM10, has the following amino acid sequence of the heavy and light chains:

Heavy chain amino acid sequence (without signal peptide):
(SEQ ID NO: 30)
QVQLQQSGAELVRPGTSVKVSCKAS<u>GYAFTNNL</u>IEWVKQRPGQGLEWIGV<u>INPGSG</u>

<u>DTNYNEKFKG</u>KATLTADKSSNTAYMQLSSLTSDDSAVYFC<u>ARGDYYGGFAVDY</u>WG

QGTSVTVSSASTKGPSVFPLAPSSKSTSGGTAALGCLVKDYFPEPVTVSWNSGALTSGV

HTFPAVLQSSGLYSLSSVVTVPSSSLGTQTYICNVNHKPSNTKVDKKVEPKSCDKTHTCP

PCPAPELLGGPSVFLFPPKPKDTLMISRTPEVTCVVVDVSHEDPEVKFNWYVDGVEVHN

AKTKPREEQYNSTYRVVSVLTVLHQDWLNGKEYKCKVSNKALPAPIEKTISKAKGQPRE

PQVYTLPPSRDELTKNQVSLTCLVKGFYPSDIAVEWESNGQPENNYKTTPPVLDSDGSFF

LYSKLTVDKSRWQQGNVFSCSVMHEALHNHYTQKSLSLSPGK.

Variable domain is in bold, CDRs according to IMGT are underlined.

Light chain amino acid sequence (without signal peptide):
(SEQ ID NO: 31)
DIQMTQTTSSLSASLGDRVTISCRTS<u>QDIGNY</u>LNWYQQKPDGTVKLLIY<u>YTSRLHSG</u>

VPSRFSGSGSGTDYSLTISNLEQEDIATYFC<u>QQGKSLPRT</u>FGGGTKLEIKRTVAAPSV

```
-continued
FIFPPSDEQLKSGTASVVCLLNNFYPREAKVQWKVDNALQSGNSQESVTEQDSKDSTYSL

SSTLTLSKADYEKHKVYACEVTHQGLSSPVTKSFNRGEC
```

Variable domain is in bold, CDRs according to IMGT are underlined.

A plasmid containing the DNA sequences of the heavy and light chains of an exemplary chimeric monoclonal antibody denoted CM10 was deposited on Sep. 28, 2011 under ATCC Accession Number PTA-12130.

Example 5

Affinity Characterization of the Chimeric Monoclonal Antibody CM10

Binding of CM10 to Purified Human CEACAM1

Figure 2:
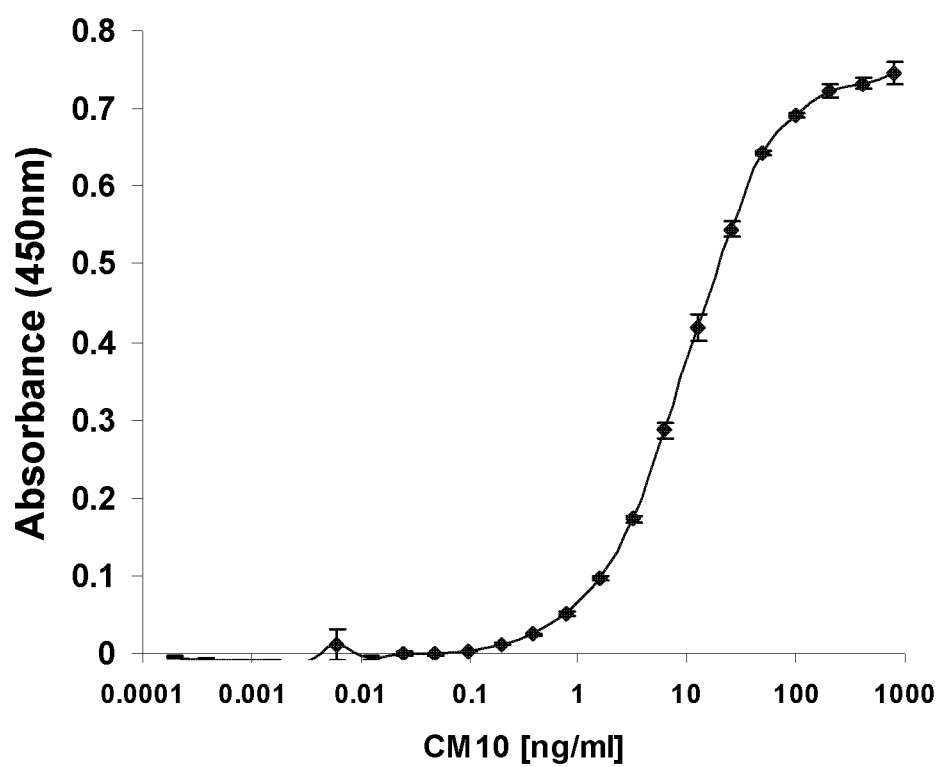
FIG. 2 shows specific binding curve of CM10 to purified hCEACAM1.

The binding specificity of CM10 to human CEACAM1 was tested in ELISA assay using purified human CEACAM1. Indirect ELISA using 23 double dilutions of CM10 were used to generate specific binding curve. The results shown in FIG. 2 represent average O.D. from triplicate±SE. Similar results were obtain from other ten independent experiments.

In order to test whether the chimerization process affect the binding affinity of the antibody, the chimeric antibody CM10 was evaluated for CEACAM1 binding by competitive ELISA and by BIAcore analysis.

For the ELISA, recombinant purified human CEACAM1 was bound to the plate. The chemically biotinylated CM10 was used as tracer at a constant concentration and was competed with increasing concentrations of unlabelled CM10. Following incubation and washing, the plate was developed with a StrepAvidin-HRP conjugate and the color reaction was developed with TMB as an HRP substrate.

Using 50 ng/ml of tracer, the apparent affinity values detected for CM10 were 1.2-1.6 nM.

BIAcore Analysis

Each antibody was immobilized onto a single channel of a CM5 sensor chip of Biacore3000 instrument by NHS-EDC coupling chemistry.

Recombinant CEACAM1 was flowed at 50 µl/min over the chip in various concentrations (0.19, 0.39, 0.78, 1.56, 3.12, 6.25, 12.5 and 25 nM). The running buffer was PBS-ET (10 mM p-buffer pH7.4, 150 mM NaCl, 3.4 mM EDTA and 0.005% tween 20). The data were analyzed using BIAEvaluation software 3.0 and the KD values of CM10-CEACAM1 affinity, calculated from three independent experiments were (KD): 4.07-5.05 nM (average 4.56 nM).

Binding Specificity of CM10 to Membrane-bound Endogenous CEACAM1

In order to test the binding of CM10 to membrane-bound endogenous CEACAM1, a FACS analysis was performed. Several human melanoma cell lines were screened for hCEACAM1 expression while 526mel cell line was used as positive control and 003mel as negative control line. 526mel, 003mel, Malme 3M, Skmel 5 and A375 cell lines were stained with CM10. Empty histograms represent mAb staining while darker histograms represent background staining. At least 5000 cells were used to analyze CEACAM1 expression in each histogram.

Figure 3:
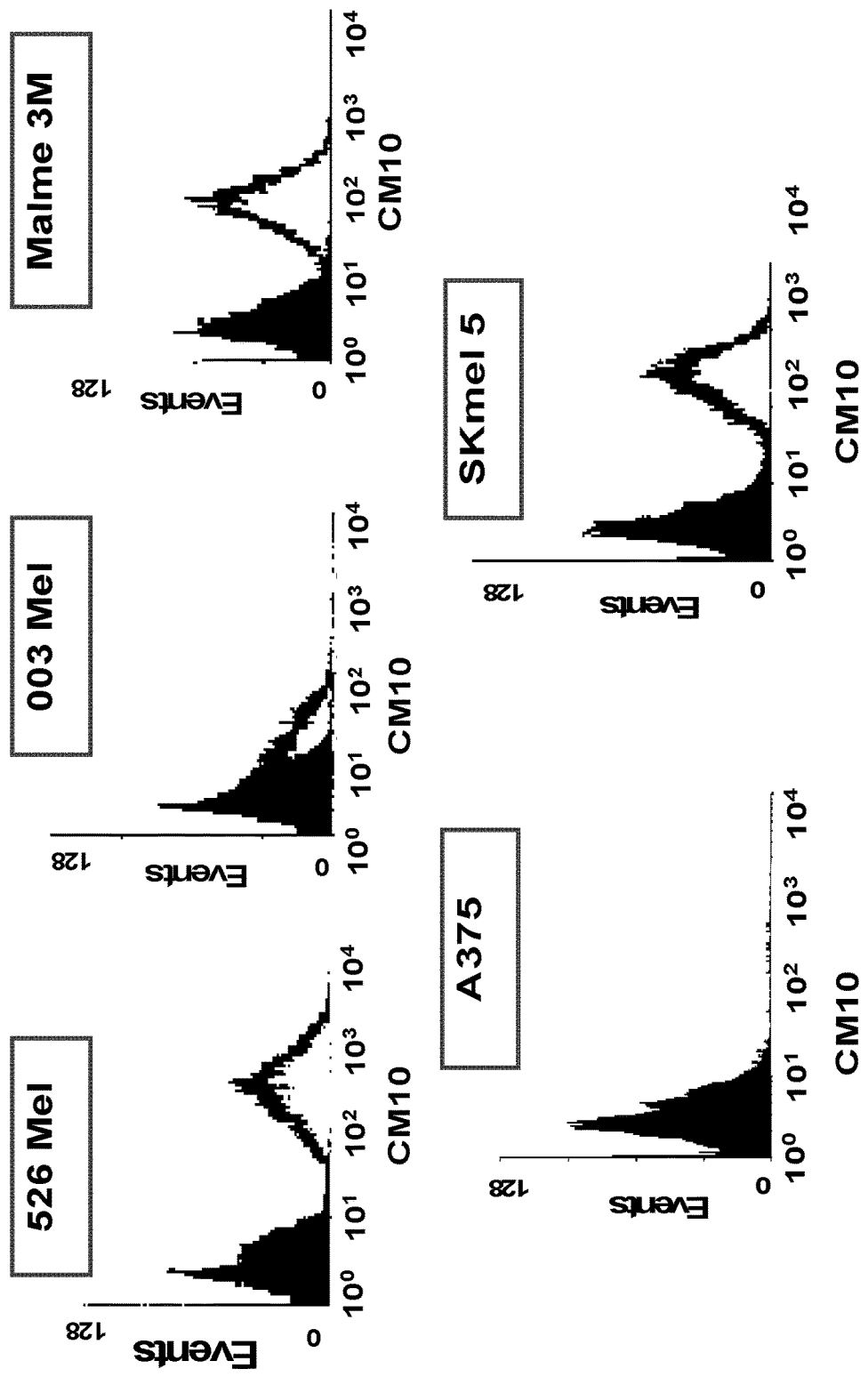
FIG. 3 demonstrates specific binding of CM10 to CEACAM1 as detected by Flow Cytometry analysis.

As can be appreciated from FIG. 3, CM10 detects membrane-bound endogenous CEACAM1. Malme3M and Skmel5 cell lines showed high expression of CEACAM1 while no expression could be detected in A375 melanoma cell-line.

Conclusion

The chimerization process was carried out successfully. The chimeric antibody bind CEACAM1 in an affinity of 1.4 nM as validated by two different approaches The FACS analysis testing the binding specificity of CM10 to various melanoma cell lines, demonstrate that the antibody retained its biological binding ability.

Example 6

Assessing the Activity of CM10

Blocking Cell-cell Interaction Assay

The assay which determines the ability of anti CEACAM1 mAb to blocks CEACAM1 cell-cell interaction uses murine T cells (BW cells) that are stably transfected with a chimeric molecule composed of the extracellular portion of human CEACAM1 fused to mouse z-chain (BW/CEACAM1). Engagement of CEACAM1 by co-incubation of BW/CEACAM1 cells with B cells stably transfected with CEACAM1 (221/CEACAM1), lead to the secretion of mouse IL-2, mediated by the z-chain.

Figure 4:
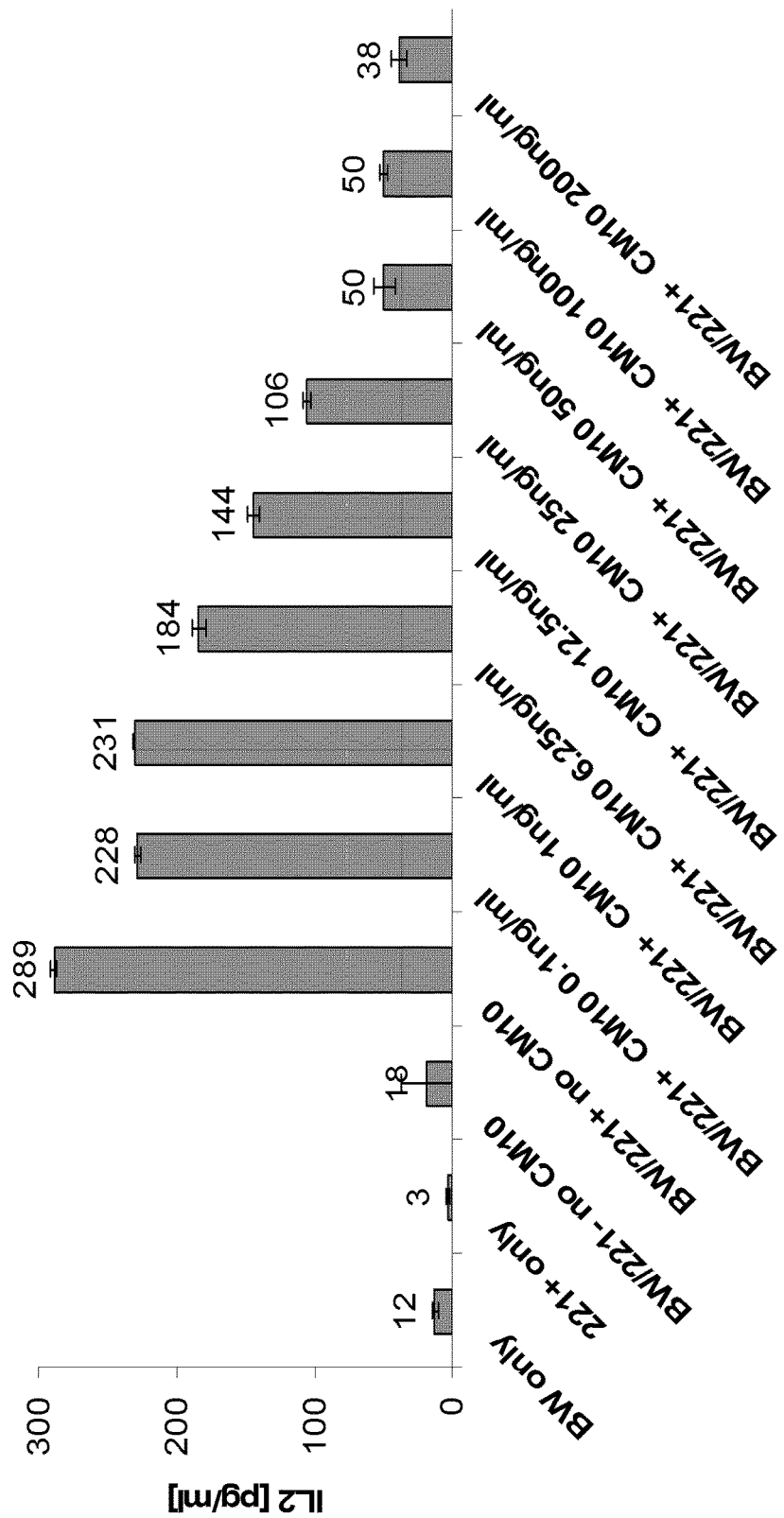
FIG. 4 confirms that CM10 blocks CEACAM1-CEACAM1 interaction between cells. Mouse IL-2 secretion of effectors cells (BW/221 cells expressing CEACAM1) incubated in the presence of various CM10 concentrations, was measured by ELISA.

Effectors cells (BW, expressing CEACAM1) were incubated in the presence of CM10 or PBS for 30 minutes on ice. Following the incubation the effectors cells were co-culture over night with target cell expressing CEACAM1 (221+) or negative to CEACAM1 (221−). Mouse IL-2 secretion was measured by commercial ELISA. The results shown in FIG. 4 represent average IL-2 secretion from duplicate wells. As shown in the figure, upon addition of CM10, CEACAM1-mediated cell-cell interactions between T and B cells were abolished in a dose-depended manner as indicated by blockage of IL-2 secretion.

In-vitro Immunomodulatory Killing Assays

T cells Killing assay: Melanoma-reactive T cells TILs (Tumor Infiltrating Lymphocytes, derived from melanoma patients) can destroy melanoma cells with matched HLA. TILs were purchased from ELLA Institute at Shiba medical center and were growth according to the clinical lab protocols. CFSE-labeled melanoma cells (SKmel5) were pre-incubated with CM10 (10 µg/ml) for 30 minutes on ice. TIL were added for additional 10 hours incubation at 37° C. Percentage of killing was determined by PI-staining of the CFSE labeled melanoma cells. Effector-to-target ratio was 5:1. In another assay, CFSE-labeled melanoma cells were pre-incubated with CM10 for 30 minutes on ice. TIL were added for additional 5 hours incubation at 37° C. Percentage of killing was determined by PI-staining of the CFSE labeled melanoma cells. Results represent average of % specific killing from triplicate wells±SE per treatment. Effector-to-target ratio was 5:1.

Figure 5:
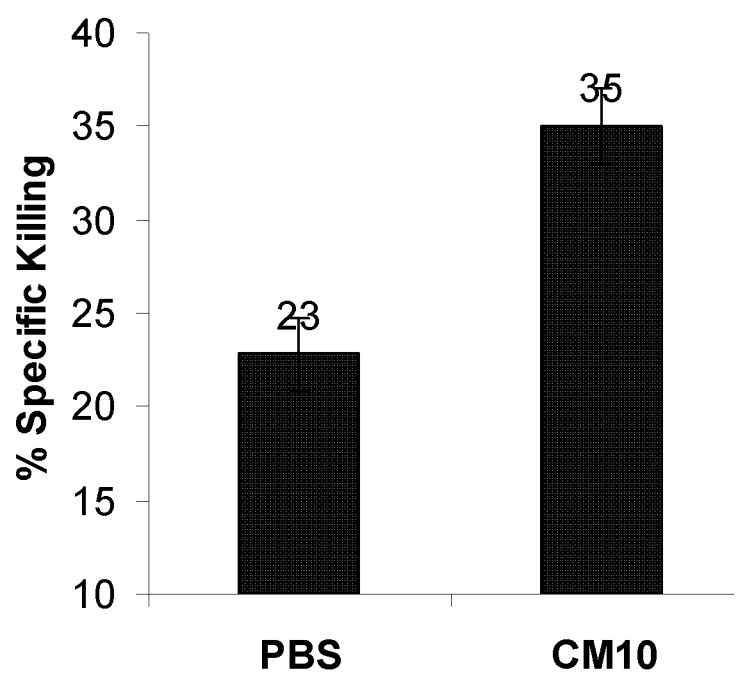
FIG. 5 shows CM10 enhancement of the specific killing activity of CEACAM1-positive melanoma cells.
Figure 6:
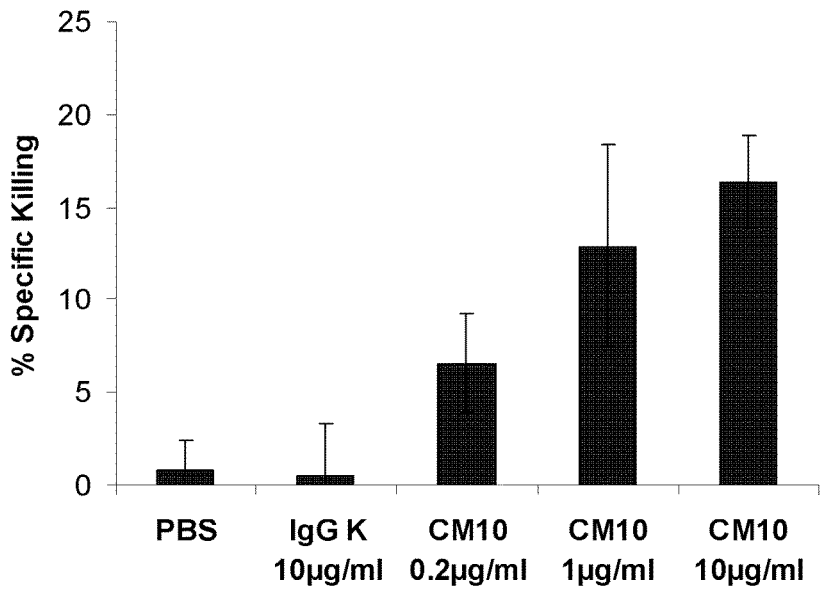
FIG. 6 demonstrates that CM10 stimulates the killing activity of tumor-infiltrating lymphocyte (TILs).

The results describes in FIG. 5 show that the killing activity of T cells is enhanced in the presence of the anti CEACAM1 mAb, CM10. Furthermore, in assay conditions where TILs where unable to kill any melanoma cells (short incubation or low TIL ratio), addition of CM10 stimulated the killing activity of TILs while no killing could be detected with IgG1 isotype control (FIG. 6).

NK Cells Killing Assay

Natural killer cells (NK cells) are a type of cytotoxic lymphocyte that can destroy malignant cells by releasing small proteins called perforin and granzyme that cause the target cell to die by apoptosis. NK cells can by activated throw several different pathways among them cytokines, FC receptor, and MHC class 1 absence at the target cells. Several activation and inhibition receptors to various ligands on target cells regulate the final cytoxicity activity of NK cells. NK 92MI cells are IL-2 independent NK cell line that were purchased from the ATCC.

NK 92MI were incubated with CM10 (0.2 µg/ml, 1 µg/ml or 5 µg/ml) or isotype match control Ab (5 µg/ml) for 30 minutes at 37° C., target cells expressing CEACAM1 were added for additional 5 hours. Percentage of killing was determined by classical LDH release assay. Results represent average of % cytotoxicity from triplicate wells±SE per treatment. Effector-to-target ratio was 2.5:1.

Figure 7:
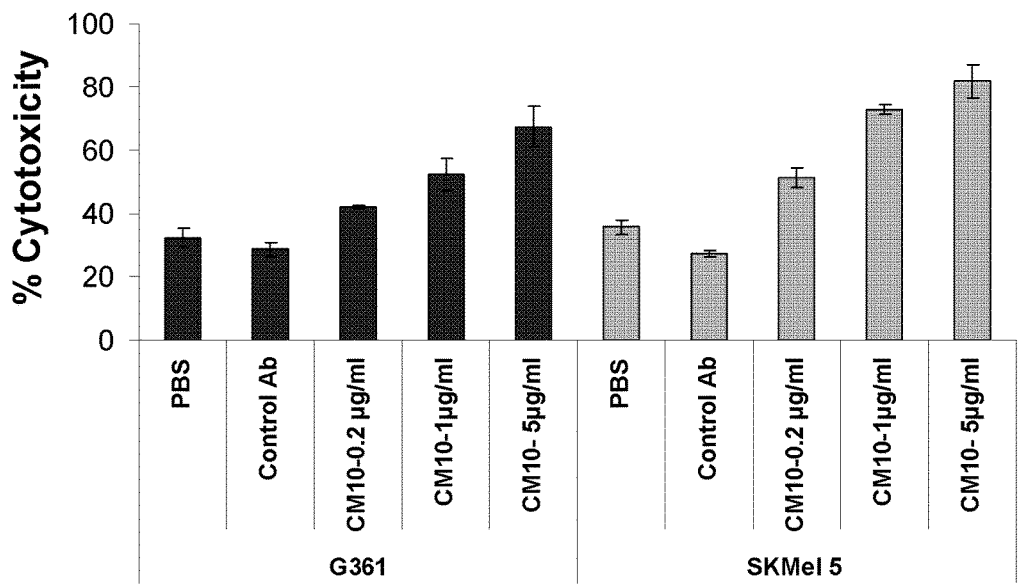
FIG. 7 demonstrates that CM10 enhances the killing activity of NK cells on CEACAM1 positive melanoma cell lines.

The assay describes in FIG. 7 shows that CM10 strongly enhanced the killing activity of NK cells on two melanoma cell lines expressing CEACAM1 (SKMel 5 and G361), compare to PBS or isotype match IgG. Similar results have been demonstrated in two other CEACAM1+ melanoma cell lines and in various effector-to-target (E:T) ratios.

Antibody-Dependent Cell-mediated Cytotoxicity

Antibody-Dependent Cell-Mediated Cytotoxicity (ADCC) is a mechanism of cell-mediated immunity whereby an effectors cell of the immune system (mostly NK cells) actively lyses target cells that has been bound by a specific antibody. In order to access the safety profile of CM10 we have conducted preliminary ADCC assay where the ability of CM10 to induce ADCC was examined in three melanoma cell lines (CEACAM1 positive cell lines: G361 and SKmel5 and CEACAM1 negative cell line: SKmel28).

The ability of CM10 to induce ADCC was examined in comparison to a positive control antibody (Polyclonal Ab anti CEACAM1 that showed ADCC activity in preliminary experiment). Isotype matched antibody served as negative control (hIgG1 K). The results indicate that CM10 do not trigger ADCC in the setting tested.

Complement-Dependent Cytotoxicity

Complement proteins are found in the blood, and their action "complements" the work of antibodies. Complement-dependent cytotoxicity (CDC) is a mechanism of killing cells in which antibody bound to the target cell surface fixes complement, results in assembly of the membrane attack complex that create pores in the target cell membrane and finally lead to cell lyses.

Figure 14:
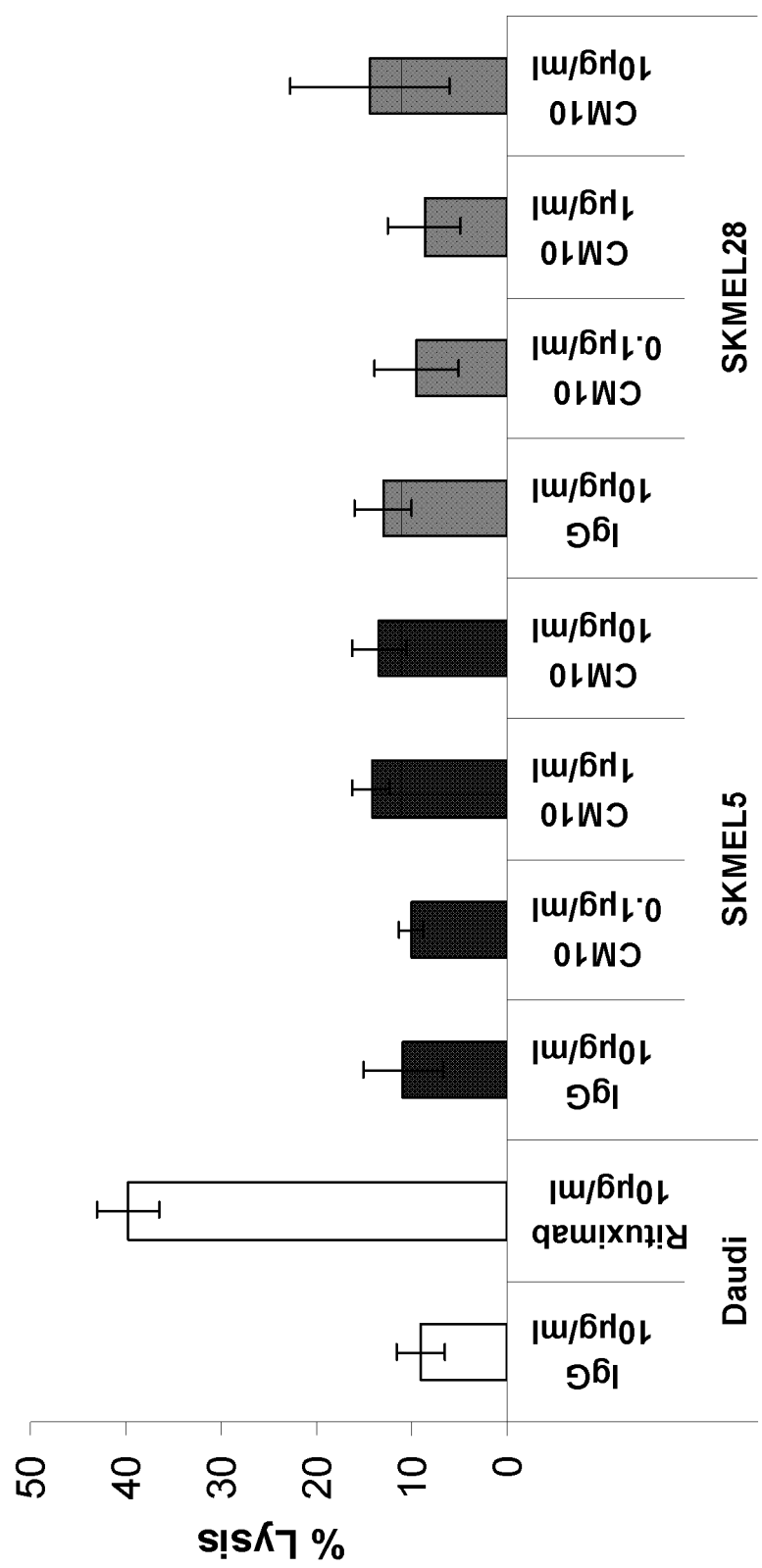
FIG. 14 represents results of complement-dependent cytotoxicity (CDC) assay in melanoma cell lines.

In order to access the safety profile of CM10, the ability of CM10 to induce CDC was examined in two melanoma cell lines (SKmel28 and SKmel5) expressing CEACAM1. Commercial pooled human serum was used as complement proteins source. The commercial monoclonal antibody Rituximab incubated with Daudi cells was used as the assay positive control and commercial IgG1K as isotype match control to CM10. Melanoma cell lines—SKMEL5 and SKMEL28 or positive control Daudi cells were incubated with CM10 or Rituxiamab respectively for 1 hour in room temperature followed by the addition of normal human serum at a final concentration of 50% for 2 additional hours in a humidified incubator (37° C., 5% $CO_2$). The percent of lysed cells was determined by Propidium iodine (PI) staining. The results (FIG. 14) represent the average+S.E of 2 individual experiments preformed in duplicates, indicating that CM10 did not induce CDC lysis in the setting tested.

In-vivo Efficacy Experiment

The purpose of this experiment is to test the direct effect of CM10 on melanoma cells in-vivo, as well as to evaluate the immunomodulatory effect, which is missing in the xenograft setting.

Calibration of Xenograft Experiments

CEACAM1 positive human melanoma cell line purchased from "ATCC" (SKMel5) and NOD-SCID, age matched mice from "Harlan laboratories" were used. The calibration assay was conducted in order to monitor the growth of the tumors and to find the optimal TILs regime. SKMel5 melanoma cells were injected SC (subcutaneous) to SCID-NOD mice and tumor volume was monitored by physical measurements. When the tumor volume reached 100 mm^3, the mice where divided into 5 randomized groups. The TILs were injected either IT (Intra Tumoral) at two different concentrations or IV (Intra Venus) at one concentration (20×10^6 per mice) while one group received only one injection and the second group received 2 TIL injections. Each TIL injection was followed by 5 days of hIL-2 administration. The calibration experiment demonstrated that TIL IV injection has higher effect on tumor size than IT administration. In addition repetitive TIL regime provides better tumor growth inhibition over single injection, as could be predicted from T cells half life. Based on this data, TIL will be administrated every 10 days by IV injections, in future xenograft experiments.

In-vivo Immunomodulatory, Anti-cancer Activity of CM10

Figure 8:
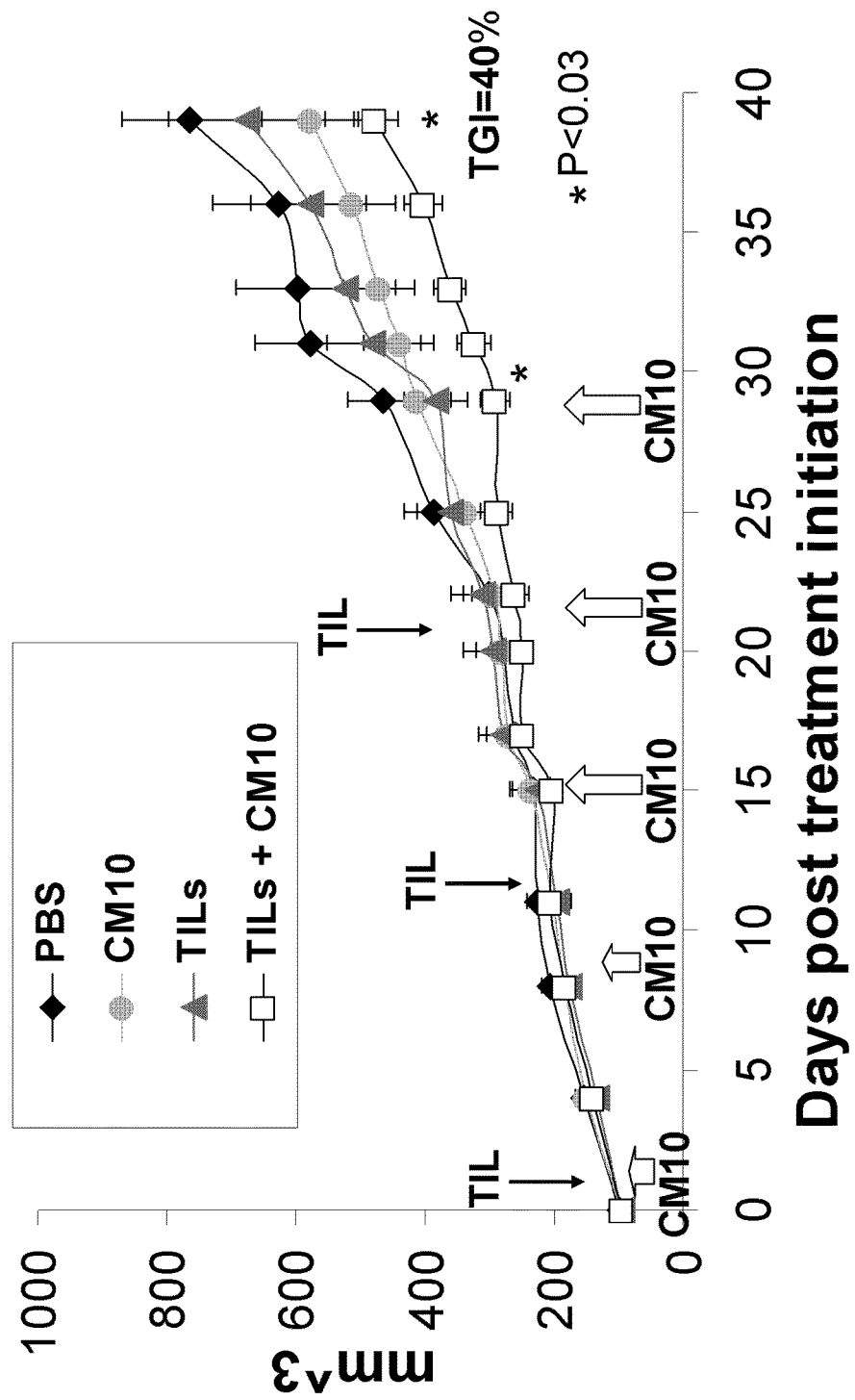
FIG. 8 CM10 immunomodulatory effect inhibits tumor growth in-vivo. Arrows indicate time of administration (CM10 circles, TIL triangles, CM10 and TIL open squares).

Human CEACAM1 positive SKmel5 melanoma cells were injected SC to SCID-NOD mice. When the tumors reached a volume of approximately 100 $mm^3$, the mice were randomized to one of the following treatment groups: a) Weekly IV injections of PBS; b) Weekly IV injections of 0.45 mg CM10; c) Three IV injection of $20\times10^6$ anti-tumor reactive human T cells (TIL) and weekly IV injections of PBS; d) Three IV injections of $20\times10^6$ anti-tumor reactive human T cells and weekly IV injections of 0.45 mg CM10. A person blind to the experimental setting measured the tumors volume 2-3 times per week. The results of FIG. 8 represent average tumor volume±SE from 6-10 mice per group. Arrows indicate time of administration (CM10 circle, TIL triangles, CM10 and TIL open squares). As shown, a moderate inhibition of tumor growth was observed either with CM10 alone or with TIL only, but the differences did not reach statistical significance when compared to the control treatment. Strikingly, the combination of adoptive human T cell transfer with CM10 injections exhibited significant synergism and strongly inhibited xenograft growth. This observation concurs with the in-vitro data showing the potentiating effect of CM10 on T cell killing (FIGS. 5 and 6).

Significant growth inhibition was observed in the group treated with CM10 in the presence of TIL. These results reinforce the immunostimulatory effect of anti CEACAM1 mAb in different cell lines, and indicate that CM10 can be used as promising immunomodulatory antibody. This observation concurs with the in-vitro data showing the stimulatory effect of CM10 on melanoma cells killing by T cell.

Conclusions

CEACAM1 is known as a regulator of lymphocyte activation. CM10 is an antibody that blocks the interactions between two CEACAM1 molecules (FIG. 4) and therefore eliminates the inhibitory signals mediated by CEACAM1, results in stronger cytotoxic lymphocytes activation against tumor cells (FIGS. 6 and 7). The in-vivo xenograft result (FIG. 8) reinforce the immunomostimulatory nature of CM10 and demonstrate significant growth inhibition of tumors in mice treated with CM10 in the presence of TIL.

Figure 9:
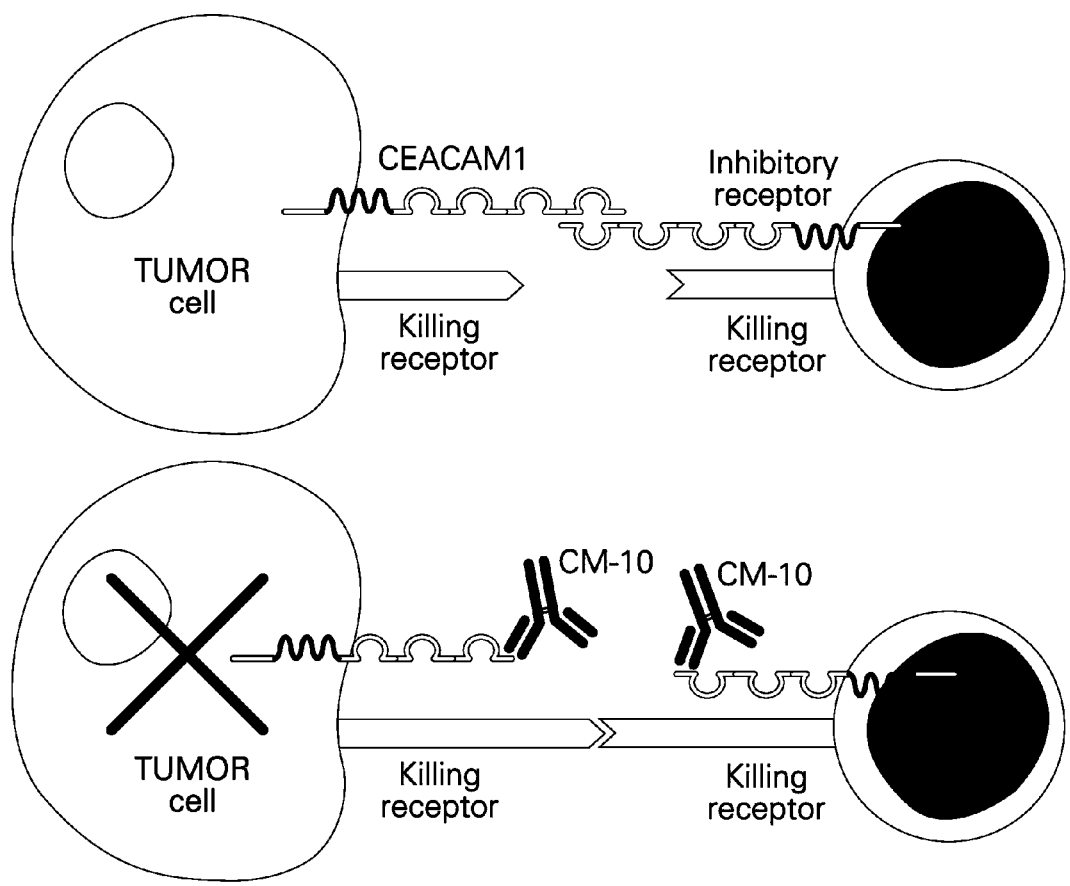
FIG. 9 is a schematic presentation of CM10 immunomodulatory mode of action.

The scheme presented in FIG. 9 demonstrates a non-limitative theory of the mode of action of CM10 that prevents CEACAM1-CEACAM1 interaction enabling activation of killing signals by immune system cells.

Example 7

CM10 In-vitro Safety Assessment

The Effect of CM10 on Normal Human Cells

In order to evade from the immune system cancer cells alter the expression of many molecules. Several evidences have showed that CEACAM1 expression is increasing during the malignance transformation of melanoma cells. According to the literature CEACAM1 is also expressed on normal cells, therefore it is important to map the possible binding sites of CM10 in the body and to identify if binding of CM10 to normal cells may lead to any undesired outcome.

Normal Human Tissues Cross Reactivity

Figure 10:
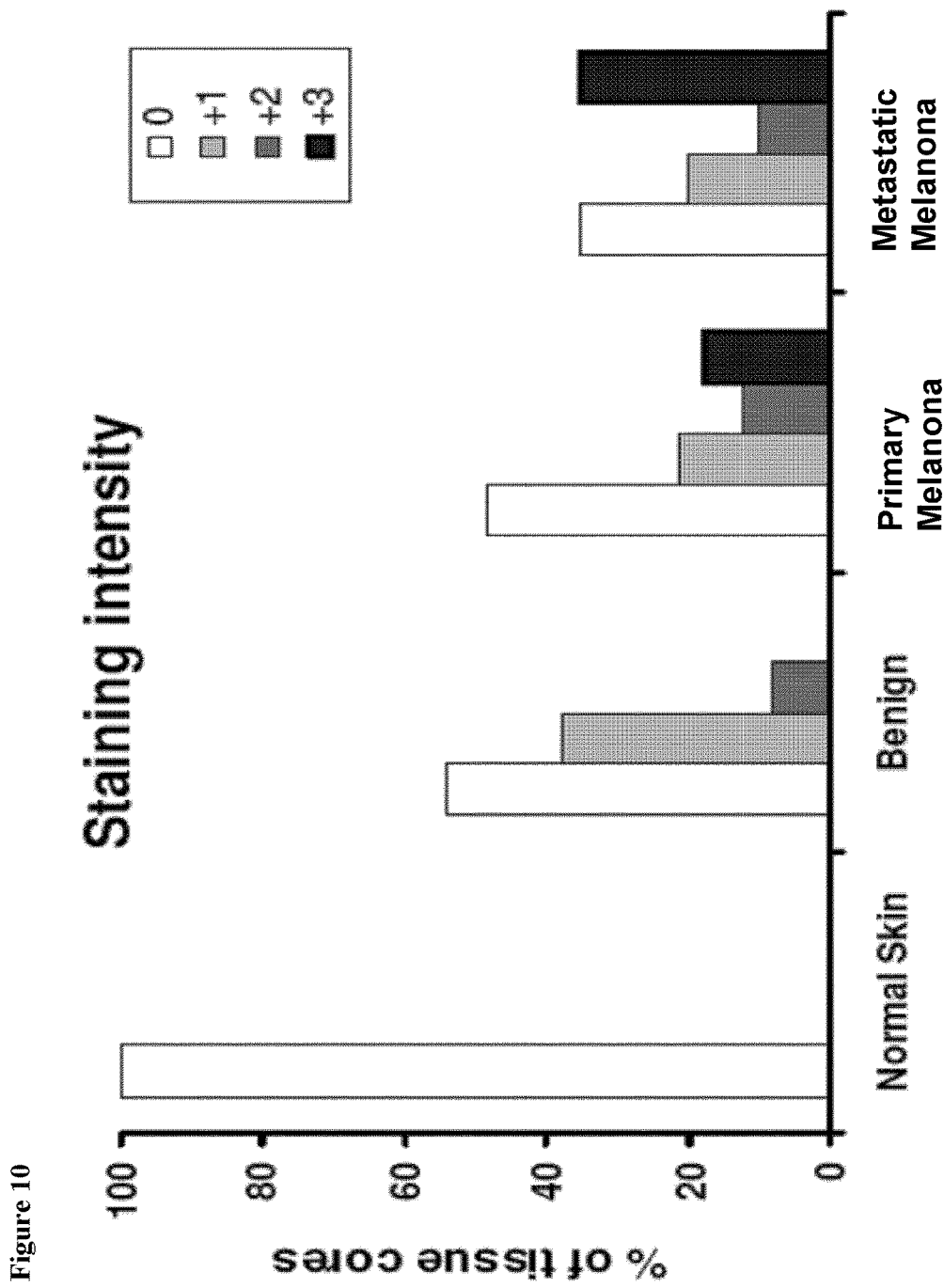
FIG. 10 represents CEACAM1 binding intensity level in tumors as determined by anti CEACAM1 antibody.

In this study, the binding intensity of anti-CEACAM1 mAb in a human tissue microarray containing normal and malignant melanoma samples was examined. The binding intensity was assessed using a standard pathological scoring system. Tissue micro array (TMA) containing 100 cases of malignant melanoma (primary, metastasis) and of benign nevi were analyzed for anti CEACAM1 binding intensity by standard IHC procedure. Each core of tumor was graded from 0 to +3. As shown in FIG. 10, binding intensity of anti-CEACAM1 mAb was seen in more than 50% of the melanoma samples and in 65% of metastatic melanoma samples.

The multi normal human organ tissue microarray (TMA) included 33 types of normal organs, each type taken from 3 normal human individuals. The age ranged from 2-67 years, 43 specimens were derived females and 57 specimens from males. The following tissues were negative for anti-CEACAM1 mAb binding: Cerebrum, cerebellum, ovary, pancreas, parathyroid gland, hypophysis, thyroid gland, tonsil, bone marrow, spleen, thymus, lung, cardiac muscle, stomach, skeletal muscle, skin, peripheral nerves, mesothelium and retina. A cell-specific staining was detected in some organs, mainly on the luminal side of epithelial cells forming ducts or glands in hollow visceral organs such as: brush border of small intestine; some apical colonic glands; Breast ductal epithelium; Liver bile canaliuculi; inner surface of renal tubules; few Endometrial glands; luminal part of Salivary gland. In addition, some low cellular staining was observed in adrenal gland cortex, apical surface of prostatic glands, Leidig cells of testis and single scattered cells in the pancreas. The only cells of the immune system that found positive were neutrophils within capillaries. No staining of lymphocytes was found in tissues and lymphatic organs. Finally, weak to moderate positive staining was found in endothelial cells of small blood vessels at selective sites, including: ovary, adrenal gland, kidney, and rarely in pancreas, prostate, hypophysis and endometrium.

The IHC analysis showed a strong anti CEACAM1 staining of melanoma cells, as compared to no staining of the vast majority of the tissues tested in a normal human tissue. Nevertheless, some selective staining was observed in the luminal aspect of epithelial cells of ducts or glands in hollow viscera. This cellular aspect is generally less accessible to an antibody administered via the peripherally blood.

Quantification of CM10 Molecules Bound per Cell

In order to quantify the exact number of CM10 molecules bound to each cell types the QuantiBRITE kit was used. Using the kit the MFI (mean florescence intensity) was directly translated to the number of molecules bound per cell. Three human primary cells of tissues, which were found to be positive for anti-CEACAM1 binding, were purchased from ATCC. HUVEC cells to represent the positive staining found in endothelial cells; primary prostate epithelial cells, since the apical surface of prostate glands showed positive staining, and primary renal proximal tubule epithelial cells since the inner surface of tubules stained positive. In more details, SkMel 5, G361, Malme 3M, NK 92MI, HUVEC, Renal primary cells and prostate primary cells were grown according to ATCC protocols. CM10 was conjugated to a PE molecule (RPE LYNX Rapid Conjugation Kits Serotec) according to the manufacture's protocol and was used (1 µg/ml) with the QuantiBRITE PE beads kit (BD) to determine the ABC (antibodies bound per cell) by Flow cytometry. The number of CM10 molecules bound per cell was analyzed using flow cytometry in the indicated primary cells in comparison to melanoma cell lines. At least 10000 cells were counted for each cell line.

Quantitative analysis (FIG. 11, the results represent the average of 2-3 independent experiments±SE) showed that the CEACAM1-positive melanoma cells bind between 20,000-50,000 CM10 molecules, while normal endothelial and epithelial cells (e.g. HUVEC, Kidney and Prostate) which have been reported to exert some CEACAM1 expression, bind up to 2,000 CM10 molecules only. Furthermore, high numbers of CM10 antibodies were bound to the NK cells (~20000) which correlates with published data showing high CEACAM1 expression on activated lymphocytes. These results reinforce the safety profile of CM10 (low expression on primary cells) and its activity (NK results) as a player in activated lymphocyte-mediated cell lysis.

Proliferation of Human Primary Cells in the Presence of CM10

Since some positive staining was found in normal tissues the effect of CM10 on primary cell growth was examined. HUVEC and primary prostate cells were grown according to the ATCC protocols and were monitored for cell proliferation using XTT standard assay. No effect on cell-proliferation could be detected.

Summary

Figure 11:
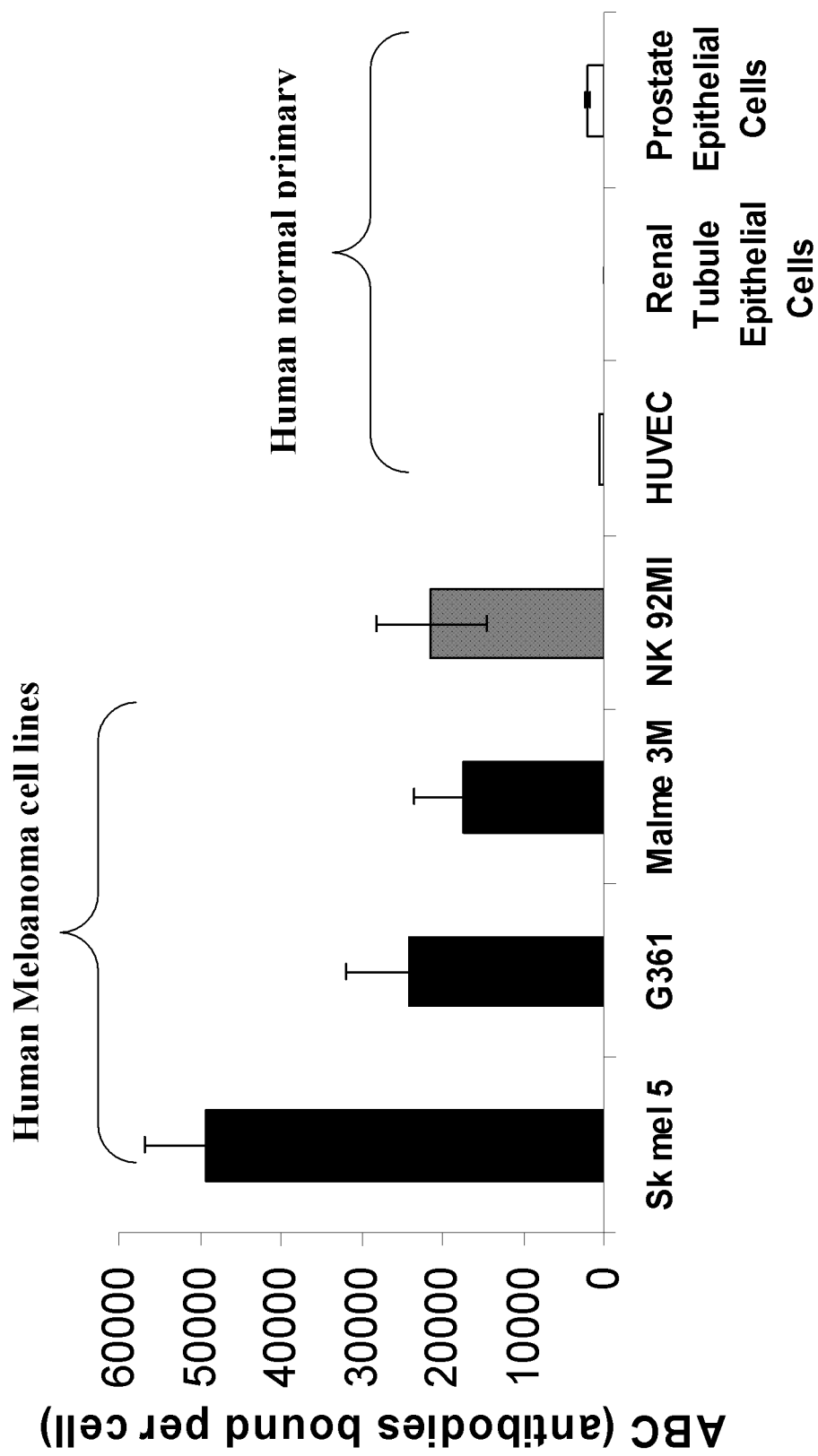
FIG. 11 shows quantification of CM10 molecules bound per cell.

The binding profile of anti CEACAM1 mAb to normal tissues and melanomas cells was identified. CEACAM1 is absence on normal melanocytes but undergoes neo-expression and is widely expressed on the vast majority of metastatic melanoma specimens (FIG. 10), in other normal organ there is restricted expression of CEACAM1 in specific cells within several tissues. A quantitative analysis, measuring the number of CM10 molecules that are bound to cells, revealed a very low numbers of bound-CM10 on normal human primary cell (FIG. 11). These results imply that the majority of CM10 molecule injected to patients will mainly target cancer cells and not normal tissues due to expression differences. Furthermore, CM10 has no effect on cell proliferation, CDC activity, and negligible or low ADCC activity which suggests that the binding of CM10 to non-target cells, would not result in unwanted cell outcome.

The Effect of CM10 on the Immune System

CM10 is an immunostimulatory antibody that blocks the interaction between two CEACAM1 molecules and by doing so mediates stimulation of lymphocytes against malignant cells. It is important to verify that the antibody will not cause unleashed stimulation of the immune system which can cause severe adverse events. In normal lymphocytes there is a neglect expression of CEACAM1 on the cell membrane, only following cell activation CEACAM1 is mobilized to the membrane, where it rapidly and strongly up-regulated on activated lymphocytes (Gray-Owen and Blumberg 2006, Nat Rev Immunol 6, 433-46). As demonstrated above, no cross reactivity to normal lymphatic tissues (Spleen, Thymus, Bone Marrow) or to lymphocytes was observed; nevertheless various in-vitro and ex-vivo immuno-toxicity analyses were performed to help in predicting potential side effects.

The Effect of CM10 on Human Lymphocytes Proliferation

Figure 12:
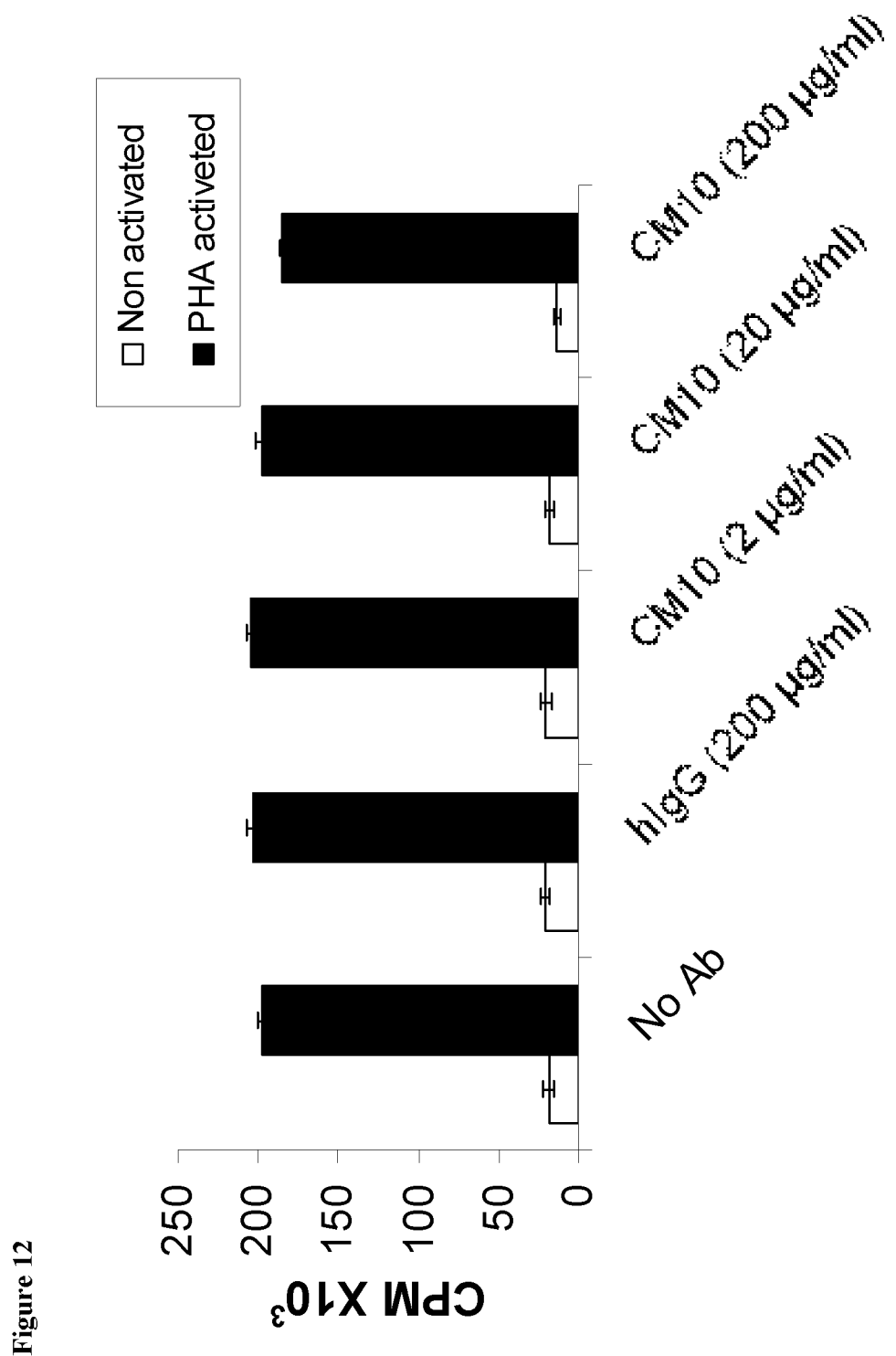
FIG. 12 confirms that CM10 has no effect on PBMC Proliferation. Results represent average proliferation rates from three donors for each treatment.

One of the most common and acceptable ways to evaluate safety of immunomodulatory antibodies in-vitro is by examine its effects on proliferation and cytokine secretion of normal human PBMC (peripheral blood mononuclear cells). Human PBMC from 3 unrelated donors were isolated and incubated with CM10 using 3 different concentrations (2 µg/ml, 20 µg/ml or 200 µg/ml) or with a control mAb IgG1K (200 µg/ml) for 60 minutes and with eight replicate wells. PHA (1 µg/ml) was added to 4 of the assay replicate wells and cells were incubated for 96 hours. 3H-Thymidine incorporation used to assay cell proliferation. Mock stimulated cells and PHA only stimulated cells used as assay's negative and positive controls respectively. The proliferation was assessed in resting lymphocytes as well as in activated lymphocytes (PHA treated). Mock stimulated cells and PHA only stimulated cells used as assay's negative and positive controls respectively. The results (FIG. 12) clearly show that CM10 has no effect on the proliferation of naïve or activated human lymphocytes. In addition to the PBMC proliferation study, the effect of CM10 on cytokine secretion from human PBMC is assessed. Cytokine secretion studies define the immunomodulatory effect of CM10 and assist in predicting potential side effects.

Example 8

CM10 Selectivity Panel

Characterization of the binding profile was performed using Cell lines over-expressing the different CEACAM family proteins and flow cytometry analysis.

In humans, the CEA family is encoded by 18 genes and 11 pseudogenes on chromosome 19q13.2. Several closely related members belong to the CEACAM family (CEACAM1, 3, 4, 5, 6, 7, 8) and are differentially expressed by various human cell types. The CEACAM proteins have been implicated in various adhesion mediated effects that govern the growth and differentiation of normal and cancerous cells (Gray-Owen and Blumberg 2006, Nat Rev Immunol 6, 433-46). The closely related proteins in the family share a high amino acid similarity that varies from 45% up to 90% similarity between certain members.

Figure 13:
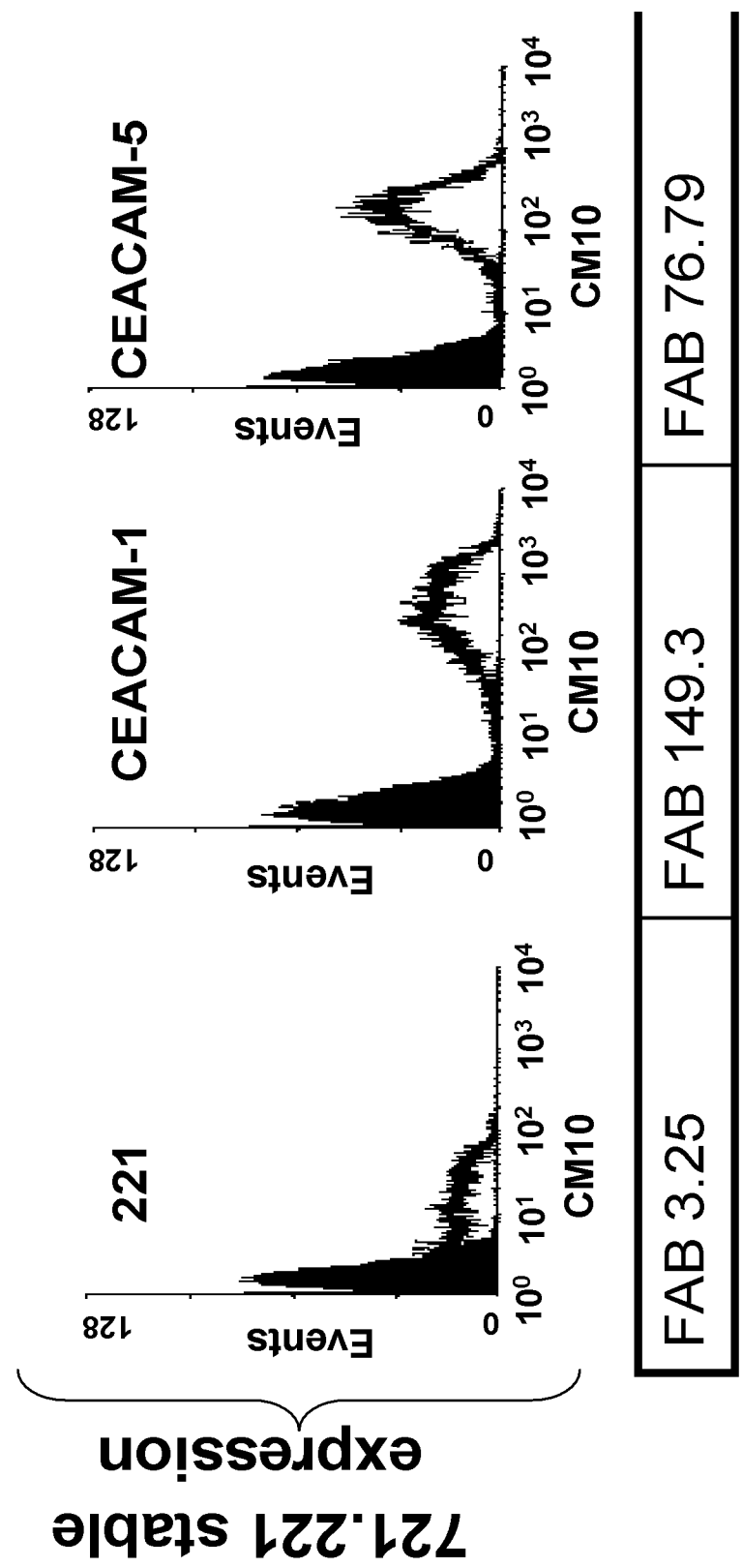
FIG. 13 presents FACS analysis of binding between CM10 to CEACAM family proteins. CEACAM1, 5, 6 and 8 were expressed by 721.221 cells, and CEACAM3 and 4 by HEK293T cells.
Figure 13:
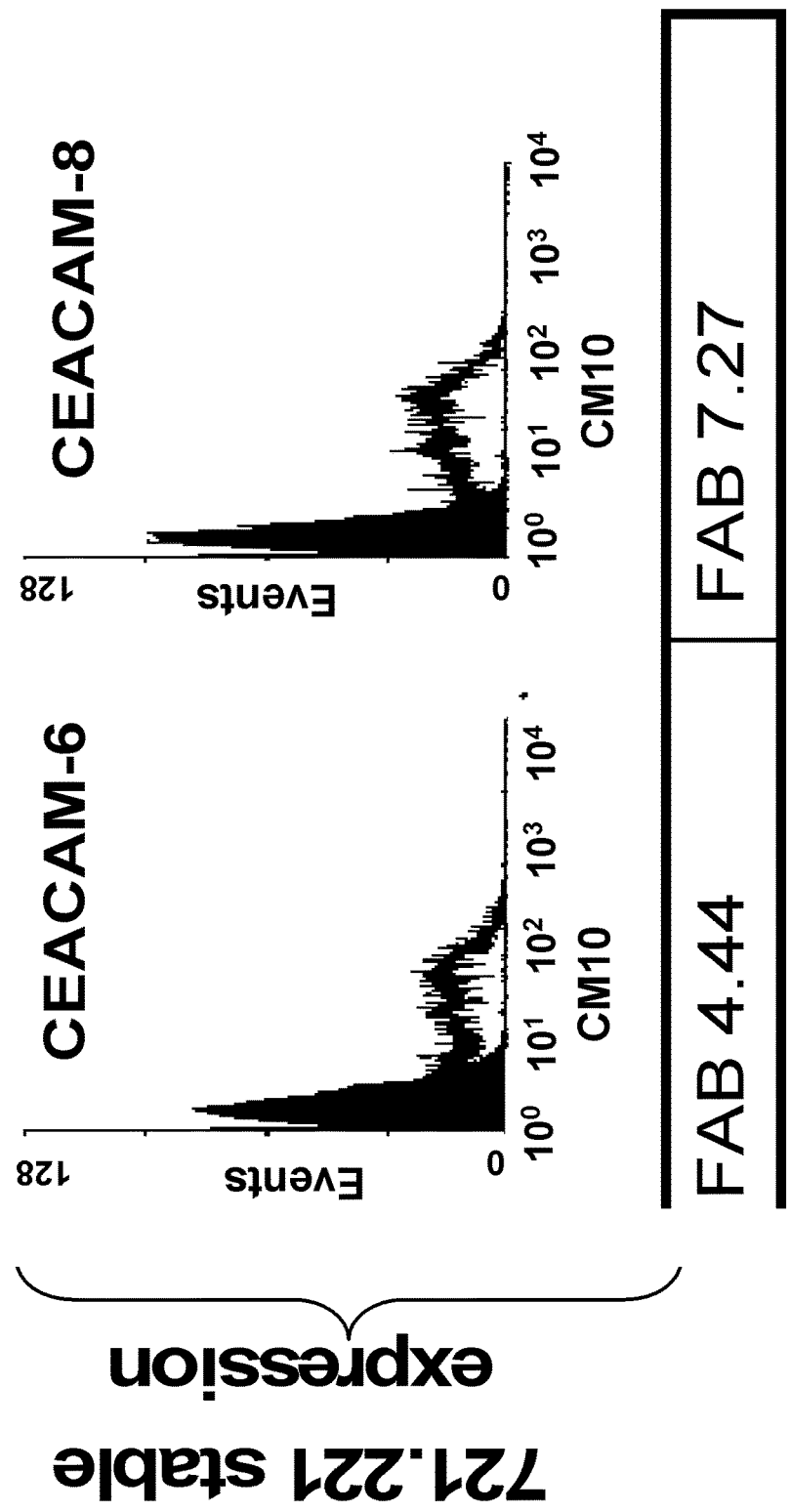
Figure 13:
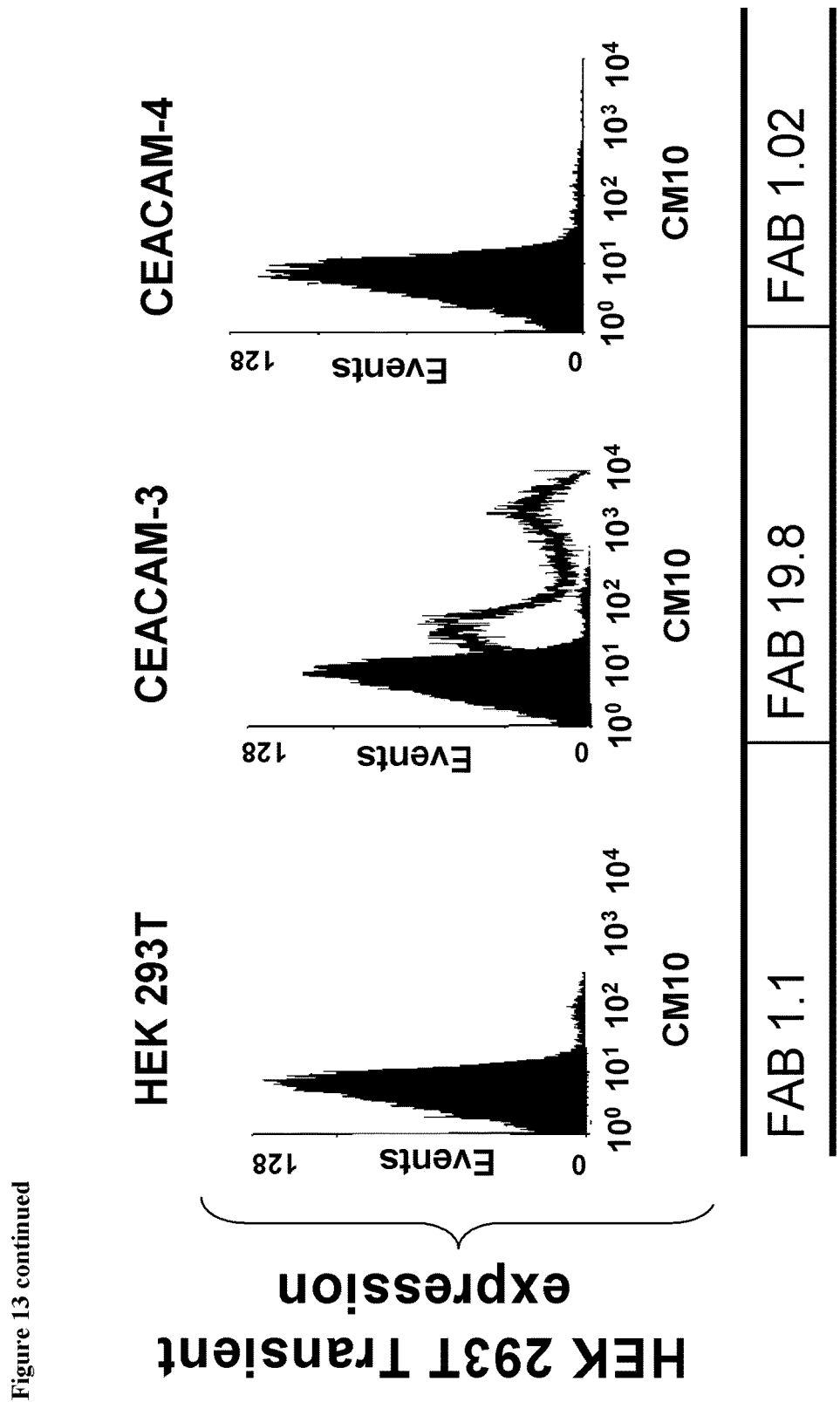

A standard FACS protocol was used with CM10 conjugated to a Biotin molecule and Strep-Avidin APC as secondary agent. 721.221 cells expressing CEACAM1, 5, 6, 8 or HEK 293 T transient expressing CEACAM3, 4, were stained with biotinylated CM10 (1 µg/ml) and Strep-Avidin APC as secondary agent. Empty histograms represent mAb staining while red histograms represent background staining At least 10000 cells were used to analyze CM10 binding in each histogram. FAB was calculated by dividing the MFI of the stained cells in the MFI of the background staining. The results demonstrated in FIG. 13, clearly indicate that CM10 bind strongly to cells expressing CEACAM1. Moderate staining was observed in cells expressing CEACAM3 and 5. Weak or neglect binding was demonstrated in cells expressing CEACAM4, 6, 8.

Conclusions

CM10 is a mAb developed to recognize human CEACAM1, a protein that was found to be associated with cancer, in general, and with Melanoma in particular. The over-expression of CEACAM1 has been identified in a few malignancies among them melanoma, NSCLC, Thyroid cancer and gastric cancer. The evidence indicates that over-expression of CEACAM1 can be correlated with poor prognosis in melanoma and NSCLC patients. CEACAM5 has been found to be over-expressed in a high percentage of many human tumors, including 90% of gastrointestinal, colorectal (CRC) and pancreatic cancers, 70% of non-small cell lung cancer cells and 50% of breast cancers. It is also over-expressed in thyroid, stomach, ovarian and uterine cancers (Thompson, Grunert et al. 1991, J Clin Lab Anal 5, 344-66). CEACAM5 even serves as a clinical marker for liver metastasis in CRC and post-surgical surveillance of colon cancer (Duffy 2001, Clin Chem 47, 624-30). The evidence that CM10 is capable to bind CEACA5 is very important and can expand the possible indications that can be treated by CM10 from 4-5 types of malignancies to above 10. The anti-CEACAM5 agents that have entered clinical trials include anti-CEACAM5 antibodies conjugated to toxic substances such as radioactive substances for both diagnostic purposes and for the treatment of various malignancies. It seems that even these toxic conjugated forms don't show safety problems, which can indicate that CEACAM5 is a safe target (Liersch, et al. 2005, J Clin Oncol 23(27), 6763-70; Ychou, et al. 2008, Clin Cancer Res 14(11), 3487-93). On the other hand, none of these agents target the immunological regulation of tumors, which can be targeted by an antibody which can bind both CEACAM1 and CEACAM5, such as CM10.

Example 9

Epitope Mapping of CM10

To reconstruct discontinuous epitopes of the target molecule, a library of structured peptides was synthesized. The target molecule was the N-domain of the human CEACAM1 molecule having the sequence:

```
                                                         (SEQ ID NO: 35)
  1 QLTTESMPFN VAEGKEVLLL VHNLPQQLFG YSWYKGERVD GNRQIVGYAI    50

51 GTQQATPGPA NSGRETIYPN ASLLIQNVTQ NDTGFYTLQV IKSDLVNEEA   100

101 TGQFHVYP.                                                108
```

The library was synthesized using Pepscan's Chemically Linked Peptides on Scaffolds (CLIPS) technology which allows to structure peptides into single loops, double-loops, triple loops, sheet-like folds, helix-like folds and combinations thereof (Timmerman et al. 2007, J. Mol. Recognit. 20:283-99 and Slootstra et al. 1996, Molecular Diversity 1: 87-96). CLIPS templates are coupled to cysteine residues. The side-chains of multiple cysteines in the peptides are coupled to one or two CLIPS templates. For example, a 0.5 mM solution of the T2 CLIPS template 1,3-bis(bromomethyl)benzene is dissolved in ammonium bicarbonate (20 mM, pH 7.9)/acetonitrile (1:1(v/v). This solution is added onto the peptide arrays. The CLIPS template will bind to side-chains of two cysteines as present in the solid-phase bound peptides of the peptide-arrays (455 wells plate with 3 µl wells). The peptide arrays are gently shaken in the solution for 30 to 60 minutes while completely covered in solution. Finally, the peptide arrays are washed extensively with excess of $H_2O$ and sonicated in disrupt-buffer containing 1 percent SDS/0.1 percent beta-mercaptoethanol in PBS (pH 7.2) at 70° C. for 30 minutes, followed by sonication in $H_2O$ for another 45 minutes. The T3 CLIPS carrying peptides were made in a similar way but with three cysteines.

A total number of 3002 peptides was synthesized that includes: CLIPS matrix set combining two different areas of the entire protein wherein native cysteines are replaced by alanines; Linear peptide sets of length 6, 10, 15, 20, 25 and 33; Linear peptide sets of length 15, where the middle residue is replaced by alanine; CLIPS conformational loop set of length 15 wherein native cysteines are replaced by alanines; and CLIPS conformational loop set of length 15 with the middle residue replace by alanine wherein native cysteines are replaced by alanines.

The binding of antibody to each of the synthesized peptides was tested in a PEPSCAN-based ELISA. The peptide arrays were incubated with primary antibody (CM10) solution (overnight at 4° C.). After washing, the peptide arrays were incubated with a 1/1000 dilution of an antibody peroxidase conjugate for one hour at 25° C. After washing, the peroxidase substrate 2,2'-azino-di-3-ethylbenzthiazoline sulfonate (ABTS) and 2 microliters/milliliter of 3 percent $H_2O_2$ were added. After one hour, the color development was measured. The color development was quantified with a charge coupled device (CCD)-camera and an image processing system.

The values obtained from the CCD camera range from 0 to 3000 mAU, similar to a standard 96-well plate ELISA-reader. The results are quantified and stored into the Peplab database. The binding values are extracted for analysis using graphical representation of data where the values taken by a variable in a two-dimensional map are represented as colors.

Based on the observed binding patterns, the core of the epitope of CM10.S91 consists of residues $_{17}$VLLLVHN-LPQQLF$_{29}$. A secondary binding region was observed on sequence around $_{68}$YPNASLLIQNVT$_{79}$. When the observed binding patterns are compared to the available crystal structure of the target protein, it is proposed that the discontinuous epitope for CM10.S91 consists of $_{17}$VLLL-VHNLPQQLF$_{29}$ (core) together with $_{68}$PNASLLI$_{75}$ (support).

Example 10

Additional Experiments Assessing the Activity of CM10

Granzyme B Secretion by Effector Cells as a Potential PD Marker

The development of robust pharmacodynamic (PD) markers is critical for improving the success of drugs in clinical trials and assists in selection of an optimal drug dose to balance efficacy and toxicity. PD markers are often proximal in a molecular pathway to the drug target and are used to measure the effect of a drug regardless of therapeutic effect. Granzyme B is a serine protease that is released through cytoplasmic granules of cytotoxic T cells (CTLs) and NK cells upon recognition of specific targets. This in turn mediates the apoptosis of the target cells. We sought to determine if CM10 enhances granzyme B secretion from effector NK and T cells in the presence of specific target cells, thus enabling the observed enhanced killing of the target cells by the antibody.

TIL were incubated with CM10 (0.2 µg/ml, 1 µg/ml, 5 µg/ml or 10 µg/ml) or an isotype matched control Ab (IPI-Ipilimumab 10 µg/ml) for 30 minutes at 37° C.; Target positive melanoma cells expressing CEACAM1 and HLA-A2-SKMEL5, were added for an overnight incubation at effector-to-target ratio of 2.5:1. Granzyme B secretion was measured by ELISA. Results represent the mean±S.E of granzyme B release values from 6 repeats per treatment. Similar results were seen in another independent experiment.

Figure 15:
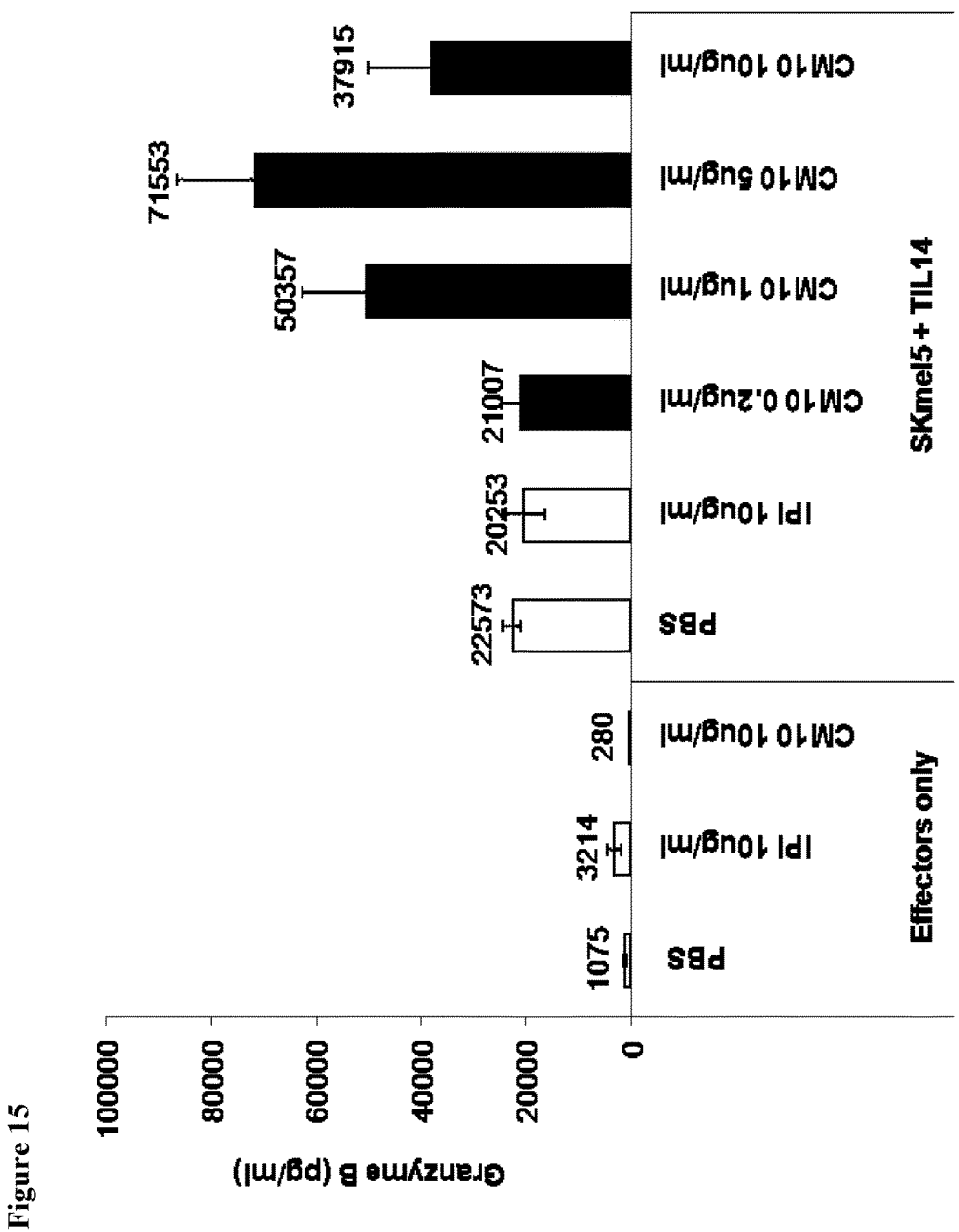
FIG. 15 demonstrates that CM10 enhances granzyme B secretion of TIL in the presence of CEACAM1 and HLA-A2 positive melanoma cells.

A represented in FIG. 15 TIL secretes low initial levels of granzyme B that remained low in the presence of CM10 alone. Only when the target cells were added to the TIL, granzyme B elevated dramatically. Yet, CM10 was able to significantly increase granzyme B secretion above the high initial levels. Similar results were seen when NK92MI cells were used as effector cells demonstrating that CM10 can enhance granzyme B secretion form NK cells in a similar manner. The use of Granzyme B as PD marker to CM10 treatment is also examined in complementary set of experiments including in vivo models and patients specimens.

CM10 Blocks CEACAM1-CEACAM5 Interactions

Carcinoembryonic antigen (CEA, CEACAM5, and CD66e) has been found to be associated with various types of cancers, particularly colorectal carcinoma, as well as gastrointestinal, pancreatic cancers, non-small cell lung cancer, breast cancers, thyroid, stomach and ovarian cancer. The molecule has been developed to be a target for cancer diagnosis and therapy.

Homophilic CEACAM1 interactions between a MHC-I-deficient melanoma cell line and NK cells significantly inhibited killing of the cancer cells by the NK cells (Markel et al J Immunol. 2002; 168:2803-2810). Similarly, forced expression of CEACAM5 in HLA class I-defective 721.221 cells also suppressed NK-mediated cytotoxicity (Stern et al J Immunol. 2005; 174:6692-6701), indicating CEACAM5-CEACAM1 heterophilic interactions are also able to trigger inhibitory CEACAM1 signaling in immune cells.

CEACAM1 positive cell line (SKMel 5) was incubated with an isotype control or CM10 in various concentrations, unbound CM10 was washed twice, followed by incubation with or without soluble biotinylated CEACAM5. The binding of the biotinylated CEACAM5 to the cells was detected by a secondary strepavidin-APC and FACS analysis. The results represent the mean of duplicate wells±SE. Similar results were obtained in two other independent experiments.

Figure 16:
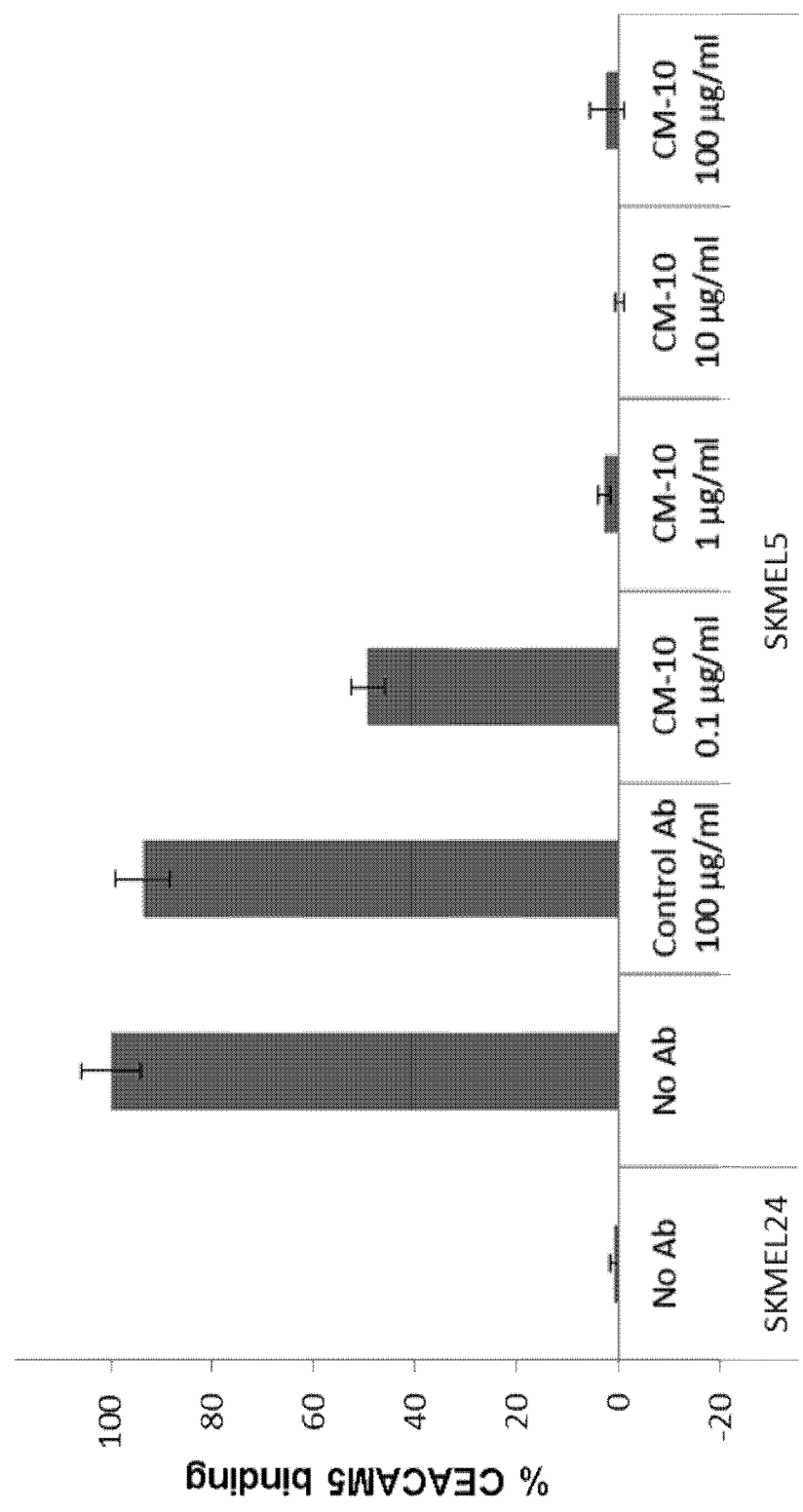
FIG. 16 shows that CM10 blocks CEACAM1-CEACAM5 interactions.

The results of FIG. 16 demonstrate that CM10 inhibits the binding between CEACAM1 to CEACAM5 in a dose-dependent manner Therefore CM10 can be used to treat malignancies that express high level of CEACAM5 and exploit the CEACAM1-CEACAM5 axis in order to suppress the immune cells.

CM10 Enhances HLA Restricted T Cell Killing

Cytotoxic T cells destroy virally infected cells and tumor cells, and are also implicated in transplant rejection. These cells recognize their targets by binding to antigens associated with HLA molecules, which are present on the surface of nearly every cell of the body. The killing of infected or malignant cells requires the recruitment of several pathways in order to generate proper response.

This set of assays was sought to determine if CM10 enhances the "natural" CTL activity which is HLA restricted or alternatively causes a general stimulation of the immune system.

TIL were incubated with CM10 (0.2 µg/ml, 1 µg/ml, 5 µg/ml or 10 µg/ml) or an isotype matched control antibody for 30 minutes at 37° C. Target melanoma cells SKMEL5, expressing CEACAM1 and HLA-A2 were pre-incubated with or without HLA-A2 blocking monoclonal antibody for 1 hour and were added for an overnight incubation at effector-to-target ratio of 2.5:1. Killing was determined by standard LDH release assay. Results represent the mean±S.E of LDH release values from 3 repeats per treatment.

Figure 17:
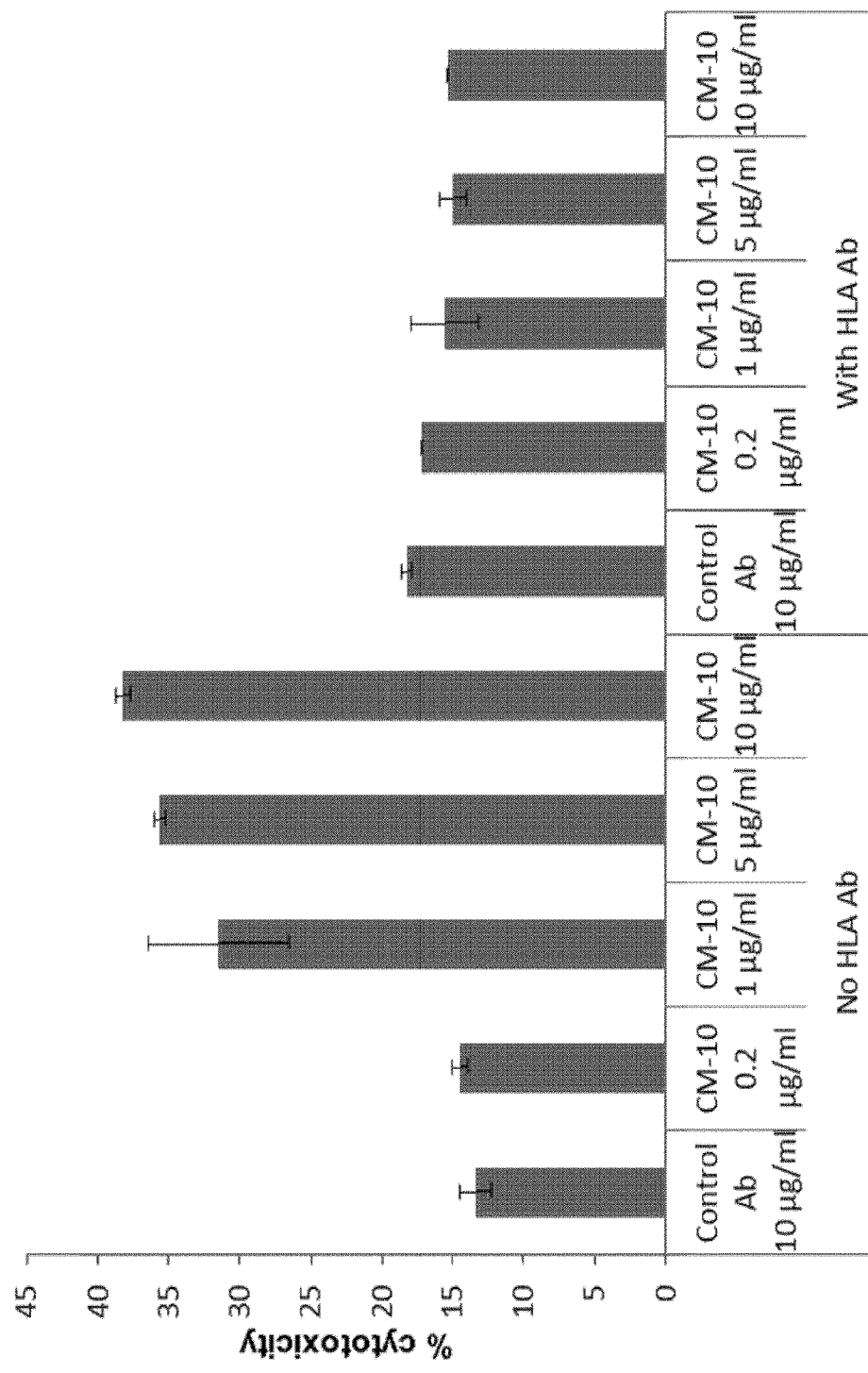
FIG. 17 presents CM10 enhancement of HLA restricted T cell killing.

The results in FIG. 17 demonstrate that in the presence of HLA-A2 blocking antibodies CM10 was unable to augment melanoma cell killing by the TIL and that CM10's activity is HLA restricted. Similar result was seen in another independent experiment. It is therefore suggested that in accordance with these results CM10 will improve the activity of CTLs against malignant cells in vivo and will not facilitate non-specific activation of the immune system.

The Immunomodulatory Activity of CM10 Inhibits Tumor Growth In-vivo

One of the most widely used models to assess the in vivo action of a novel anti cancer agents is the human tumor xenograft model. In this model, human tumor cells are transplanted under the skin into immunocompromised mice that do not reject human cells. Depending upon the number of cells injected and the cells' growth rate, the tumor develops over several weeks, and the response to appropriate therapeutic regimes can be studied in vivo. The advantage of a model that involves treatment in early stages of tumor formation is the opportunity to examine the agent's influence in a setting that can be more similar to metastasis spread in patients and to identify the effect of the treatment on initial tumor implantation.

The immunomodulatory activity of CM10 in vivo was therefore examined in SCID-NOD mice engrafted with human melanoma cells under prophylactic treatment regime. SCID-NOD mice were randomized according to the five treatment groups indicated in FIG. 18. $6 \times 10^6$ SKmel5 cells (melanoma cell line) were injected SC in Day 0. Mice were treated with antibodies/TIL as indicated in the figure. Arrows indicate time of administration; Thin arrows represent antibodies-0.25 mg/mouse/injection (CM10, IgG control and Ipilimumab control) and wide arrows for TIL ($20 \times 10^{\char`\^}6$ cell per mouse per injection). The tumors' volume was blindly measured 2-3 times per week. The results represent average tumor volumes±SE from 8-9 mice per group.

Figure 18:
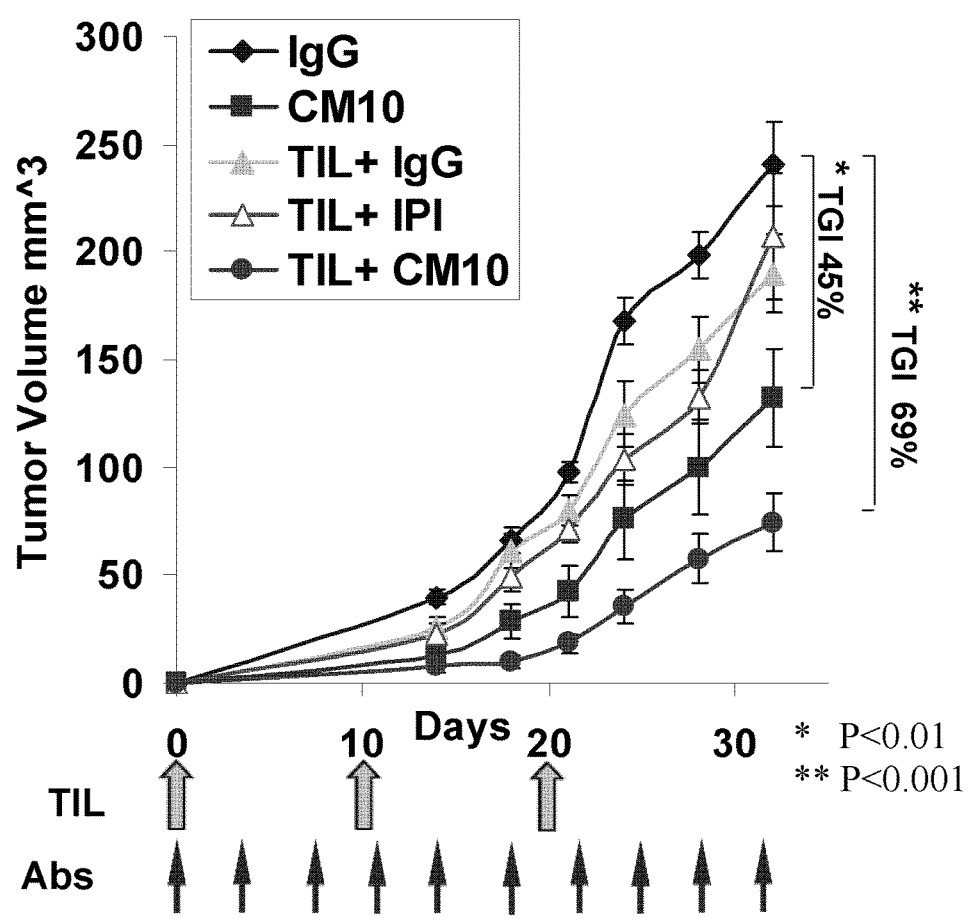
FIG. 18 demonstrates the immunomodulatory activity of CM10 inhibits tumor growth in-vivo.

FIG. 18 shows that the combination of adoptive human T cell transfer with CM10 injections exhibited significant synergism and strongly inhibited xenograft growth compared to the isotype control group (69% TGI). The results demonstrate that CM10 also has an effect as a single agent (45% TGI at day 32) and probably worked directly on the tumor cells or the tumors' surroundings by inhibiting proliferation, angiogenesis or through other biological pathways.

In the same set of experiments the tumors' total weight was determined at the experiment termination day. The results obtained support the volume measurements, and show a dramatic decrease in the tumor burden of the TIL+CM10 treated group and also statistically significant reduction in the tumors' weight in the CM10 treated group.

CM10 Enhances the Immunomodulatory Killing Activity of NK Cells on CEACAM1-positive Pancreatic Cancer Cell Lines Preliminary screening showed that pancreatic cancer cell lines and patient specimens express high levels of CEACAM1 (94% from pancreatic cancer specimens were CEACAM1 positive). Therefore, an experiment was conducted to examine if CM10 can enhanced the activity of immune cells against pancreatic cancer cell lines. Killing assays were conducted by co-culture of NK92MI cells that were pre-treated with various concentrations of CM10 with different CEACAM1 positive target pancreatic cancer cell lines. NK 92MI were incubated with CM10 (0.2 µg/ml, 1 µg/ml or 10 µg/ml) or an isotype matched control Ab (10 µg/ml) for 30 minutes at 37° C.; A. Target cells expressing CEACAM1 were added for additional 5 hours at effector-to-target ratio of 2.5:1 (COLO-357) or overnight at an effector-to-target ratio of 5:1 (BXPC3). Results represent an average of % cytotoxicity±SE as determined by classical LDH release assay from triplicate wells per treatment.

Figure 19:
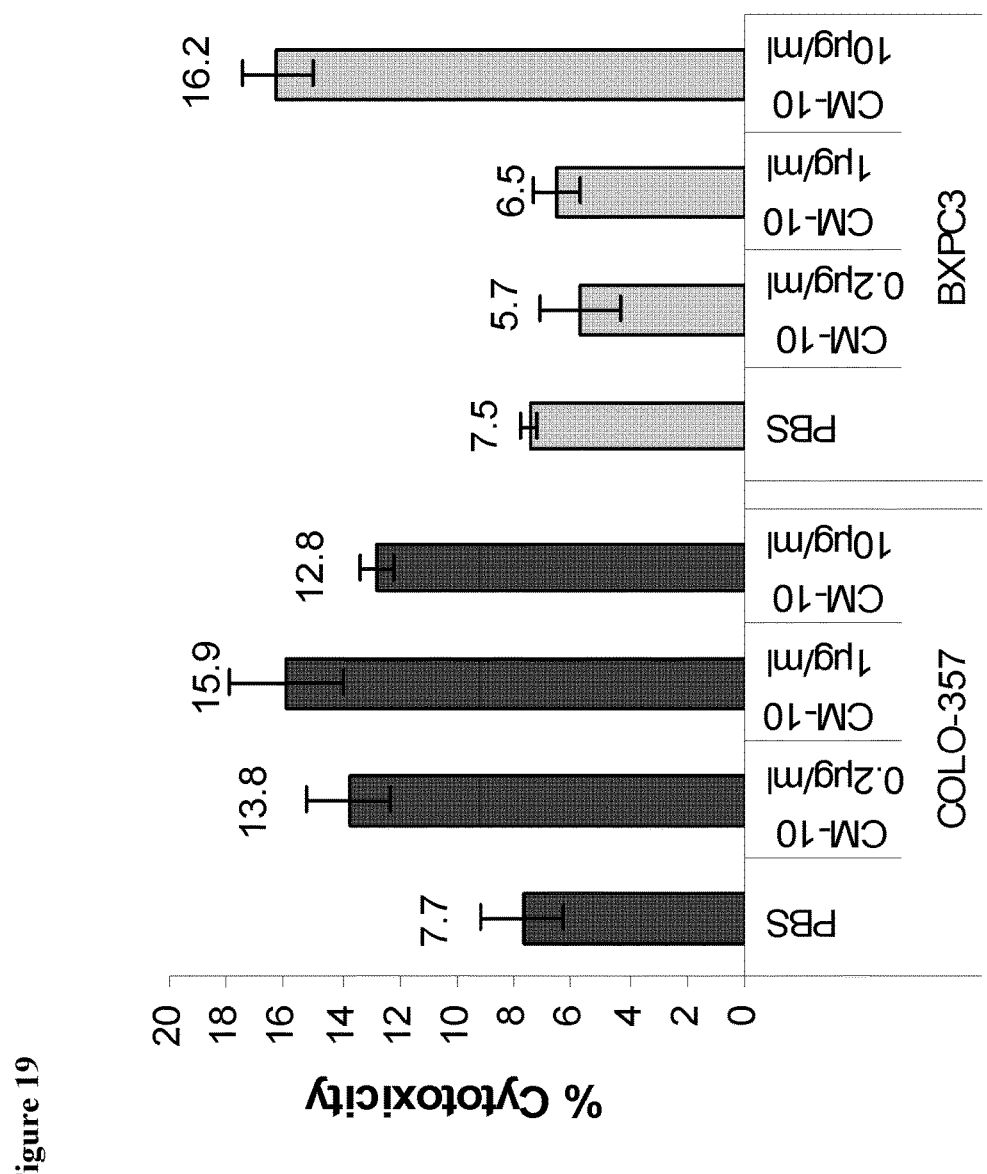
FIG. 19: indicates that CM10 enhances the killing activity of NK cells on CEACAM1-positive pancreatic cancer cell lines COLO-357 and BXPC3.

The results represented in FIG. 19 show that although the killing of the pancreatic cancer cells by the NK cells was relatively low, CM10 enhanced this activity by up to 2 folds from the baseline cytotoxicity (PBS or control Ab). Similar results were seen in additional two lines.

CM10 Enhances Granzyme B Secretion of NK Cells in the Presence of CEACAM1-positive Pancreatic Cancer Cell Lines The experiment was designed to determine whether similarly to the melanoma cells, CM10 can enhance the secretion of granzyme B from NK cells in the presence of pancreatic cancer cells. In a similar setting to the killing assay, NK cells were pre-treated with various concentrations of CM10 and then co-cultured with four different target pancreatic cancer cell lines. The supernatants were analyzed for granzyme B content by a specific ELISA. NK 92MI were incubated with CM10 (0.2 µg/ml, 1 µg/ml or 10 µg/ml) or an isotype matched control antibody (10 µg/ml) for 30 minutes at 37° C. Target pancreatic cells expressing CEACAM1 were added for additional 5 hours at effector-to-target ratio of 2.5:1 A. (COLO-357 and ASPC-1) and B. (SU8686) or E:T of 10:1 C. (BXPC3). Granzyme B secretion was measured by ELISA. Results represent the mean±S.E of granzyme B release values from 2-6 repeats per treatment.

Figure 20:
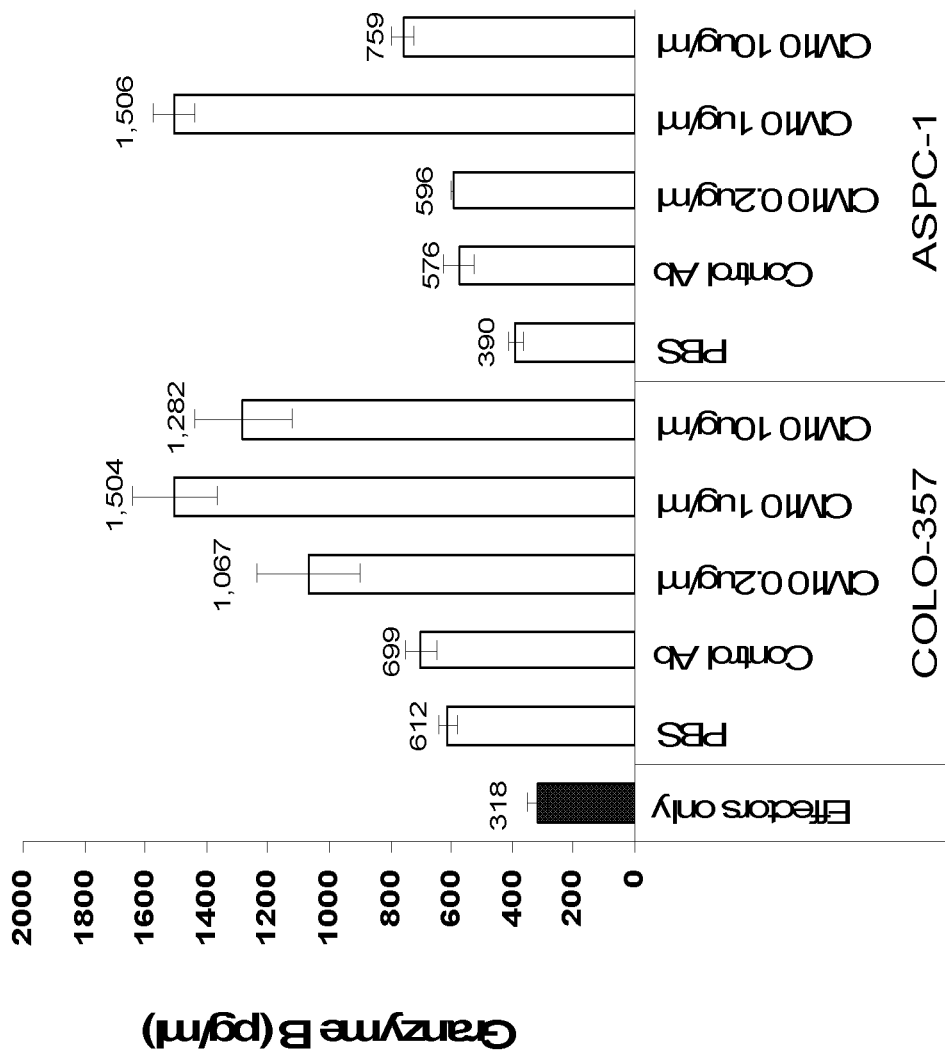
FIG. 20: demonstrates that CM10 enhances granzyme B secretion of NK cells in the presence of CEACAM1-positive pancreatic cancer cell lines.
Figure 20:
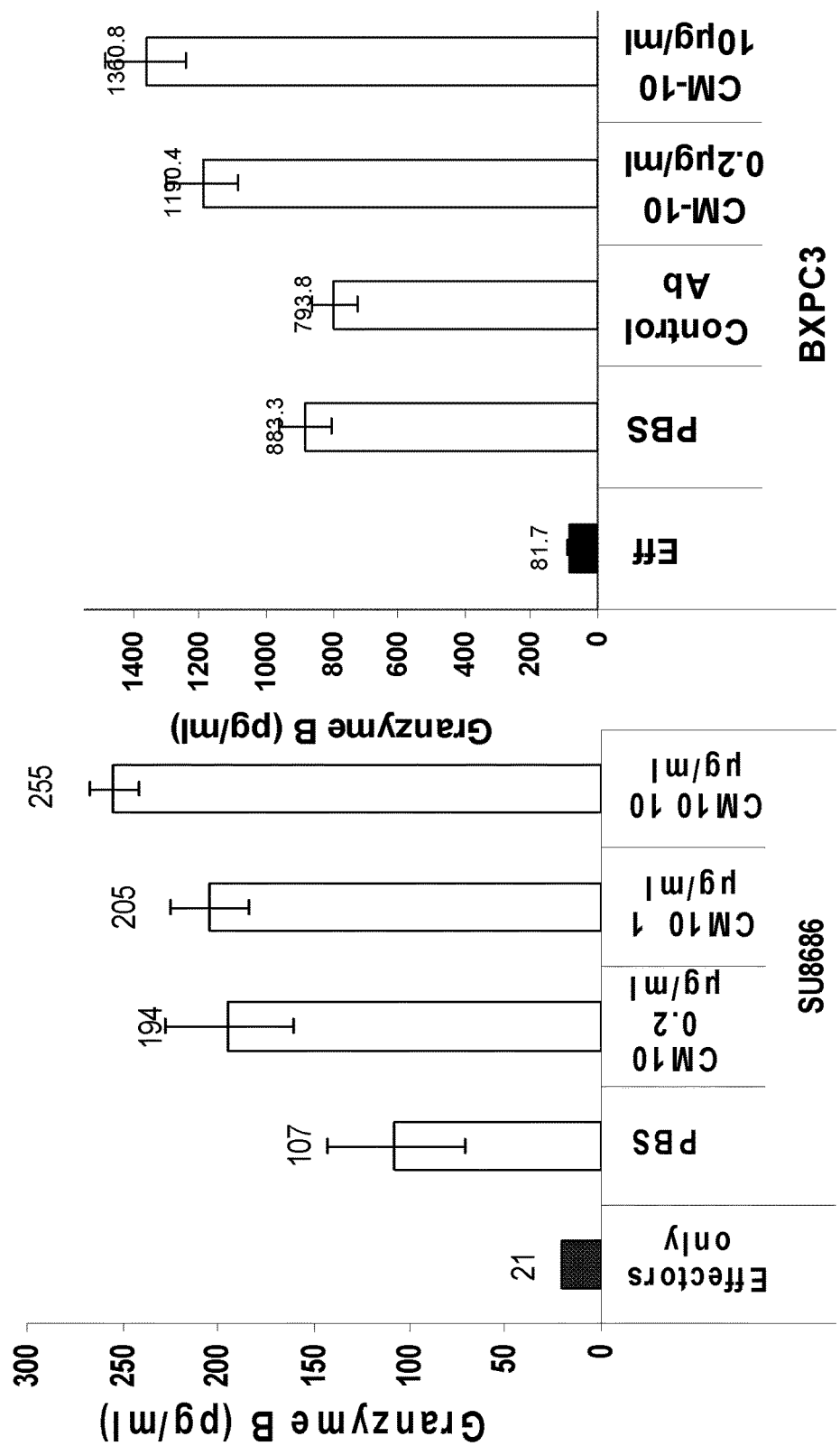

FIG. 20 clearly demonstrates that CM10 increases granzyme B secretion from NK cells in the presence of pancreatic cancer cells.

Example 11

Humanized and Human Antibodies

A humanized antibody typically has a human framework grafted with non human CDRs. Thus, a humanized antibody has one or more amino acid sequence introduced into it from a source which is non-human. These non-human amino acid residues are often referred to as "import" residues, which are typically taken from an "import" variable domain. Humanization can be essentially performed following the method of Winter and co-workers (Jones et al., Nature, 321:522-525, 1986; Riechmann et al., Nature, 332:323-327, 1988; Verhoeyen et al., Science, 239:1534-1536, 1988), by substituting rodent CDRs or CDR sequences for the corresponding sequences of a human antibody. Accordingly, such "humanized" antibodies are chimeric antibodies (U.S. Pat. No. 4,816,567) wherein substantially less than an intact human variable domain has been substituted by the corresponding sequence from a non-human species. In practice, humanized antibodies are typically human antibodies in which some CDR residues and possibly some FR residues are substituted by residues from analogous sites in rodent antibodies.

The choice of human variable domains, both light and heavy, to be used in making the humanized antibodies is very important to reduce antigenicity. According to the so-called "best-fit" method, the sequence of the variable domain of a rodent antibody is screened against the entire library of known human variable-domain sequences. The human sequence which is closest to that of the rodent is then accepted as the human framework (FR) for the humanized antibody (Sims et al., J. Immunol., 151:2296, 1993; Chothia et al., J. Mol. Biol., 196:901, 1987). Another method uses a particular framework derived from the consensus sequence of all human antibodies of a particular subgroup of light or heavy chains. The same framework may be used for several different humanized antibodies (Carter et al., Proc. Natl. Acad. Sci. USA, 89:4285, 1992; Presta et al., J. Immunol., 151:2623, 1993).

It is further important that antibodies be humanized with retention of high affinity for the antigen and other favorable biological properties. To achieve this goal, according to a preferred method, humanized antibodies are prepared by a process of analysis of the parental sequences and various conceptual humanized products using three-dimensional models of the parental and humanized sequences. Three-dimensional immunoglobulin models are commonly available and are familiar to those skilled in the art. Computer programs are available which illustrate and display probable three-dimensional conformational structures of selected candidate immunoglobulin sequences. Inspection of these displays permits analysis of the likely role of the residues in the functioning of the candidate immunoglobulin sequence, i.e., the analysis of residues that influence the ability of the candidate immunoglobulin to bind its antigen. In this way, FR residues can be selected and combined from the recipient and import sequences so that the desired antibody characteristic, such as increased affinity for the target antigen(s), is achieved. In general, the CDR residues are directly and most substantially involved in influencing antigen binding.

Alternatively, it is now possible to produce transgenic animals (e.g., mice) that are capable, upon immunization, of producing a full repertoire of human antibodies in the absence of endogenous immunoglobulin production. For example, it has been described that the homozygous deletion of the antibody heavy-chain joining region (JH) gene in chimeric and germ-line mutant mice results in complete inhibition of endogenous antibody production. Transfer of the human germ-line immunoglobulin gene array in such germ-line mutant mice will result in the production of human antibodies upon antigen challenge (e.g., Jakobovits et al., Proc. Natl. Acad. Sci. USA, 90:2551, 1993; Jakobovits et al., Nature, 362:255-258, 1993; Bruggermann et al., Year in Immuno., 7:33, 1993; and Duchosal et al. Nature 355:258, 1992. Human antibodies can also be derived from phage-display libraries (Hoogenboom et al., J. Mol. Biol., 227:381, 1991; Marks et al., J. Mol. Biol., 222:581-597, 1991; Vaughan et al. Nature Biotech 14:309, 1996).

Example 12

Antibody Fragments

Various techniques have been developed for the production of antibody fragments. Traditionally, these fragments were derived via proteolytic digestion of intact antibodies (e.g., Morimoto et al., Journal of Biochemical and Biophysical Methods 24:107-117, 1992 and Brennan et al., Science, 229:81, 1985). However, these fragments can now be produced directly by recombinant host cells. For example, the antibody fragments can be isolated from the antibody phage libraries discussed above. Alternatively, Fab'-SH fragments can be directly recovered from E. coli and chemically coupled to form F(ab')$_2$ fragments (Carter et al., Bio/Technology 10:163-167, 1992). According to another approach, F(ab')$_2$ fragments can be isolated directly from recombinant host cell culture. Other techniques for the production of antibody fragments will be apparent to the skilled practitioner. In other embodiments, the antibody of choice is a single chain Fv fragment (scFv).

Example 13

Potency of Anti CEACAM Antibody Against Viral Infections

The following experiments are used to determine the potential of CM10 against viral infection. The experiments include different target cells, various virus and several in vivo and in vitro models.

Detection/diagnosis: Examination of CEACAM expression level in cell lines and primary cells infected with different virus types, by FACS analysis, RT PCR and Immunohistochemistry.

Prevention: pre-incubation of target cells with anti CEACAM antibody and determination of the viral load or viral replication post viral infection.

Treatment: after viral infection the infected cell are incubated with immune system cell and the killing ability of the effectors cells and the viral load is examined. In addition, the viral load and replication and overall survival are determined in vivo after virus infection and treatment with anti CEACAM antibodies.

The foregoing description of the specific embodiments will so fully reveal the general nature of the invention that others can, by applying current knowledge, readily modify and/or adapt for various applications such specific embodiments without undue experimentation and without departing from the generic concept, and, therefore, such adaptations and modifications should and are intended to be comprehended within the meaning and range of equivalents of the disclosed embodiments. It is to be understood that the phraseology or terminology employed herein is for the purpose of description and not of limitation. The means, materials, and steps for carrying out various disclosed functions may take a variety of alternative forms without departing from the invention.

The invention claimed is:

1. A chimeric monoclonal antibody which recognizes CEACAM1 comprising a heavy chain sequence set forth in SEQ ID NO: 30 and a light chain sequence set forth in SEQ ID NO: 31.

2. The chimeric monoclonal antibody of claim 1, produced from DNA sequences of the heavy and light chains contained in a plasmid deposited on Sep. 28, 2011 under ATCC Accession Number PTA-12130.

3. An isolated polynucleotide encoding the chimeric monoclonal antibody according to claim 1.

4. A plasmid comprising at least one isolated polynucleotide sequence according to claim 3.

5. A plasmid according to claim 4, deposited on Sep. 28, 2011 under ATCC Accession Number PTA-12130.

6. A pharmaceutical composition comprising a therapeutically effective amount of the chimeric monoclonal antibody according to claim 1; and a pharmaceutically acceptable carrier.

7. A diagnostic composition comprising at least one chimeric monoclonal antibody according to claim 1; and an optional carrier or excipient.

8. A method of attenuating or treating a disease or disorder associated with expression, activation or function of CEACAM, comprising administering the pharmaceutical composition of claim 6 to a subject in need thereof.

9. The method of claim 8, wherein the disease or disorder is a CEACAM1-expressing cancer.

10. The method of claim 8, wherein the disease or disorder is a viral infection that increases expression of CEACAM1.

11. The method according to claim 8, wherein the chimeric monoclonal antibody contained in the pharmaceutical composition is attached to a cytotoxic moiety and the disease is cancer.

12. The method of claim 8, further comprising administering to the subject CEACAM1-expressing lymphocytes.

13. The method of claim 12 wherein the lymphocytes comprise T cells, NK cells or Tumor Infiltrating Lymphocyte.

14. A method of immunomodulation, the method comprising contacting a CEACAM-expressing lymphocyte with the antibody according to claim 1.

15. A method of inhibiting migration of a CEACAM expressing tumor cell, the method comprising contacting the CEACAM expressing tumor cell with the antibody according to claim 1, thereby inhibiting migration of a CEACAM expressing tumor cell.

16. A method of inhibiting CEACAM homotypic or heterotypic protein-protein interaction, the method comprising contacting a CEACAM1-expressing lymphocyte with the antibody according to claim 1, thereby inhibiting CEACAM1 homotypic or heterotypic protein-protein interaction.

17. A method for increasing the duration or progression of response or survival of a subject having a CEACAM1-expressing cancer, comprising administering to the subject effective amounts of a composition comprising a monoclonal antibody according to claim 1, and an anti-neoplastic composition, wherein said antineoplastic composition comprises at least one chemotherapeutic agent, whereby the co-administration of the antibody and the anti-neoplastic composition effectively increases the duration or progression of survival.

18. A method for diagnosing a cancer in a subject in need thereof, the method comprising contacting a biological sample derived from the subject with the diagnostic composition of claim 7, wherein a complex formation beyond a predetermined threshold is indicative of the cancer in the subject.

19. A method for diagnosing a disease or disorder associated with CEACAM expression, comprising the steps of:
   i. incubating a biological sample with a monoclonal antibody according to claim 1;
   ii. detecting the bound CEACAM using a detectable probe;
   iii. comparing the amount of (ii) to a standard curve obtained from reference samples containing known amounts of CEACAM;
   iv. calculating the amount of the CEACAM in the biological sample from the standard curve; and
   v. comparing the amount of (iv) to a normal CEACAM amount.

* * * * *